US008106021B2

(12) United States Patent
Chen et al.

(10) Patent No.: US 8,106,021 B2
(45) Date of Patent: *Jan. 31, 2012

(54) BENZYLBENZENE DERIVATIVES AND METHODS OF USE

(75) Inventors: Yuanwei Chen, North Haven, CT (US); Huawei Cheng, Shanghai (CN); Shengbin Li, Shanghai (CN); Yuelin Wu, Shanghai (CN); Yan Feng, Shanghai (CN); Binhua Lv, Shanghai (CN); Baihua Xu, Shanghai (CN); Brian Seed, Boston, MA (US); Michael J. Hadd, San Diego, CA (US); Yanli Song, Shanghai (CN); Jiyan Du, Shanghai (CN); Congna Wang, Shanghai (CN); Jacques Y. Roberge, Shanghai (CN)

(73) Assignee: Theracos, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/917,367

(22) Filed: Nov. 1, 2010

(65) Prior Publication Data

US 2011/0207661 A1 Aug. 25, 2011

Related U.S. Application Data

(63) Continuation of application No. 12/197,095, filed on Aug. 22, 2008, now Pat. No. 7,838,499.

(60) Provisional application No. 60/957,625, filed on Aug. 23, 2007.

(51) Int. Cl.
*A01N 43/04* (2006.01)
*A61K 31/70* (2006.01)
(52) U.S. Cl. .......................................................... 514/23
(58) Field of Classification Search ........................ None
See application file for complete search history.

(56) References Cited

U.S. PATENT DOCUMENTS

| | | |
|---|---|---|
| 6,414,126 B1 | 7/2002 | Ellsworth et al. |
| 6,515,117 B2 | 2/2003 | Ellsworth et al. |
| 6,555,519 B2 | 4/2003 | Washburn |
| 6,683,056 B2 | 1/2004 | Washburn et al. |
| 6,774,112 B2 | 8/2004 | Gougoutas |
| 6,936,590 B2 | 8/2005 | Washburn et al. |
| 7,094,763 B2 | 8/2006 | Rybczynski et al. |
| 7,371,732 B2 | 5/2008 | Eickelmann et al. |
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,417,032 B2 | 8/2008 | Eckhardt et al. |
| 7,419,959 B2 | 9/2008 | Eckhardt et al. |
| 7,838,499 B2 * | 11/2010 | Chen et al. ................ 514/23 |
| 2003/0087843 A1 | 5/2003 | Washburn |
| 2004/0138439 A1 | 7/2004 | Deshpande et al. |
| 2005/0187168 A1 | 8/2005 | Eickelmann et al. |
| 2005/0209166 A1 | 9/2005 | Eckhardt et al. |
| 2005/0209309 A1 | 9/2005 | Sato et al. |
| 2005/0233982 A1 | 10/2005 | Himmelsbach et al. |
| 2005/0233988 A1 | 10/2005 | Nomura et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0122126 A1 | 6/2006 | Imamura et al. |
| 2006/0142210 A1 | 6/2006 | Eckhardt et al. |
| 2006/0189548 A1 | 8/2006 | Himmelsbach et al. |
| 2006/0234953 A1 | 10/2006 | Himmelsbach et al. |
| 2006/0234954 A1 | 10/2006 | Urbanski |
| 2006/0247179 A1 | 11/2006 | Fushimi et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0049537 A1 | 3/2007 | Eckhardt et al. |
| 2007/0054867 A1 | 3/2007 | Eckhardt et al. |
| 2007/0185197 A1 | 8/2007 | Fujikura et al. |
| 2007/0197450 A1 | 8/2007 | Fushimi et al. |
| 2007/0249544 A1 | 10/2007 | Himmelsbach et al. |
| 2008/0132563 A1 | 6/2008 | Kakinuma et al. |
| 2008/0318874 A1 | 12/2008 | Matsuoka et al. |
| 2009/0023913 A1 | 1/2009 | Eckhardt et al. |
| 2009/0030006 A1 | 1/2009 | Kobayashi et al. |

FOREIGN PATENT DOCUMENTS

| | | |
|---|---|---|
| CA | 2 539 032 A1 | 3/2005 |
| CA | 2 548 353 A1 | 7/2005 |
| WO | WO 01/27128 A1 | 4/2001 |
| WO | WO 01/74834 A1 | 10/2001 |
| WO | WO 01/74835 A1 | 10/2001 |
| WO | WO 02/083066 A2 | 10/2002 |
| WO | WO 02/083066 A3 | 10/2002 |
| WO | WO 03/020737 A1 | 3/2003 |
| WO | WO 03/099836 A1 | 12/2003 |

(Continued)

OTHER PUBLICATIONS

Banker, G. S. et al. "Modern Pharmaceutics, 3ed.", Marcel Dekker, New York, 1996, p. 596.
Wolff, Manfred E. "Burger's Medicinal Chemistry, 5ed, Part I," John Wiley & Sons, 1995, pp. 975-977.
International Search Report mailed on Nov. 17, 2008, for International Application No. PCT/US08/74058, filed on Aug. 22, 2008, 2 pages.

*Primary Examiner* — Traviss C McIntosh, III

(74) *Attorney, Agent, or Firm* — Kilpatrick Townsend & Stockton LLP.

(57) ABSTRACT

Provided are compounds having an inhibitory effect on sodium-dependent glucose cotransporter SGLT. The invention also provides pharmaceutical compositions, methods of preparing the compounds, synthetic intermediates, and methods of using the compounds, independently or in combination with other therapeutic agents, for treating diseases and conditions which are affected by SGLT inhibition.

23 Claims, 20 Drawing Sheets

FOREIGN PATENT DOCUMENTS

| | | | |
|---|---|---|---|
| WO | WO 2004/063209 | A2 | 7/2004 |
| WO | WO 2004/063209 | A3 | 7/2004 |
| WO | WO 2005/021566 | A2 | 3/2005 |
| WO | WO 2005/021566 | A3 | 3/2005 |
| WO | WO 2005/063785 | A2 | 7/2005 |
| WO | WO 2005/063785 | A3 | 7/2005 |
| WO | WO 2005/085237 | A1 | 9/2005 |
| WO | WO 2005/092877 | A1 | 10/2005 |
| WO | WO 2006/002912 | A1 | 1/2006 |
| WO | WO 2006/008038 | A1 | 1/2006 |
| WO | WO 2006/010557 | A1 | 2/2006 |
| WO | WO 2006/011469 | A1 | 2/2006 |
| WO | WO 2006/018150 | A1 | 2/2006 |
| WO | WO 2006/034489 | A2 | 3/2006 |
| WO | WO 2006/034489 | A3 | 3/2006 |
| WO | WO 2006/037537 | A2 | 4/2006 |
| WO | WO 2006/037537 | A3 | 4/2006 |
| WO | WO 2006/064033 | A2 | 6/2006 |
| WO | WO 2006/064033 | A3 | 6/2006 |
| WO | WO 2006/073197 | A1 | 7/2006 |
| WO | WO 2006/080421 | A1 | 8/2006 |
| WO | WO 2006/089872 | A1 | 8/2006 |
| WO | WO 2006/108842 | A1 | 10/2006 |
| WO | WO 2006/117359 | A1 | 11/2006 |
| WO | WO 2006/117360 | A1 | 11/2006 |
| WO | WO 2006/120208 | A1 | 11/2006 |
| WO | WO 2007/000445 | A1 | 1/2007 |
| WO | WO 2007/014894 | A2 | 2/2007 |
| WO | WO 2007/014894 | A3 | 2/2007 |
| WO | WO 2007/025943 | A2 | 3/2007 |
| WO | WO 2007/025943 | A3 | 3/2007 |
| WO | WO 2007/028814 | A1 | 3/2007 |
| WO | WO 2007/136116 | A2 | 11/2007 |
| WO | WO 2007/136116 | A3 | 11/2007 |
| WO | WO 2009/026537 | A1 | 2/2009 |

* cited by examiner

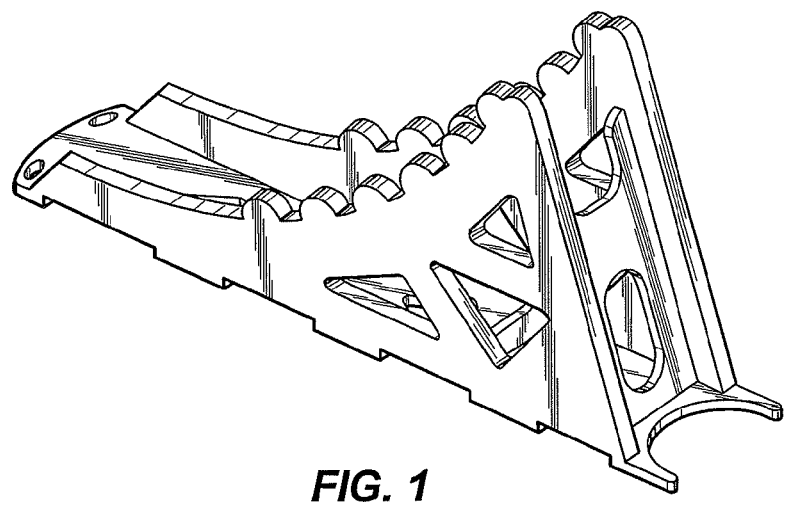
FIG. 1
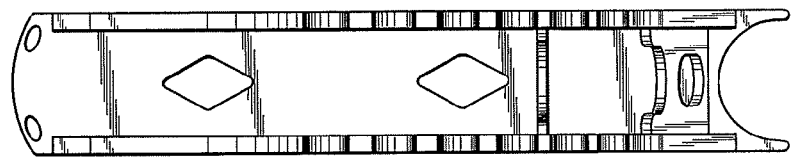
FIG. 2
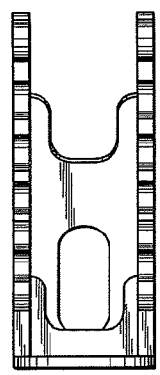
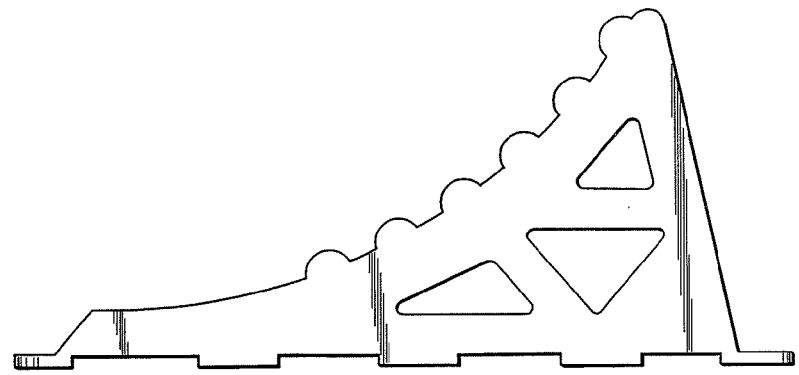
FIG. 4     FIG. 3

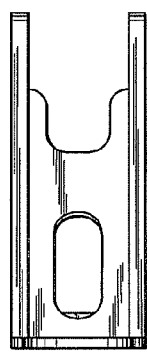 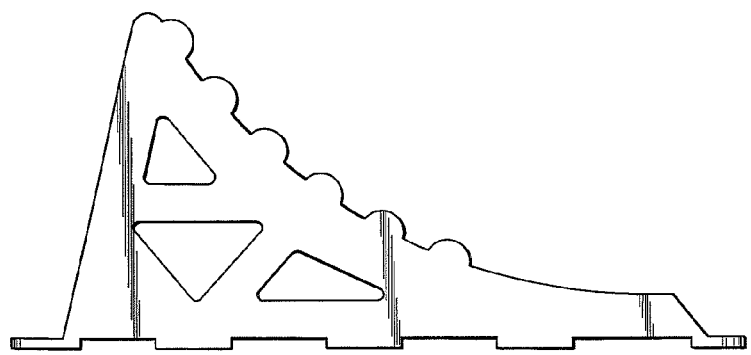 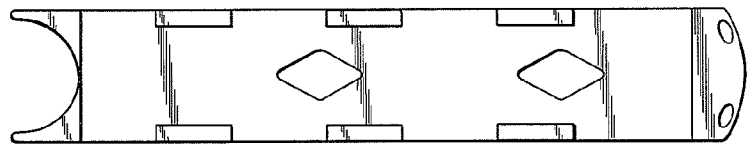
FIG. 5     FIG. 6
FIG. 7

BENZYLBENZENE DERIVATIVES AND METHODS OF USE

CROSS-REFERENCE TO RELATED APPLICATION

This application is a continuation of U.S. application Ser. No. 12/197,095 (now U.S. Pat. No. 7,838,499), filed Aug. 22, 2008, which claims priority to U.S. Provisional Application No. 60/957,625, filed Aug. 23, 2007, which are incorporated in their entirety herein for all purposes.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

According to the World Health Organization, approximately 150 million people worldwide have diabetes mellitus. The two principal forms of diabetes are type 1 diabetes, in which the pancreas fails to produce insulin, and type 2 diabetes, in which the body fails to respond properly to the insulin produced (insulin resistance). Accounting for about 90% of all diabetes cases, type 2 diabetes is by far the most common. In both types of diabetes, the absence of insulin action or proper response to insulin results in elevated levels of serum glucose (hyperglycemia). Serious complications associated with diabetes include retinopathy (leading to visual impairment or blindness), cardiovascular disease, nephropathy, neuropathy, ulcers and diabetic foot disease.

Individuals with type 1 diabetes currently require insulin therapy. While in many cases type 2 diabetes can be managed with diet and exercise, drug intervention also frequently is required. Besides insulin, which is needed by about one-third of patients with type 2 diabetes, current antidiabetic therapies include biguanides (which decrease glucose production in the liver and increase sensitivity to insulin), sulfonylureas and meglitinides (which stimulate insulin production), alpha-glucosidase inhibitors (which slow starch absorption and glucose production), and thiazolidinediones (which increase insulin sensitivity). These medicines are often used in combination, and even then may not provide adequate glycemic control or may produce undesired side effects. Such side effects include lactic acidosis (biguanides), hypoglycemia (sulfonylureas), and edema and weight gain (thiazolidinediones). Therefore, new antidiabetic agents providing improved glycemic control and lacking these adverse effects are highly desired.

One promising target for therapeutic intervention in diabetes and related disorders is the glucose transport system of the kidneys. Cellular glucose transport is conducted by either facilitative ("passive") glucose transporters (GLUTs) or sodium-dependent ("active") glucose cotransporters (SGLTs). SGLT1 is found predominantly in the intestinal brush border, while SGLT2 is localized in the renal proximal tubule and is reportedly responsible for the majority of glucose reuptake by the kidneys. Recent studies suggest that inhibition of renal SGLT may be a useful approach to treating hyperglycemia by increasing the amount of glucose excreted in the urine (Arakawa K, et al., Br J Pharmacol 132:578-86, 2001; Oku A, et al., Diabetes 48:1794-1800, 1999). The potential of this therapeutic approach is further supported by recent findings that mutations in the SGLT2 gene occur in cases of familial renal glucosuria, an apparently benign syndrome characterized by urinary glucose excretion in the presence of normal serum glucose levels and the absence of general renal dysfunction or other disease (Santer R, et al., J Am Soc Nephrol 14:2873-82, 2003). Therefore, compounds which inhibit SGLT, particularly SGLT2, are promising candidates for use as antidiabetic drugs. Compounds previously described as useful for inhibiting SGLT include C-glycoside derivatives (such as those described in U.S. Pat. No. 6,414, 126, US20040138439, US20050209166, US20050233988, WO2005085237, U.S. Pat. No. 7,094,763, US20060009400, US20060019948, US20060035841, US20060122126, US20060234953, WO2006108842, US20070049537 and WO2007136116), O-glycoside derivatives (such as those described in U.S. Pat. No. 6,683,056, US20050187168, US20060166899, US20060234954, US20060247179 and US20070185197), spiroketal-glycoside derivatives (described in WO2006080421), cyclohexane derivatives (such as those described in WO2006011469), and thio-glucopyranoside derivatives (such as those described in US20050209309 and WO2006073197).

BRIEF SUMMARY OF THE INVENTION

The present invention provides compounds having an inhibitory effect on sodium-dependent glucose cotransporter SGLT. The invention also provides pharmaceutical compositions, methods of preparing the compounds, synthetic intermediates, and methods of using the compounds, independently or in combination with other therapeutic agents, for treating diseases and conditions which are affected by SGLT inhibition.

BRIEF DESCRIPTION OF THE DRAWINGS

FIG. 1 is the general synthesis method of Scheme I for the preparation of compounds of the invention.

FIG. 2 is the general synthesis method of Scheme II for the preparation of compounds of the invention.

FIG. 3 is the general synthesis method of Scheme III for the preparation of compounds of the invention.

FIG. 4 is the outline for the preparation of intermediate D.

FIG. 5 is the outline for the synthesis of compounds E and F of the invention.

FIG. 6 is the outline for the synthesis of compound G of the invention.

FIG. 7 is the outline for the synthesis of compounds K and L of the invention.

DETAILED DESCRIPTION OF THE INVENTION

Definitions

Figure 8:
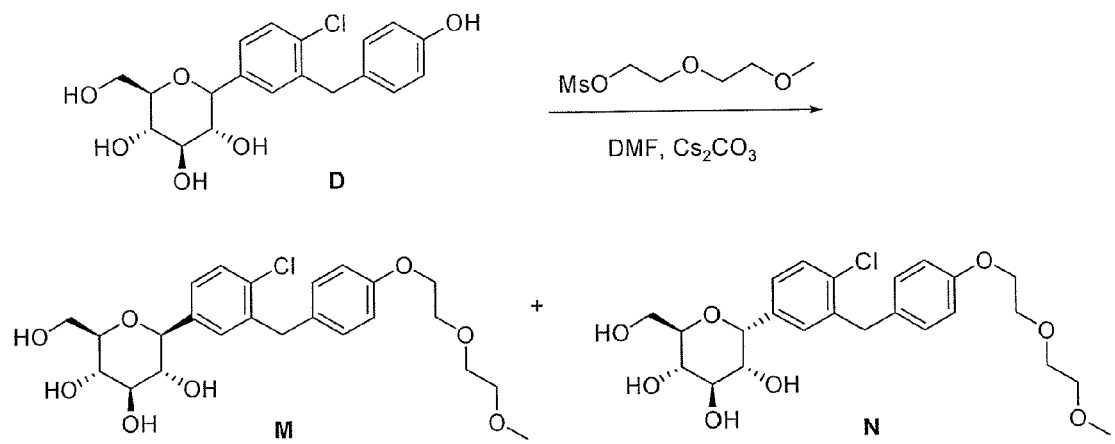
FIG. 8 is the outline for the synthesis of compounds M and N of the invention.

As used herein, the term "halo" means a monovalent halogen radical or atom selected from fluoro, chloro, bromo and iodo. Preferred halo groups are fluoro, chloro and bromo.

As used herein, the term "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents may be selected from the group consisting of halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl)$C_1$-$C_6$ alkoxy, $C_3$-$C_7$ heterocycloalkyl, ($C_3$-$C_7$ heterocycloalkyl)$C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxy, hydroxy, carboxy, oxo, sulfanyl, $C_1$-$C_6$ alkylsulfanyl, aryl, heteroaryl, aryloxy, heteroaryloxy, aralkyl, heteroaralkyl, aralkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, unless otherwise indicated, the term "alkyl" alone or in combination refers to a monovalent saturated aliphatic hydrocarbon radical having the indicated number of carbon atoms. The radical may be a linear or branched chain and, where specified, optionally substituted with one to three suitable substituents as defined above. Illustrative examples of alkyl groups include, but are not limited to, methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, n-dodecyl, n-tetradecyl, n-hexadecyl, n-octadecyl, n-eicosyl and the like. Preferred alkyl groups include methyl, ethyl, n-propyl and isopropyl. Preferred optional suitable substituents include halo, methoxy, ethoxy, cyano, nitro and amino.

As used herein, unless otherwise indicated, the term "alkenyl" alone or in combination refers to a monovalent aliphatic hydrocarbon radical having the indicated number of carbon atoms and at least one carbon-carbon double bond. The radical may be a linear or branched chain, in the E or Z form, and where specified, optionally substituted with one to three suitable substituents as defined above. Illustrative examples of alkenyl groups include, but are not limited to, vinyl, 1-propenyl, 2-propenyl, isopropenyl, 1-butenyl, 2-butenyl, isobutenyl, 2-methyl-1-propenyl, 1-pentenyl, 2-pentenyl, 4-methyl-2-pentenyl, 1,3-pentadienyl, 2,4-pentadienyl, 1,3-butadienyl and the like. Preferred alkenyl groups include vinyl, 1-propenyl and 2-propenyl. Preferred optional suitable substituents include halo, methoxy, ethoxy, cyano, nitro and amino.

As used herein, unless otherwise indicated, the term "alkynyl" alone or in combination refers to a monovalent aliphatic hydrocarbon radical having the indicated number of carbon atoms and at least one carbon-carbon triple bond. The radical may be a linear or branched chain and, where specified, optionally substituted with one to three suitable substituents as defined above. Illustrative examples of alkynyl groups include, but are not limited to, ethynyl, 1-propynyl, 2-propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like. Preferred alkynyl groups include ethynyl, 1-propynyl and 2-propynyl. Preferred optional suitable substituents include halo, methoxy, ethoxy, cyano, nitro and amino.

As used herein, unless otherwise indicated, the term "cycloalkyl" alone or in combination refers to a monovalent alicyclic saturated hydrocarbon radical having three or more carbons forming a carbocyclic ring and, where specified, optionally substituted with one to three suitable substituents as defined above. Illustrative examples of cycloalkyl groups include, but are not limited to, cyclopropyl, cyclobutyl, cyclopentyl, cyclohexyl, cycloheptyl, cyclooctyl, cyclononyl and the like. Preferred optional suitable substituents include halo, methyl, ethyl, methoxy, ethoxy, cyano, nitro and amino.

As used herein, unless otherwise indicated, the term "cycloalkenyl" alone or in combination refers to a monovalent alicyclic hydrocarbon radical having three or more carbons fanning a carbocyclic ring and at least one carbon-carbon double bond and, where specified, optionally substituted with one to three suitable substituents as defined above.

Illustrative examples of cycloalkenyl groups include, but are not limited to, cyclopentenyl, cyclohexenyl and the like. Preferred optional suitable substituents include halo, methyl, ethyl, methoxy, ethoxy, cyano, nitro and amino.

As used herein, unless otherwise indicated, the terms "alkylene", "alkenylene", "cycloalkylene" and "cycloalkenylene" refer to a divalent hydrocarbon radical that is formed by removal of a hydrogen atom from an alkyl, alkenyl, cycloalkyl or cycloalkenyl radical, respectively, as such terms are defined above.

As used herein, the term "($C_3$-$C_{10}$ cycloalkylene)($C_1$-$C_6$ alkylene)" refers to a divalent hydrocarbon radical that is formed by bonding a $C_3$-$C_{10}$ cycloalkylene radical with $C_1$-$C_6$ alkylene radical, as such terms are defined above.

As used herein, unless otherwise indicated, the term "aryl" alone or in combination refers to a monovalent aromatic hydrocarbon radical having six to ten carbon atoms forming a carbocyclic ring and, where specified, optionally substituted with one to three suitable substituents as defined above. Illustrative examples of aryl groups include, but are not limited to, phenyl, naphthyl, tetrahydronaphthyl, indanyl and the like. Preferred aryl groups are phenyl and naphthyl, optionally mono- or disubstituted by identical or different suitable substituents selected from halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

As used herein, unless otherwise indicated, the term "heterocycloalkyl" alone or in combination refers to a cycloalkyl group as defined above in which one or more carbons in the ring is replaced by a heteroatom selected from N, S and O. Illustrative examples of heterocycloalkyl groups include, but are not limited to, pyrrolidinyl, tetrahydrofuranyl, piperazinyl, tetrahydropyranyl, and the like.

As used herein, unless otherwise indicated, the term "heteroaryl" alone or in combination refers to a monovalent aromatic heterocyclic radical having two to nine carbons and one to four heteroatoms selected from N, S and O forming a five- to ten-membered monocyclic or fused bicyclic ring and, where specified, optionally substituted with one to three suitable substituents as defined above. Illustrative examples of heteroaryl groups include, but are not limited to, pyridyl, pyridazinyl, pyrazinyl, pyrimidinyl, triazinyl, quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridines, benzothiaxolyl, benzofuranyl, benzothienyl, indolyl, isothiazolyl, pyrazolyl, indazolyl, imidazolyl, triazolyl, tetrazolyl, oxazolyl, isoxazolyl, oxadiazolyl, thiadiazolyl, pyrrolyl, thiazolyl, furyl, thienyl and the like. Five- or six-membered monocyclic heteroaryl rings include: pyridyl, pyridazinyl, pyrazinyl, pyrimidinyl, triazinyl, isothiazolyl, pyrazolyl, imidazolyl, triazolyl, tetrazolyl, oxazolyl, isoxazolyl, oxadiazolyl, thiadiazolyl, pyrrolyl, thiazolyl, furyl, thienyl and the like. Eight- to ten-membered bicyclic heteroaryl rings having one to four heteroatoms include: quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridinyl, benzothiaxolyl, benzofuranyl, benzothienyl, indolyl, indazolyl, and the like. Preferred optional suitable substitutions include one or two identical or different substituents selected from halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

As used herein, unless otherwise indicated, the terms "alkoxy" and "alkyloxy" alone or in combination refer to an aliphatic radical of the form alkyl-O—, wherein alkyl is as defined above. Illustrative examples of alkoxy groups include, but are not limited to, methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy, octoxy and the like. Preferred alkoxy groups include methoxy and ethoxy.

As used herein, unless otherwise indicated, the term "haloalkyl" refers to an alkyl radical as described above substituted with one or more halogens. Illustrative examples of haloalkyl groups include, but are not limited to, chloromethyl, dichloromethyl, fluoromethyl, difluoromethyl, trifluoromethyl, 2,2,2-trichloroethyl and the like.

As used herein, unless otherwise indicated, the term "haloalkoxy" refers to an alkoxy radical as described above substituted with one or more halogens. Illustrative examples of haloalkoxy groups include, but are not limited to, trifluoromethoxy, difluoromethoxy and the like.

As used herein, unless otherwise indicated, the term "aralkyl" refers to an alkyl radical of one to six carbons as described above substituted with an aryl group as described above.

As used herein, unless otherwise indicated, the term "heteroaralkyl" refers to an alkyl radical of one to six carbons as described above substituted with a heteroaryl group as described above.

As used herein, unless otherwise indicated, the term "aralkoxy" refers to an alkoxy radical of one to six carbons as described above substituted with an aryl group as described above.

As used herein, unless otherwise indicated, the term "heteroaralkoxy" refers to an alkoxy radical of one to six carbons as described above substituted with a heteroaryl group as described above.

As used herein, unless otherwise indicated, the term "carbamoyl" refers to a monovalent radical of the form —C(O)NH(R), wherein R is hydrogen, $C_1$-$C_6$ alkyl, $C_2$-$C_6$ alkenyl, $C_3$-$C_6$ cycloalkyl, or aryl as such terms are defined above.

As used herein, unless otherwise indicated, the terms "di-($C_1$-$C_3$ alkyl)amino" and "di-($C_1$-$C_6$ alkyl)amino" alone or in combination refer to an amino group that is substituted with two groups independently selected from $C_1$-$C_3$ alkyl or $C_1$-$C_6$ alkyl, respectively.

As used herein, the terms "treating" and "treatment" refer to delaying the onset of, retarding or reversing the progress of or alleviating or preventing either the disease or condition to which the term applies, or one or more symptoms of such disease or condition.

As used herein, the term "administering" means oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and the like.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound). A prodrug itself may either lack or possess the desired biological activity.

As used herein, the term "compound" refers to a molecule produced by any means including, without limitation, synthesis in vitro or generation in situ or in vivo.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terns are used interchangeably with "nonimmediate release" as defined in *Remington: The Science and Practice of Pharmacy*, $21^{st}$ Ed., Gennaro, Ed., Lippencott Williams & Wilkins (2003). As discussed therein, immediate and nonimmediate release can be defined kinetically by reference to the following equation:

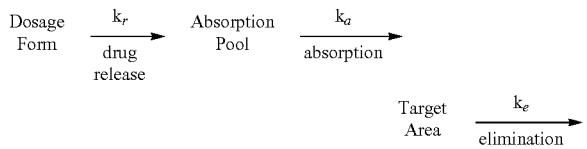

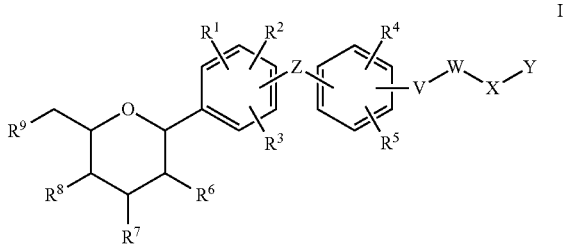

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area.

The terms "sustained release" and "extended release" are used in their conventional sense to refer to a drug formulation that provides for gradual release of a drug over an extended period of time, for example, 12 hours or more, and that preferably, although not necessarily, results in substantially constant blood levels of a drug over an extended time period.

As used herein, the term "delayed release" refers to a pharmaceutical preparation that passes through the stomach intact and dissolves in the small intestine.

General

The present invention provides compounds having an inhibitory effect on sodium-dependent glucose cotransporter SGLT, preferably SGLT2. Some compounds according to the present invention also have an inhibitory effect on sodium-dependent glucose cotransporter SGLT1. Owing to their ability to inhibit SGLT, the compounds of the present invention are suitable for the treatment and/or prevention of any and all conditions and diseases that are affected by inhibition of SGLT activity, particularly SGLT2 activity. Therefore, the compounds of the present invention are suitable for the prevention and treatment of diseases and conditions, particularly metabolic disorders, including but not limited to type 1 and type 2 diabetes mellitus, hyperglycemia, diabetic complications (such as retinopathy, nephropathy [e.g., progressive renal disease], neuropathy, ulcers, micro- and macroangiopathies, and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases.

The present invention also provides pharmaceutically acceptable salts and prodrugs of compounds according to the present invention.

The present invention further provides pharmaceutical compositions comprising an effective amount of a compound or mixture of compounds according to the present invention, or a pharmaceutically acceptable salt or prodrug thereof, in a pharmaceutically acceptable carrier.

The present invention further provides synthetic intermediates and processes for preparing the compounds of the present invention.

The present invention also provides methods of using the compounds according to the present invention, independently or in combination with other therapeutic agents, for treating diseases and conditions which may be affected by SGLT inhibition.

The present invention also provides methods of using the compounds according to the present invention for the preparation of a medicament for treating diseases and conditions which may be affected by SGLT inhibition.

Detailed Embodiments

Compounds and Preparative Methods

In one aspect, the present invention provides for compounds of Formula I:

wherein

V represents oxygen; sulfur; SO; $SO_2$; or a single bond;

W represents $C_1$-$C_6$ alkylene, $C_2$-$C_6$ alkenylene, $C_2$-$C_6$ alkynylene, $C_3$-$C_{10}$ cycloalkylene, $C_5$-$C_{10}$ cycloalkenylene, or ($C_3$-$C_{10}$ cycloalkylene)($C_1$-$C_6$ alkylene) where the $C_3$-$C_{10}$ cycloalkylene portion bonds to V and the $C_1$-$C_6$ alkylene portion bonds to X, and wherein alkylene, alkenylene, alkynylene, cycloalkylene and cycloalkenylene groups or portions optionally may be partly or completely fluorinated and may be mono- or disubstituted by identical or different substituents selected from chlorine, hydroxy, $C_1$-$C_3$ alkyl, $C_1$-$C_3$ alkoxy, $C_3$-$C_6$ cycloalkyl, $C_3$-$C_6$ cycloalkyloxy, $C_5$-$C_{10}$ cycloalkenyl or $C_5$-$C_{10}$ cycloalkenyloxy, and in cycloalkylene and cycloalkenylene groups or portions one or two methylene groups are optionally replaced independently of one another by O, S, CO, SO, $SO_2$ or $NR^b$, and one or two methyne groups are optionally replaced by N;

X represents oxygen; sulfur; SO; or $SO_2$;

Y represents hydrogen, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_{10}$ cycloalkyl, $C_5$-$C_{10}$ cycloalkenyl, ($C_3$-$C_{10}$ cycloalkyl)$C_1$-$C_4$ alkyl, ($C_5$-$C_{10}$ cycloalkenyl)$C_1$-$C_3$ alkyl, ($C_3$-$C_{10}$ cycloalkyl)$C_2$-$C_4$ alkenyl, $C_3$-$C_6$ cycloalkylidenmethyl, ($C_5$-$C_{10}$ cycloalkenyl)$C_2$-$C_4$ alkenyl, ($C_1$-$C_4$ alkyloxy)$C_1$-$C_3$ alkyl, ($C_2$-$C_4$ alkenyloxy)$C_1$-$C_3$ alkyl, ($C_3$-$C_{10}$ cycloalkyloxy)$C_1$-$C_3$ alkyl, ($C_5$-$C_{10}$ cycloalkenyloxy)$C_1$-$C_3$ alkyl, (amino)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_1$-$C_6$ alkyl)carbonyl($C_1$-$C_3$)alkyl, ($C_2$-$C_6$ alkenyl)carbonyl($C_1$-$C_3$)alkyl, ($C_2$-$C_6$ alkynyl)carbonyl($C_1$-$C_3$)alkyl, (arylcarbonyl)$C_1$-$C_3$ alkyl, (heteroarylcarbonyl)$C_1$-$C_3$ alkyl, ($C_1$-$C_6$ alkylsulfonyl)$C_1$-$C_3$ alkyl, ($C_2$-$C_6$ alkenylsulfonyl)$C_1$-$C_3$ alkyl, ($C_2$-$C_6$ alkynylsulfonyl)$C_1$-$C_3$ alkyl, (arylsulfonyl)$C_1$-$C_3$ alkyl, (heteroarylsulfonyl)$C_1$-$C_3$ alkyl, ($C_1$-$C_6$ alkyl)aminocarbonyl($C_1$-$C_3$)alkyl, ($C_2$-$C_6$ alkenyl)aminocarbonyl($C_1$-$C_3$)alkyl, ($C_2$-$C_6$ alkynyl)aminocarbonyl($C_1$-$C_3$)alkyl, (arylaminocarbonyl)$C_1$-$C_3$ alkyl, (heteroarylaminocarbonyl)$C_1$-$C_3$ alkyl, ($C_1$-$C_6$ alkyl)carbonyl, ($C_2$-$C_6$ alkenyl)carbonyl, ($C_2$-$C_6$ alkynyl)carbonyl, arylcarbonyl, heteroarylcarbonyl, ($C_1$-$C_6$ alkyl)sulfonyl, ($C_2$-$C_6$ alkenyl)sulfonyl, ($C_2$-$C_6$ alkynyl)sulfonyl, arylsulfonyl or heteroarylsulfonyl;

wherein alkyl, alkenyl, alkynyl, cycloalkyl and cycloalkenyl groups or portions optionally may be partly or completely fluorinated and may be mono- or disubstituted by identical or different substituents selected from chlorine, hydroxy, $C_1$-$C_3$ alkyl, $C_1$-$C_3$ alkoxy, $C_3$-$C_6$ cycloalkyl, $C_3$-$C_6$ cycloalkyloxy, $C_5$-$C_{10}$ cycloalkenyl, $C_5$-$C_{10}$ cycloalkenyloxy, and $NR^bR^c$, and in cycloalkyl and cycloalkenyl groups or portions one or two methylene groups are optionally replaced independently of one another by O, S, CO, SO, $SO_2$ or $NR^b$, and one or two methyne groups are optionally replaced by N, wherein the heterocycle formed by said optional replacement is other than heteroaryl, and wherein when V represents oxygen, sulfur or a single bond and W represents $C_1$-$C_6$ alkylene, then Y is other than hydrogen, $C_1$-$C_6$ alkyl or ($C_3$-$C_{10}$ cycloalkyl)$C_1$-$C_4$ alkyl, and when V represents oxygen, W represents $C_3$-$C_{10}$ cycloalkylene and X represents oxygen, then Y is other than hydrogen, $C_1$-$C_6$ alkyl, or trifluoromethyl, and when V represents a single bond and W represents $C_2$-$C_6$ alkenylene, $C_2$-$C_6$ alkynylene, $C_3$-$C_{10}$ cycloalkylene or $C_5$-$C_{10}$ cycloalkenylene, then Y is other than hydrogen, $C_1$-$C_6$ alkyl or ($C_3$-$C_{10}$ cycloalkyl)$C_1$-$C_4$ alkyl;

and when V represents oxygen, sulfur, SO or $SO_2$, W represents $C_2$-$C_6$ alkenylene or $C_2$-$C_6$ alkynylene, and Y represents $C_3$-$C_{10}$ cycloalkyl or $C_5$-$C_{10}$ cycloalkenyl, then X may also represent a single bond;

or X represents $NR^a$ and Y represents $C_1$-$C_6$ alkylsulfonyl, $C_2$-$C_6$ alkenylsulfonyl, $C_2$-$C_6$ alkynylsulfonyl, arylsulfonyl, heteroarylsulfonyl, $C_1$-$C_6$ alkylsulfinyl, arylsulfinyl, heteroarylsulfinyl, ($C_1$-$C_6$ alkyl)carbonyl, ($C_2$-$C_6$ alkenyl)carbonyl, ($C_2$-$C_6$ alkynyl)carbonyl, arylcarbonyl, heteroarylcarbonyl, ($C_1$-$C_6$ alkyl)aminocarbonyl, ($C_2$-$C_6$ alkenyl)aminocarbonyl, ($C_2$-$C_6$ alkynyl)aminocarbonyl, arylaminocarbonyl, heteroarylaminocarbonyl, ($C_1$-$C_6$ alkylsulfonyl)$C_1$-$C_3$ alkyl, ($C_2$-$C_6$ alkenylsulfonyl)$C_1$-$C_3$ alkyl, ($C_2$-$C_6$ alkynylsulfonyl)$C_1$-$C_3$ alkyl, (arylsulfonyl)$C_1$-$C_3$ alkyl, (heteroarylsulfonyl)$C_1$-$C_3$ alkyl, ($C_1$-$C_6$ alkylsulfinyl)$C_1$-$C_3$ alkyl, (arylsulfinyl)$C_1$-$C_3$ alkyl, (heteroarylsulfinyl)$C_1$-$C_3$ alkyl, ($C_1$-$C_6$ alkyl)aminocarbonyl($C_1$-$C_3$)alkyl, ($C_2$-$C_6$ alkenyl)aminocarbonyl($C_1$-$C_3$)alkyl, ($C_2$-$C_6$ alkynyl)aminocarbonyl($C_1$-$C_3$)alkyl, (arylaminocarbonyl)$C_1$-$C_3$ alkyl or (heteroarylaminocarbonyl)$C_1$-$C_3$ alkyl;

wherein alkyl, alkenyl and alkynyl portions may be partly or completely fluorinated, and when $R^a$ represents H or ($C_1$-$C_4$ alkyl)carbonyl, then Y is other than ($C_1$-$C_6$ alkyl)carbonyl or arylcarbonyl;

Z represents oxygen; sulfur; SO; $SO_2$; 1,1-cyclopropylene; carbonyl; or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy;

$R^1$, $R^2$ and $R^3$ each independently represent hydrogen, halo, hydroxy, $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_6$ alkyloxy, $C_3$-$C_{10}$ cycloalkyloxy, cyano or nitro, wherein alkyl and cycloalkyl groups or portions optionally may be mono- or polysubstituted by fluorine, or in the event that $R^1$ and $R^2$ are bound to two adjacent C atoms of the phenyl ring, $R^1$ and $R^2$ may be joined together such that $R^1$ and $R^2$ together form a $C_3$-$C_5$ alkylene, $C_3$-$C_5$ alkenylene or butadienylene bridge, which may be partly or completely fluorinated and may be mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^b$, and wherein one or two methyne groups optionally may be replaced by N;

$R^4$ and $R^5$ each independently represent hydrogen, halo, cyano, nitro, hydroxy, $C_1$-$C_6$ alkyl, $C_3$-$C_{10}$ cycloalkyl, $C_1$-$C_3$ alkyloxy or $C_3$-$C_{10}$ cycloalkyloxy, wherein alkyl and cycloalkyl groups or portions optionally may be mono- or polysubstituted by fluorine, or if $R^4$ and $R^5$ are bound to two adjacent C atoms of the phenyl ring, $R^4$ and $R^5$ optionally may be joined together such that $R^4$ and $R^5$ together form a $C_3$-$C_5$ alkylene, $C_3$-$C_5$ alkenylene or butadienylene bridge, which may be partly or completely fluorinated and mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^b$, and wherein one or two methyne groups may be replaced by N;

$R^6$, $R^7$, $R^8$ and $R^9$ each independently represent hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, ($C_3$-$C_{10}$ cycloalkyl)carbonyloxy, hydrogen, halo, $C_1$-$C_6$ alkyl, $C_2$-$C_6$ alkenyl, $C_2$-$C_6$ alkynyl, ($C_3$-$C_{10}$)cycloalkyl-($C_1$-$C_3$)alkyl, ($C_5$-$C_7$)cycloalkenyl-($C_1$-$C_3$)alkyl, aryl-($C_1$-$C_3$)alkyl, heteroaryl-($C_1$-$C_3$)alkyl, $C_1$-$C_6$ alkyloxy, $C_2$-$C_6$ alkenyloxy, $C_2$-$C_6$ alkynyloxy, $C_3$-$C_7$ cycloalkyloxy, $C_5$-$C_7$ cycloalkenyloxy, aryloxy, heteroaryloxy, ($C_3$-$C_7$)cycloalkyl-($C_1$-$C_3$) alkyloxy, ($C_5$-$C_7$)cycloalkenyl-($C_1$-$C_3$)alkyloxy, aryl-($C_1$-$C_3$)alkyloxy, heteroaryl-($C_1$-$C_3$)alkyloxy, aminocarbonyl, hydroxycarbonyl, ($C_1$-$C_4$ alkyl)aminocarbonyl, di-($C_1$-$C_3$ alkyl)aminocarbonyl, ($C_1$-$C_4$ alkyloxy)carbonyl, aminocarbonyl-($C_1$-$C_3$)alkyl, ($C_1$-$C_4$ alkyl)aminocarbonyl-($C_1$-$C_3$) alkyl, di-($C_1$-$C_3$ alkyl)aminocarbonyl-($C_1$-$C_3$)alkyl, hydroxycarbonyl-($C_1$-$C_3$)alkyl, ($C_1$-$C_4$ alkyloxy)carbonyl-($C_1$-$C_3$)alkyl, ($C_3$-$C_7$)cycloalkyloxy-($C_1$-$C_3$)alkyl, ($C_5$-$C_7$) cycloalkenyloxy-($C_1$-$C_3$)alkyl, aryloxy-($C_1$-$C_3$)alkyl, heteroaryloxy-($C_1$-$C_3$)alkyl, $C_1$-$C_4$ alkylsulfonyloxy, arylsulfonyloxy, aryl-($C_1$-$C_3$)alkyl-sulfonyloxy, sulfonyloxy, trimethylsilyloxy, t-butyldimethylsilyloxy, or cyano;

wherein alkyl, alkenyl, alkynyl, cycloalkyl and cycloalkenyl groups or portions optionally may be partly or completely fluorinated and may be mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^b$, O, S, CO, SO or $SO_2$, and when Y is hydrogen or $C_1$-$C_6$ alkyl, then both $R^8$ and $R^9$ are hydroxy;

$R^a$ independently represents H, $C_1$-$C_6$ alkyl, $C_3$-$C_6$ cycloalkyl or ($C_1$-$C_4$ alkyl)carbonyl, wherein alkyl and cycloalkyl groups or portions optionally may be partly or completely fluorinated;

$R^b$ independently represents H, $C_1$-$C_4$ alkyl or ($C_1$-$C_4$ alkyl)carbonyl, wherein alkyl groups or portions optionally may be partly or completely fluorinated;

$R^c$ independently represents H, $C_1$-$C_4$ alkyl, $C_3$-$C_6$ cycloalkyl, $CHR^dR^e$, $SO_2R^d$, $C(O)OR^d$ or $C(O)NR^dR^e$, wherein alkyl and cycloalkyl groups optionally may be partly or completely fluorinated; and $R^d$ and $R^e$ each independently represent H or $C_1$-$C_6$ alkyl, wherein alkyl groups optionally may be partly or completely fluorinated.

In another aspect, the present invention provides for compounds of Formula I, wherein the substituent groups are defined as above, except when V represents oxygen, sulfur or a single bond, and W represents $C_1$-$C_6$ alkylene, then Y may also represent ($C_3$-$C_{10}$ cycloalkyl)$C_1$-$C_4$ alkyl, wherein in the cycloalkyl portion of Y one or two methylene groups are replaced independently of one another by O, S, CO, SO, $SO_2$ or NR$^b$, and/or one or two methyne groups are replaced by N, wherein the heterocycle formed by said replacement is other than heteroaryl.

The style used above and hereinafter, in which a bond of a substituent on a phenyl group is shown ending near the center of the phenyl ring, denotes, unless otherwise stated, that this substituent may be bound to any free position of the phenyl group bearing a hydrogen atom.

The present invention includes all tautomers and stereoisomers of compounds of Formula I, either in admixture or in pure or substantially pure form. The compounds of the present invention can have asymmetric centers at the carbon atoms, and therefore the compounds of Formula I can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

The present invention also provides for the prodrugs of compounds of Formula I. Prodrugs of compounds of the invention include, but are not limited to, carboxylate esters, carbonate esters, hemi-esters, phosphorus esters, nitro esters, sulfate esters, sulfoxides, amides, carbamates, azo compounds, phosphamides, glycosides, ethers, acetals, and ketals. Prodrug esters and carbonates may be formed, for example, by reacting one or more hydroxyl groups of compounds of Formula I with alkyl, alkoxy or aryl substituted acylating reagents using methods known to those of skill in the art to produce methyl carbonates, acetates, benzoates, pivalates and the like. Illustrative examples of prodrug esters of the compounds of the present invention include, but are not limited to, compounds of Formula I having a carboxyl moiety wherein the free hydrogen is replaced by $C_1$-$C_4$ alkyl, $C_1$-$C_7$ alkanoyloxymethyl, 1-(($C_1$-$C_5$)alkanoyloxy)ethyl, 1-methyl-1-(($C_1$-$C_5$)alkanoyloxy)-ethyl, $C_1$-$C_5$ alkoxycarbonyloxymethyl, 1-(($C_1$-$C_5$)alkoxycarbonyloxy)ethyl, 1-methyl-1-(($C_1$-$C_5$)alkoxycarbonyloxy)ethyl, N—(($C_1$-$C_5$)alkoxycarbonyl) aminomethyl, 1-(N—(($C_1$-$C_5$)alkoxycarbonyl)amino)ethyl, 3-phthalidyl, 4-crotonolactonyl, gamma-butyrolacton-4-yl, di-N,N—($C_1$-$C_2$)alkylamino($C_2$-$C_3$)alkyl (e.g., beta-dimethylaminoethyl), carbamoyl-($C_1$-$C_2$)alkyl, N,N-di($C_1$-$C_2$) alkylcarbamoyl-($C_1$-$C_2$)alkyl and piperidino-, pyrrolidino- or morpholino($C_2$-$C_3$)alkyl. Oligopeptide modifications and biodegradable polymer derivatives (as described, for example, in Int. J. Pharm. 115, 61-67, 1995) are within the scope of the invention. Methods for selecting and preparing suitable prodrugs are provided, for example, in the following: T. Higuchi and V. Stella, "Prodrugs as Novel Delivery Systems,"Vol. 14, ACS Symposium Series, 1975; H. Bundgaard, "Design of Prodrugs," Elsevier, 1985; and "Bioreversible Carriers in Drug Design," ed. Edward Roche, American Pharmaceutical Association and Pergamon Press, 1987.

The present invention also provides for the pharmaceutically acceptable salts of compounds of Formula I and prodrugs thereof. The acids that can be used as reagents to prepare the pharmaceutically acceptable acid addition salts of the basic compounds of this invention are those which form non-toxic acid addition salts, i.e., salts containing pharmacologically acceptable anions (such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (1,1'-methylene-2-hydroxy-3-naphthoate) salts). The bases that can be used as reagents to prepare the pharmaceutically acceptable base salts of the acidic compounds of the present invention are those that form non-toxic base salts with such compounds, including, but not limited to, those derived from pharmacologically acceptable cations such as alkali metal cations (e.g., potassium, lithium and sodium) and alkaline earth metal cations (e.g., calcium and magnesium), ammonium or water-soluble amine addition salts such as N-methylglucamine methylglucamine (meglumine), and the lower alkanolammonium and other base salts of pharmaceutically acceptable organic amines (e.g., methylamine, ethylamine, propylamine, dimethylamine, triethanolamine, diethylamine, t-butylamine, t-octylamine, trimethylamine, triethylamine, ethylenediamine, hydroxyethylamine, morpholine, piperazine, dehydroabietylamine, lysine and guanidine).

The present invention also includes isotopically-labeled compounds of Formula I, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^2$H, $^3$H, $^{13}$C, $^{14}$C, $^{15}$N, $^{18}$O, $^{17}$O, $^{18}$F, $^{35}$S and $^{36}$Cl). Isotopically-labeled compounds of Formula I and prodrugs thereof, as well as isotopically-labeled, pharmaceutically acceptable salts of compounds of Formula I and prodrugs thereof, are within the scope of the present invention. Isotopically-labeled compounds of the present invention are useful in assays of the tissue distribution of the compounds and their prodrugs and metabolites; preferred isotopes for such assays include $^3$H and $^{14}$C. In addition, in certain circumstances substitution with heavier isotopes, such as deuterium ($^2$H), can provide increased metabolic stability, which offers therapeutic advantages such as increased in vivo half-life or reduced dosage requirements. Isotopically-labeled compounds of this invention and prodrugs thereof can generally be prepared according to the methods described herein by substituting an isotopically-labeled reagent for a non-isotopically labeled reagent.

Optionally, the compounds of Formula I may be reacted with a complex forming reagent, such as the D or L enantiomer of a natural amino acid, in a suitable solvent to form the corresponding crystalline complex, such as the amino acid complex, of the compound of Formula I. Amino acid complexes of compounds of Formula I may be formed by mixing an amino acid with the purified compound in a suitable solvent or with a crude reaction mixture containing the compound and other reagents.

In preferred embodiments, V represents oxygen, sulfur, or a single bond. In particularly preferred embodiments, V represents oxygen or a single bond.

In preferred embodiments, W represents $C_1$-$C_6$ alkylene, $C_2$-$C_6$ alkenylene, $C_2$-$C_6$ alkynylene, $C_3$-$C_{10}$ cycloalkylene, or ($C_3$-$C_{10}$ cycloalkylene)($C_1$-$C_6$ alkylene). In particularly preferred embodiments, W represents $C_1$-$C_6$ alkylene, $C_2$-$C_6$ alkenylene, or $C_2$-$C_6$ alkynylene.

In preferred embodiments, X represents oxygen, sulfur, a single bond, or NR$^a$. In particularly preferred embodiments, X represents oxygen or a single bond.

In preferred embodiments, Y represents hydrogen, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_4$ alkyl, ($C_1$-$C_4$ alkyloxy)$C_1$-$C_3$ alkyl, ($C_3$-$C_{10}$ cycloalkyloxy)

$C_1$-$C_3$ alkyl, (amino)$C_1$-$C_3$ alkyl, ($C_1$-$C_4$ alkylamino)$C_1$-$C_3$ alkyl, ($C_1$-$C_6$ alkyl)carbonyl, ($C_2$-$C_6$ alkenyl)carbonyl, ($C_2$-$C_6$ alkynyl)carbonyl, ($C_1$-$C_6$ alkyl)sulfonyl, ($C_2$-$C_6$ alkenyl)sulfonyl, or ($C_2$-$C_6$ alkynyl)sulfonyl, wherein alkyl, alkenyl, alkynyl and cycloalkyl groups or portions optionally may be partly or completely fluorinated and may be mono- or disubstituted by identical or different substituents selected from chlorine, hydroxy, $C_1$-$C_3$ alkyl, $C_1$-$C_3$ alkoxy, and $C_3$-$C_6$ cycloalkyl, and in cycloalkyl groups or portions one or two methylene groups are optionally replaced independently of one another by O, S, CO, SO, $SO_2$ or $NR^b$, and one or two methyne groups are optionally replaced by N. In particularly preferred embodiments, Y represents hydrogen, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, or ($C_1$-$C_4$ alkyloxy)$C_1$-$C_3$ alkyl.

In preferred embodiments, Z represents oxygen, sulfur, or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy. In particularly preferred embodiments, Z represents methylene.

In preferred embodiments, $R^1$, $R^2$ and $R^3$ each independently represent hydrogen, halo, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, or cyano. In particularly preferred embodiments, $R^1$, $R^2$ and $R^3$ each independently represent hydrogen, halo or $C_1$-$C_6$ alkyl. In more particularly preferred embodiments, $R^1$ represents hydrogen, halo or $C_1$-$C_6$ alkyl and $R^2$ and $R^3$ both represent hydrogen.

In preferred embodiments, $R^4$ and $R^5$ each independently represent hydrogen, halo, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, or cyano. In particularly preferred embodiments, $R^4$ and $R^5$ each independently represent hydrogen, halo or $C_1$-$C_6$ alkyl. In more particularly preferred embodiments, $R^4$ and $R^5$ both represent hydrogen.

In preferred embodiments, $R^6$, $R^7$, $R^8$ and $R^9$ each independently represent hydroxy, halo, $C_1$-$C_6$ alkyl, $C_1$-$C_6$ alkyloxy, ($C_3$-$C_7$)cycloalkyloxy, aryloxy or ($C_3$-$C_7$)cycloalkyl-($C_1$-$C_3$)alkyloxy, wherein alkyl and cycloalkyl groups or portions may be partly or completely fluorinated. In particularly preferred embodiments, $R^6$, $R^7$, $R^8$ and $R^9$ each represent hydroxy.

As noted above, Formula IA represents still other preferred embodiments:

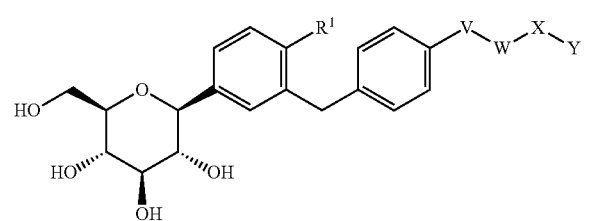

IA wherein $R^1$ represents hydrogen, halo or $C_1$-$C_6$ alkyl; V represents oxygen or a single bond; W represents $C_1$-$C_6$ alkylene, $C_2$-$C_6$ alkenylene, $C_2$-$C_6$ alkynylene, $C_3$-$C_{10}$ cycloalkylene, or ($C_3$-$C_{10}$ cycloalkylene)($C_1$-$C_6$ alkylene); X represents oxygen, a single bond, or $NR^a$; and Y represents hydrogen, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_4$ alkyl, ($C_1$-$C_4$ alkyloxy)$C_1$-$C_3$ alkyl, ($C_3$-$C_{10}$ cycloalkyloxy)$C_1$-$C_3$ alkyl, (amino)$C_1$-$C_3$ alkyl, ($C_1$-$C_4$ alkylamino)$C_1$-$C_3$ alkyl, ($C_1$-$C_6$ alkyl)carbonyl, ($C_2$-$C_6$ alkenyl)carbonyl, ($C_2$-$C_6$ alkynyl)carbonyl, ($C_1$-$C_6$ alkyl)sulfonyl, ($C_2$-$C_6$ alkenyl)sulfonyl, or ($C_2$-$C_6$ alkynyl)sulfonyl, wherein alkyl, alkenyl, alkynyl and cycloalkyl groups or portions optionally may be partly or completely fluorinated and may be mono- or disubstituted by identical or different substituents selected from chlorine, hydroxy, $C_1$-$C_3$ alkyl, $C_1$-$C_3$ alkoxy, and $C_3$-$C_6$ cycloalkyl, and in cycloalkyl groups or portions one or two methylene groups are optionally replaced independently of one another by O, S, CO, SO, $SO_2$ or $NR^b$, and one or two methyne groups are optionally replaced by N.

In another aspect, the present invention includes the compounds of Formula I and pharmaceutically acceptable salts, prodrugs and/or isotopically labeled compounds thereof, wherein alkyl, alkenyl, alkynyl, cycloalkyl, cycloalkenyl, aryl and heteroaryl groups or portions are optionally substituted with one to three suitable substituents as defined above.

In other aspects, the present invention provides intermediates and processes useful for preparing the intermediates below as well as the compounds of Formula I, and pharmaceutically acceptable salts and prodrugs thereof.

Such processes are outlined in the following general preparative methods depicted in Schemes I-III (FIGS. 1-3), with more detailed particular examples being presented below in the experimental section describing the working examples. By following the general preparative methods discussed below, or employing variations or alternative methods, the compounds of the invention can be readily prepared by the use of chemical reactions and procedures known to those of skill in the art. Unless otherwise specified, the variables (e.g., R groups) denoting groups in the general methods described below have the meanings as hereinbefore defined.

Those of skill in the art will recognize that compounds of the invention with each described functional group are generally prepared using slight variations of the below-listed general methods. Within the scope of each method, functional groups which are suitable to the reaction conditions are used. Functional groups which might interfere with certain reactions are presented in protected fauns where necessary, and the removal of such protective groups is completed at appropriate stages by methods well known to those skilled in the art.

In certain cases compounds of the invention can be prepared from other compounds of the invention by elaboration, transformation, exchange and the like of the functional groups present. Such elaboration includes, but is not limited to, hydrolysis, reduction, oxidation, alkylation, acylation, esterification, amidation and dehydration. Such transformations can in some instances require the use of protecting groups by the methods disclosed in T. W. Greene and P. G. M. Wuts, *Protective Groups in Organic Synthesis*; Wiley: New York, (1999), and incorporated herein by reference. Such methods would be initiated after synthesis of the desired compound or at another place in the synthetic route that would be readily apparent to one skilled in the art.

In another aspect, the present invention provides for synthetic intermediates useful for preparing the compounds of Formula I, and pharmaceutically acceptable salts and prodrugs thereof, according to the general preparative methods discussed below and other processes known to those of skill in the art.

When the following abbreviations and acronyms are used throughout the disclosure, they have the following meanings: $Ac_2O$, acetic anhydride; AcOEt, ethyl acetate; AcOH, acetic acid; AIBN, azobis(isobutyronitrile); $AlBr_3$, aluminum bromide; $AlCl_3$, aluminum chloride; $BBr_3$, boron tribromide; $BF_3.Et_2O$, boron trifluoride etherate; n-BuLi, n-butyllithium; s-BuLi, s-butyllithium; t-BuLi, t-butyllithium; t-BuOK, potassium tert-butoxide; CaCl$_2$, calcium chloride; calc., calculated; CCl$_4$, carbon tetrachloride; CD$_3$OD, methanol-d$_4$; CDCl$_3$, chloroform-d; CF$_3$SO$_3$H, trifluoromethanesulfonic acid; CH$_2$Cl$_2$, methylene chloride; CH$_2$I$_2$, methylene iodide; CH$_3$CN, acetonitrile; (COCl)$_2$, oxalyl chloride; cod, 1,5-cyclooctadiene; Cs$_2$CO$_3$, cesium carbonate; DAST, (diethylamino)sulfur trifluoride; DCM, dichloromethane; DMAP, 4-dimethylaminopyridine; DMEM, Dulbecco's Modified Eagle Medium; DMF, N,N-dimethylformamide; DMP, Dess-Martin periodinane; DMSO, dimethylsulfoxide; EA, ethyl acetate; EDCI, 1-(3-dimethylaminopropyl)-3-ethylcarbodiimide hydrochloride; eq, equivalents; Et, ethyl; Et$_3$N, triethylamine; Et$_3$SiH, triethylsilane; Et$_3$SiO, triethylsilyloxy; EtOAc, ethyl acetate; EtOH, ethanol; FBS, fetal bovine serum; FSO$_2$CF$_2$CO$_2$H, 2,2-difluoro-2-(fluorosulfonyl)acetic acid; h, hour; H$_2$, hydrogen gas; H$_2$SO$_4$, sulfuric acid; Hepes, 4-(2-hydroxyethyl)-1-piperazineethanesulfonic acid; $^1$H NMR, proton nuclear magnetic resonance; HOBt, 1-hydroxybenzotriazole; HPLC, high performance liquid chromatography; K$_2$CO$_3$, potassium carbonate; K$_2$CrO$_7$, potassium dichromate; KN(TMS)$_2$, potassium bis(trimethylsilyl) amide; KOH, potassium hydroxide; LC-ESI-MS, liquid chromatography electrospray ionization mass spectrometry; LC-MS, liquid chromatography-mass spectroscopy; Lg, leaving group; LiOH.H$_2$O, lithium hydroxide monohydrate; Me, methyl; MeCN, acetonitrile; MeOH, methanol; MeSO$_3$H, methanesulfonic acid; Mg, magnesium; MgCl$_2$, magnesium chloride; min, minute; MS ESI, mass spectroscopy with electrospray ionization; MsOH, methanesulfonic acid; NaBH$_3$CN, sodium cyanoborohydride; NaH, sodium hydride; NaHCO$_3$, sodium bicarbonate; NaHSO$_3$, sodium bisulfite; NaOAc, sodium acetate; NaOH, sodium hydroxide; Na$_2$SO$_4$, sodium sulfate; NBS, N-bromosuccinimide; NCS, N-chlorosuccinimide; NH$_4$Cl, ammonium chloride; NIS, N-iodosuccinimide; O$_3$, ozone; Pd/C, palladium on carbon; PdCl$_2$, palladium (II) chloride; PE, petroleum ether; Ph, phenyl; Ph$_3$PCH$_3$I (or Ph$_3$PMeI), methyltriphenylphosphonium iodide; POCl$_3$, phosphorus oxychloride; PPh$_3$, triphenylphosphine; R$_f$, retention factor; SnBu$_3$, tributyltin; SOCl$_2$, thionyl chloride; TBAI, tetrabutylammonium iodide; TFA, trifluoroacetic acid; THF, tetrahydrofuran; TLC, thin layer chromatography; TMS, trimethylsilyl; TMSCN, trimethylsilyl cyanide; Tris, trishydroxymethylaminomethane (or 2-amino-2-(hydroxymethyl)propane-1,3-diol); TsCl, toluenesulfonyl chloride; TsOH, toluenesulfonic acid; ZnEt$_2$, diethyl zinc.

General Synthesis Method of Scheme I

Inventive compounds of formula 12 can be conveniently prepared according to the reaction sequences as shown in Scheme I (FIG. 1). Acid 1, which may be commercially available or prepared according to conventional methods known to those of skill in the art, is converted to acid chloride 2 by an acylation agent such as oxalyl chloride, SOCl$_2$, POCl$_3$ or the like. Intermediate 2 is reacted with alkoxybenzene 3 under conditions aided by Lewis acid, such as AlCl$_3$ or AlBr$_3$, to provide ketone 4. The ketone group of intermediate 4 is reduced to methylene with a reducing agent such as Et$_3$SiH in the present of a Lewis acid such as BF$_3$.Et$_2$O or TFA, and treatment with Lewis acid such as BBr$_3$ to give phenol 5. Intermediate 6 can be obtained by coupling with the electrophilic reagent Lg-W-X-Y, where Lg denotes a suitable leaving group, in the presence of base such as K$_2$CO$_3$, Cs$_2$CO$_3$, NaOH or the like.

Alternatively, acid 1 can be converted to Weinreb amide 7 by coupling with NHMe(OMe). Intermediate 4 can then be obtained by treatment of Weinreb amide 7 with intermediate 8, bearing a metal coupling reagent such as Grignard reagent.

Alternatively, intermediate 6 can also be obtained by coupling of Weinreb amide 7 with Grignard reagent 9, followed by reduction of the ketone group of product 10 with Et$_3$SiH in the presence a Lewis acid such as BF$_3$.Et$_2$O or TFA.

Intermediate 6 is condensed with ketone 11 after treatment with activating reagent, such as n-BuLi or t-BuOK, and then reduced with alkylsilane or other reductant in the presence of acid, such as TFA, MeSO$_3$H or BF$_3$.Et$_2$O, to generate the inventive compounds of formula 12.

General Synthesis Method of Scheme II

Inventive compounds of formula 12 can also be conveniently prepared according to a reaction sequence as shown in Scheme II (FIG. 2). The ketone group of intermediate 4 is reduced to methylene with a reducing agent such as Et$_3$SiH in the presence of a Lewis acid such as BF$_3$.Et$_2$O or TFA. Intermediate 13 is condensed with ketone 11 after treatment with activating reagent, such as n-BuLi or t-BuOK, and then reduced with alkylsilane or other reductant in the presence of acid, such as TFA, MeSO$_3$H or BF$_3$.Et$_2$O, to give the intermediate 14. Treatment of 14 with a Lewis acid such as BBr$_3$ gives phenol 15, and then coupling with the electrophilic reagent Lg-W-X-Y in the presence of base, such as K$_2$CO$_3$, Cs$_2$CO$_3$, NaOH or the like, gives the inventive compounds of formula 12.

General Synthesis Method of Scheme III

Inventive compounds of formula 12 can also be prepared according to a reaction sequence as shown in Scheme III (FIG. 3). Treatment of intermediate 16 with a base such as n-BuLi, s-BuLi or t-BuLi, or Mg in a solvent such as THF to form Grignard reagent, followed by addition to intermediate 11 and treatment of the corresponding product with Lewis acid such as Et$_3$SiH provides intermediate 17. Halogenation of 17 with NCS, NBS or NIS provides intermediate 18. Stille coupling of 9 with intermediate 18 gives inventive compounds of formula 12.

Pharmaceutical Compositions and Methods of Use

The present invention further provides a pharmaceutical composition comprising an effective amount of a compound or mixture of compounds of Formula I, or a pharmaceutically acceptable salt or prodrug thereof, in a pharmaceutically acceptable carrier.

A compound of this invention can be incorporated into a variety of formulations for therapeutic administration. More particularly, a compound of the present invention can be formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of a compound of the present invention can be achieved in various ways, including oral, buccal, parenteral, intravenous, intradermal (e.g., subcutaneous, intramuscular), transdermal, etc., administration. Moreover, the compound can be administered in a local rather than systemic manner, for example, in a depot or sustained release formulation.

Suitable formulations for use in the present invention are found in *Remington: The Science and Practice of Pharmacy*, 21$^{st}$ Ed., Gennaro, Ed., Lippencott Williams & Wilkins (2003), which is hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In one preferred embodiment, a compound of the present invention is prepared for delivery in a sustained-release, controlled release, extended-release, timed-release or delayed-release formulation, for example, in semipermeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering a compound of the present invention include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

For oral administration, a compound of the present invention can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. For injection, the compound can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, a compound of the invention can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010;

6,465,006; 6,379,696; 6,312,717 and 6,310,177, each of which are hereby incorporated herein by reference.

For buccal administration, the compositions can take the form of tablets or lozenges formulated in conventional manner.

In addition to the formulations described previously, a compound of the present invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The present invention also contemplates pharmaceutical compositions comprising the compounds of Formula I in admixture with an effective amount of other therapeutic agents as combination partners, particularly those used for treating diseases and conditions which can be affected by SGLT inhibition, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. An effective amount of the compound and/or combination partner will, of course, be dependent on the subject being treated, the severity of the affliction and the manner of administration. Determination of an effective amount is well within the capability of those skilled in the art, especially in light of the detailed disclosure provided herein. Generally, an efficacious or effective amount of a compound is determined by first administering a low dose or small amount, and then incrementally increasing the administered dose or dosages until a desired therapeutic effect is observed in the treated subject, with minimal or no toxic side effects. Applicable methods for determining an appropriate dose and dosing schedule for administration of the present invention are described, for example, in *Goodman and Gilman's The Pharmacological Basis of Therapeutics*, 11$^{th}$ Ed., Brunton, Lazo and Parker, Eds., McGraw-Hill (2006), and in *Remington: The Science and Practice of Pharmacy*, 21$^{st}$ Ed., Gennaro, Ed., Lippencott Williams & Wilkins (2003), both of which are hereby incorporated herein by reference.

The present invention further provides methods of using the compounds of Formula I for the prevention and treatment of disease. In one embodiment the invention provides a method of treating type 1 and type 2 diabetes mellitus, hyperglycemia, diabetic complications (such as retinopathy, nephropathy, neuropathy, ulcers, micro- and macroangiopathies, gout and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases, which comprises administering an effective amount of a compound or mixture of compounds of Formula I, or a pharmaceutically acceptable salt or prodrug thereof, to a subject in need thereof. In another embodiment the invention provides a method of using a compound or mixture of compounds of Formula I, or a pharmaceutically acceptable salt or prodrug thereof, for the preparation of a medicament for treating type 1 and type 2 diabetes mellitus, hyperglycemia, diabetic complications, insulin resistance, metabolic syndrome, hyperinsulinemia, hypertension, hyperuricemia, obesity, edema, dyslipidemia, chronic heart failure, atherosclerosis and related diseases.

The present invention also contemplates the use of the compounds of Formula I, or pharmaceutically acceptable salts or prodrugs thereof, in combination with other therapeutic agents, particularly those used for treating the above-mentioned diseases and conditions, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. Those skilled in the art will appreciate that other therapeutic agents discussed below can have multiple therapeutic uses and the listing of an agent in one particular category should not be construed to limit in any way its usefulness in combination therapy with compounds of the present invention.

Examples of antidiabetic agents suitable for use in combination with compounds of the present invention include insulin and insulin mimetics, sulfonylureas (such as acetohexamide, carbutamide, chlorpropamide, glibenclamide, glibornuride, gliclazide, glimepiride, glipizide, gliquidone, glisoxepide, glyburide, glyclopyramide, tolazamide, tolcyclamide, tolbutamide and the like), insulin secretion enhancers (such as JTT-608, glybuzole and the like), biguanides (such as metformin, buformin, phenformin and the like), sulfonylurea/biguanide combinations (such as glyburide/metformin and the like), meglitinides (such as repaglinide, nateglinide, mitiglinide and the like), thiazolidinediones (such as rosiglitazone, pioglitazone, isaglitazone, netoglitazone, rivoglitazone, balaglitazone, darglitazone, CLX-0921 and the like), thiazolidinedione/biguanide combinations (such as pioglitazone/metformin and the like), oxadiazolidinediones (such as YM440 and the like), peroxisome proliferator-activated receptor (PPAR)-gamma agonists (such as farglitazar, metaglidasen, MBX-2044, GI 262570, GW1929, GW7845 and the like), PPAR-alpha/gamma dual agonists (such as muraglitazar, naveglitazar, tesaglitazar, peliglitazar, JTT-501, GW-409544, GW-501516 and the like), PPAR-alpha/gamma/delta pan agonists (such as PLX204, GlaxoSmithKline 625019, GlaxoSmithKline 677954 and the like), retinoid X receptor agonists (such as ALRT-268, AGN-4204, MX-6054, AGN-194204, LG-100754, bexarotene and the like), alpha-glucosidase inhibitors (such as acarbose, miglitol and the like), stimulants of insulin receptor tyrosine kinase (such as TER-17411, L-783281, KRX-613 and the like), tripeptidyl peptidase II inhibitors (such as UCL-1397 and the like), dipeptidyl peptidase IV inhibitors (such as sitagliptin, vildagliptin, denagliptin, saxagliptin, NVP-DPP728, P93/01, P32/98, FE 99901, TS-021, TSL-225, GRC8200, compounds described in U.S. Pat. Nos. 6,869,947; 6,727,261; 6,710,040; 6,432,969; 6,172,081; 6,011,155 and the like), protein tyrosine phosphatase-1B inhibitors (such as KR61639, IDD-3, PTP-3848, PTP-112, OC-86839, PNU-177496, compounds described in Vats, R. K., et al., *Current Science*, Vol. 88, No. 2, 25 Jan. 2005, pp. 241-249, and the like), glycogen phosphorylase inhibitors (such as NN-4201, CP-368296 and the like), glucose-6-phosphatase inhibitors, fructose 1,6-bisphosphatase inhibitors (such as CS-917, MB05032 and the like), pyruvate dehydrogenase inhibitors (such as AZD-7545 and the like), imidazoline derivatives (such as BL11282 and the like), hepatic gluconeogenesis inhibitors (such as FR-225659 and the like), D-chiroinositol, glycogen synthase kinase-3 inhibitors (such as compounds described in Vats, R. K., et al., *Current Science*, Vol. 88, No. 2, 25 Jan. 2005, pp. 241-249, and the like), incretin mimetics (such as exenatide and the like), glucagon receptor antagonists (such as BAY-27-9955, NN-2501, NNC-92-1687 and the like), glucagon-like peptide-1 (GLP-1), GLP-1 analogs (such as liraglutide, CJC-1131, AVE-0100 and the like), GLP-1 receptor agonists (such as AZM-134, LY-315902, GlaxoSmithKline 716155 and the like), amylin, amylin analogs and agonists (such as pramlintide and the like), fatty acid binding protein (aP2) inhibitors (such as compounds described in U.S. Pat. Nos. 6,984,645; 6,919,323; 6,670,380; 6,649,622; 6,548,529 and the like), beta-3 adrenergic receptor agonists (such as solabegron, CL-316243, L-771047, FR-149175 and the like), and other insulin sensitivity enhancers (such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020, GW-501516 and the like).

Examples of agents for treating diabetic complications suitable for use in combination with compounds of the present invention include aldose reductase inhibitors (such as epalrestat, imirestat, tolrestat, minalrestat, ponalrestat, zopolrestat, fidarestat, ascorbyl gamolenate, ADN-138, BAL-ARI8, ZD-5522, ADN-311, GP-1447, IDD-598, risarestat, zenarestat, methosorbinil, AL-1567, M-16209, TAT, AD-5467, AS-3201, NZ-314, SG-210, JTT-811, lindolrestat, sorbinil and the like), inhibitors of advanced glycation end-products (AGE) formation (such as pyridoxamine, OPB-9195, ALT-946, ALT-711, pimagedine and the like), AGE breakers (such as ALT-711 and the like), sulodexide, 5-hydroxy-1-methylhydantoin, insulin-like growth factor-I, platelet-derived growth factor, platelet-derived growth factor analogs, epidermal growth factor, nerve growth factor, uridine, protein kinase C inhibitors (such as ruboxistaurin, midostaurin and the like), sodium channel antagonists (such as mexiletine, oxcarbazepine and the like), nuclear factor-kappaB (NF-kappaB) inhibitors (such as dexlipotam and the like), lipid peroxidase inhibitors (such as tirilazad mesylate and the like), N-acetylated-alpha-linked-acid-dipeptidase inhibitors (such as GPI-5232, GPI-5693 and the like), and carnitine derivatives (such as carnitine, levacecamine, levocarnitine, ST-261 and the like).

Examples of antihyperuricemic agents suitable for use in combination with compounds of the present invention include uric acid synthesis inhibitors (such as allopurinol, oxypurinol and the like), uricosuric agents (such as probenecid, sulfinpyrazone, benzbromarone and the like) and urinary alkalinizers (such as sodium hydrogen carbonate, potassium citrate, sodium citrate and the like).

Examples of lipid-lowering/lipid-modulating agents suitable for use in combination with compounds of the present invention include hydroxymethylglutaryl coenzyme A reductase inhibitors (such as acitemate, atorvastatin, bervastatin, carvastatin, cerivastatin, colestolone, crilvastatin, dalvastatin, fluvastatin, glenvastatin, lovastatin, mevastatin, nisvastatin, pitavastatin, pravastatin, ritonavir, rosuvastatin, saquinavir, simvastatin, visastatin, SC-45355, SQ-33600, CP-83101, BB-476, L-669262, S-2468, DMP-565, U-20685, BMS-180431, BMY-21950, compounds described in U.S. Pat. Nos. 5,753,675; 5,691,322; 5,506,219; 4,686,237; 4,647,576; 4,613,610; 4,499,289 and the like), fibric acid derivatives (such as gemfibrozil, fenofibrate, bezafibrate, beclobrate, binifibrate, ciprofibrate, clinofibrate, clofibrate, etofibrate, nicofibrate, pirifibrate, ronifibrate, simfibrate, theofibrate, AHL-157 and the like), PPAR-alpha agonists (such as GlaxoSmithKline 590735 and the like), PPAR-delta agonists (such as GlaxoSmithKline 501516 and the like), acyl-coenzyme A:cholesterol acyltransferase inhibitors (such as avasimibe, eflucimibe, eldacimibe, lecimibide, NTE-122, MCC-147, PD-132301-2, C1-1011, DUP-129, U-73482, U-76807, TS-962, RP-70676, P-06139, CP-113818, RP-73163, FR-129169, FY-038, EAB-309, KY-455, LS-3115, FR-145237, T-2591, J-104127, R-755, FCE-27677, FCE-28654, YIC-C8-434, CI-976, RP-64477, F-1394, CS-505, CL-283546, YM-17E, 447C88, YM-750, E-5324, KW-3033, HL-004 and the like), probucol, thyroid hormone receptor agonists (such as liothyronine, levothyroxine, KB-2611, GC-1 and the like), cholesterol absorption inhibitors (such as ezetimibe, SCH48461 and the like), lipoprotein-associated phospholipase A2 inhibitors (such as rilapladib, darapladib and the like), microsomal triglyceride transfer protein inhibitors (such as CP-346086, BMS-201038, compounds described in U.S. Pat. Nos. 5,595,872; 5,739,135; 5,712,279; 5,760,246; 5,827,875; 5,885,983; 5,962,440; 6,197,798; 6,617,325; 6,821,967; 6,878,707 and the like), low density lipoprotein receptor activators (such as LY295427, MD-700 and the like), lipoxygenase inhibitors (such as compounds described in WO 97/12615, WO 97/12613, WO 96/38144 and the like), carnitine palmitoyl-transferase inhibitors (such as etomoxir and the like), squalene synthase inhibitors (such as YM-53601, TAK-475, SDZ-268-198, BMS-188494, A-87049, RPR-101821, ZD-9720, RPR-107393, ER-27856, compounds described in U.S. Pat. Nos. 5,712,396; 4,924,024; 4,871,721 and the like), nicotinic acid derivatives (such as acipimox, nicotinic acid, ricotinamide, nicomol, niceritrol, nicorandil and the like), bile acid sequestrants (such as colestipol, cholestyramine, colestilan, colesevelam, GT-102-279 and the like), sodium/bile acid cotransporter inhibitors (such as 264W94, S-8921, SD-5613 and the like), and cholesterol ester transfer protein inhibitors (such as torcetrapib, JTT-705, PNU-107368E, SC-795, CP-529414 and the like).

Examples of anti-obesity agents suitable for use in combination with compounds of the present invention include serotonin-norepinephrine reuptake inhibitors (such as sibutramine, milnacipran, mirtazapine, venlafaxine, duloxetine, desvenlafaxine and the like), norepinephrine-dopamine reuptake inhibitors (such as radafaxine, bupropion, amineptine and the like), selective serotonin reuptake inhibitors (such as citalopram, escitalopram, fluoxetine, fluvoxamine, paroxetine, sertraline and the like), selective norepinephrine reuptake inhibitors (such as reboxetine, atomoxetine and the like), norepinephrine releasing stimulants (such as rolipram, YM-992 and the like), anorexiants (such as amphetamine, methamphetamine, dextroamphetamine, phentermine, benzphetamine, phendimetrazine, phenmetrazine, diethylpropion, mazindol, fenfluramine, dexfenfluramine, phenylpropanolamine and the like), dopamine agonists (such as ER-230, doprexin, bromocriptine mesylate and the like), $H_3$-histamine antagonists (such as impentamine, thioperamide, ciproxifan, clobenpropit, GT-2331, GT-2394, A-331440, and the like), 5-HT2c receptor agonists (such as, 1-(m-chlorophenyl)piperazine (m-CPP), mirtazapine, APD-356 (lorcaserin), SCA-136 (vabicaserin), ORG-12962, ORG-37684, ORG-36262, ORG-8484, Ro-60-175, Ro-60-0332, VER-3323, VER-5593, VER-5384, VER-8775, LY-448100, WAY-161503, WAY-470, WAY-163909, MK-212, BVT.933, YM-348, IL-639, IK-264, ATH-88651, ATHX-105 and the like (see, e.g., Nilsson B M, *J. Med. Chem.* 2006, 49:4023-4034)), beta-3 adrenergic receptor agonists (such as L-796568, CGP 12177, BRL-28410, SR-5861 1A, ICI-198157, ZD-2079, BMS-194449, BRL-37344, CP-331679, CP-331648, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 and the like), cholecystokinin agonists (such as SR-146131, SSR-125180, BP-3.200, A-71623, A-71378, FPL-15849, GI-248573, GW-7178, GI-181771, GW-7854, GW-5823, and the like), antidepressant/acetylcholinesterase inhibitor combinations (such as venlafaxine/rivastigmine, sertraline/galanthamine and the like), lipase inhibitors (such as orlistat, ATL-962 and the like), anti-epileptic agents (such as topiramate, zonisamide and the like), leptin, leptin analogs and leptin receptor agonists (such as LY-355101 and the like), neuropeptide Y (NPY) receptor antagonists and modulators (such as SR-120819-A, PD-160170, NGD-95-1, BIBP-3226, 1229-U-91, CGP-71683, BIBO-3304, CP-671906-01, J-115814 and the like), ciliary neurotrophic factor (such as Axokine and the like), thyroid hormone receptor-beta agonists (such as KB-141, GC-1, GC-24, GB98/284425 and the like), cannabinoid CB1 receptor antagonists (such as rimonabant, SR147778, SLV 319 and the like (see, e.g., Antel J et al., *J. Med. Chem.* 2006, 49:4008-4016)), melanin-concentrating hormone receptor antagonists (such as GlaxoSmithKline 803430X, GlaxoSmithKline 856464, SNAP-7941, T-226296 and the like (see, e.g., Handlon A L and Zhou H, *J. Med. Chem.* 2006, 49:4017-4022)), melanocortin-4 receptor agonists (including PT-15, Ro27-3225, THIQ, NBI 55886, NBI 56297, NBI 56453, NBI 58702, NBI 58704, MB243 and the like (see, e.g., Nargund R P et al., *J. Med. Chem.* 2006, 49:4035-4043)), selective muscarinic receptor $M_1$ antagonists (such as telenzepine, pirenzepine and the like), opioid receptor antagonists (such as naltrexone, methylnaltrexone, nalmefene, naloxone, alvimopan, norbinaltorphimine, nalorphine and the like), and combinations thereof.

Examples of antihypertensive agents and agents for treating chronic heart failure, atherosclerosis or related diseases suitable for use in combination with compounds of the present invention include bimoclomol, angiotensin-converting enzyme inhibitors (such as captopril, enalapril, fosinopril, lisinopril, perindopril, quinapril, ramipril and the like), neutral endopeptidase inhibitors (such as thiorphan, omapatrilat, MDL-100240, fasidotril, sampatrilat, GW-660511, mixanpril, SA-7060, E-4030, SLV-306, ecadotril and the like), angiotensin II receptor antagonists (such as candesartan cilexetil, eprosartan, irbesartan, losartan, olmesartan medoxomil, telmisartan, valsartan, tasosartan, enoltasosartan and the like), endothelin-converting enzyme inhibitors (such as CGS 35066, CGS 26303, CGS-31447, SM-19712 and the like), endothelin receptor antagonists (such as tracleer, sitaxsentan, ambrisentan, L-749805, TBC-3214, BMS-182874, BQ-610, TA-0201, SB-215355, PD-180988, BMS-193884, darusentan, TBC-3711, bosentan, tezosentan, J-104132, YM-598, S-0139, SB-234551, RPR-118031A, ATZ-1993, RO-61-1790, ABT-546, enlasentan, BMS-207940 and the like), diuretic agents (such as hydrochlorothiazide, bendroflumethiazide, trichlonnethiazide, indapamide, metolazone, furosemide, bumetanide, torsemide, chlorthalidone, metolazone, cyclopenthiazide, hydroflumethiazide, tripamide, mefruside, benzylhydrochlorothiazide, penflutizide, methyclothiazide, azosemide, etacrynic acid, torasemide, piretanide, meticrane, potassium canrenoate, spironolactone, triamterene, aminophylline, cicletanine, LLU-alpha, PNU-80873A, isosorbide, D-mannitol, D-sorbitol, fructose, glycerin, acetazolamide, methazolamide, FR-179544, OPC-31260, lixivaptan, conivaptan and the like), calcium channel antagonists (such as amlodipine, bepridil, diltiazem, felodipine, isradipine, nicardipen, nimodipine, verapamil, S-verapamil, aranidipine, efonidipine, barnidipine, benidipine, manidipine, cilnidipine, nisoldipine, nitrendipine, nifedipine, nilvadipine, felodipine, pranidipine, lercanidipine, isradipine, elgodipine, azelnidipine, lacidipine, vatanidipine, lemildipine, diltiazem, clentiazem, fasudil, bepridil, gallopamil and the like), vasodilating antihypertensive agents (such as indapamide, todralazine, hydralazine, cadralazine, budralazine and the like), beta blockers (such as acebutolol, bisoprolol, esmolol, propanolol, atenolol, labetalol, carvedilol, metoprolol and the like), sympathetic blocking agents (such as amosulalol, terazosin, bunazosin, prazosin, doxazosin, propranolol, atenolol, metoprolol, carvedilol, nipradilol, celiprolol, nebivolol, betaxolol, pindolol, tertatolol, bevantolol, timolol, carteolol, bisoprolol, bopindolol, nipradilol, penbutolol, acebutolol, tilisolol, nadolol, urapidil, indoramin and the like), alpha-2-adrenoceptor agonists (such as clonidine, methyldopa, CHF-1035, guanabenz acetate, guanfacine, moxonidine, lofexidine, talipexole and the like), centrally acting antihypertensive agents (such as reserpine and the like), thrombocyte aggregation inhibitors (such as warfarin, dicumarol, phenprocoumon, acenocoumarol, anisindione, phenindione, ximelagatran and the like), and anti-platelets agents (such as aspirin, clopidogrel, ticlopidine, dipyridamole, cilostazol, ethyl icosapentate, sarpogrelate, dilazep, trapidil, beraprost and the like).

Furthermore, in another aspect, the invention provides for a pharmaceutical composition comprising effective amounts of a compound or mixture of compounds of Formula I, or a pharmaceutically acceptable salt or prodrug thereof, and at least one member selected from the group of therapeutic agents listed above as combination partners, in a pharmaceutically acceptable carrier.

The treatment of the present invention can be administered prophylactically to prevent or delay the onset or progression of a disease or condition (such as hyperglycemia), or therapeutically to achieve a desired effect (such as a desired level of serum glucose) for a sustained period of time.

The compounds of the present invention can be administered to a subject, e.g., a human patient, a domestic animal such as a cat or a dog, independently or together with a combination partner, in the form of their pharmaceutically acceptable salts or prodrugs, or in the form of a pharmaceutical composition where the compounds and/or combination partners are mixed with suitable carriers or excipient(s) in a therapeutically effective amount. Consequently, a compound or mixture of compounds of Formula I, or a pharmaceutically acceptable salt or prodrug thereof, and an additional active agent to be combined therewith, can be present in a single formulation, for example a capsule or tablet, or in two separate formulations, which can be the same or different, for example, in the form of a kit comprising selected numbers of doses of each agent.

The appropriate dosage of compound will vary according to the chosen route of administration and formulation of the composition, among other factors, such as patient response. The dosage can be increased or decreased over time, as required by an individual patient. A patient initially may be given a low dose, which is then increased to an efficacious dosage tolerable to the patient. Typically, a useful dosage for adults may be from 1 to 2000 mg, preferably 1 to 200 mg, when administered by oral route, and from 0.1 to 100 mg, preferably 1 to 30 mg, when administered by intravenous route, in each case administered from 1 to 4 times per day. When a compound of the invention is administered in combination with another therapeutic agent, a useful dosage of the combination partner may be from 20% to 100% of the normally recommended dose.

Dosage amount and interval can be adjusted individually to provide plasma levels of the active compounds which are sufficient to maintain therapeutic effect. Preferably, therapeutically effective serum levels will be achieved by administering single daily doses, but efficacious multiple daily dose schedules are included in the invention. In cases of local administration or selective uptake, the effective local concentration of the drug may not be related to plasma concentration. One having skill in the art will be able to optimize therapeutically effective local dosages without undue experimentation.

All publications and patent applications cited in this specification are herein incorporated by reference as if each individual publication or patent application were specifically and individually indicated to be incorporated by reference. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims. The invention will be described in greater detail by way of specific examples.

EXAMPLES

The following examples are offered for illustrative purposes, and are not intended to limit the invention in any manner. Those of skill in the art will readily recognize a variety of noncritical parameters which can be changed or modified to yield essentially the same results.

The names of compounds shown in the following examples were derived from the structures shown using the CambridgeSoft Struct=Name algorithm as implemented in ChemDraw Ultra version 10.0. Unless otherwise indicated, the structures of compounds synthesized in the examples below were confirmed using the following procedures:

(1) Gas chromatography—mass spectra with electrospray ionization (MS ESI) were obtained with an Agilent 5973N mass spectrometer equipped with an Agilent 6890 gas chromatograph with an HP-5 MS column (0.25 μm coating; 30 m×0.25 mm). The ion source was maintained at 230° C. and spectra were scanned from 25-500 amu at 3.09 sec per scan.

(2) High pressure liquid chromatography mass spectra (LC-MS) were obtained using Finnigan Surveyor HPLC equipped with a quaternary pump, a variable wavelength detector set at 254 nm, an XB-C18 column (4.6×50 mm, 5 μm), and a Finnigan LCQ ion trap mass spectrometer with electrospray ionization. Spectra were scanned from 80-2000 amu using a variable ion time according to the number of ions in the source. The eluents were B: acetonitrile and D: water. Gradient elution from 10% to 90% B in 8 min at a flow rate of 1.0 mL/min is used with a final hold at 90% B of 7 min. Total run time is 15 min.

(3) Routine one-dimensional NMR spectroscopy was performed on 400 MHz or 300 MHz Varian Mercury-Plus spectrometers. The samples were dissolved in deuterated solvents obtained from Qingdao Tenglong Weibo Technology Co., Ltd., and transferred to 5 mm ID NMR tubes. The spectra were acquired at 293 K. The chemical shifts were recorded on the ppm scale and were referenced to the appropriate solvent signals, such as 2.49 ppm for DMSO-d6, 1.93 ppm for $CD_3CN$, 3.30 ppm for $CD_3OD$, 5.32 ppm for $CD_2Cl_2$ and 7.26 ppm for $CDCl_3$ for spectra.

Example 1

The synthesis of key intermediate D is outlined in FIG. 4, with the details of the individual steps given below.

Preparation of (5-bromo-2-chlorophenyl)(4-ethoxyphenyl)methanone (Intermediate A)

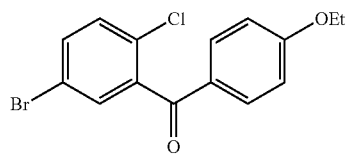

To a stirred solution of 5-bromo-2-chlorobenzoic acid (30 g, 0.127 mol) and oxalyl chloride (16.2 g, 0.127 mol) in dichloromethane (200 mL) was added DMF (0.5 mL) dropwise. The mixture was stirred at room temperature overnight and then evaporated to obtain crude product, which was used for the next step without further purification. The crude product was dissolved in dichloromethane (200 mL), the yellow solution was cooled to −5° C., and ethoxybenzene (phenetole) (15.5 g, 0.127 mmol) was added. Then $AlCl_3$ (17.8 g, 0.134 mmol) was added portionwise over 30 min. After the mixture was stirred at 4° C. for 1 h, TLC showed that no starting material remained. The reaction was quenched by pouring the mixture onto ice, and the suspension was extracted 2× with dichloromethane. The combined extracts were washed 2× with 1N HCl, 2× with 1N NaOH, 1× with $H_2O$ and 1× with brine prior to drying over $Na_2SO_4$. Removal of the volatiles and recrystallization from absolute ethanol gave intermediate A (25 g, yield 58%).

Preparation of 4-bromo-1-chloro-2-(4-ethoxybenzyl)benzene (Intermediate B)

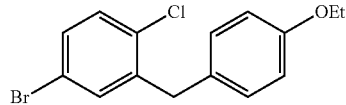

To a stirred solution of $Et_3SiH$ (6.8 g, 0.058 mol) and (5-bromo-2-chlorophenyl)(4-ethoxyphenyl)methanone (intermediate A) (10 g, 0.029 mol) in TFA (100 mL) was added $CF_3SO_3H$ (0.1 mL). Within minutes the temperature increased, causing the solution to reflux violently. After slow cooling to room temperature, the mixture was heated to reflux until TLC (PE:EA=20:1) showed that no starting material remained. The mixture was evaporated under reduced pressure, the residue was extracted with ethyl acetate, and the organic layer was separated and washed with water, aqueous $Na_2CO_3$, and brine, and dried over $Na_2SO_4$. Evaporation and distillation under reduced pressure was performed to eliminate $Et_3SiO$. Recrystallization of the residue from absolute ethanol gave intermediate B (4.7 g, yield 50%).

Preparation of (3R,4R,5S,6R)-2-(4-chloro-3-(4-ethoxybenzyl)phenyl)-6-(hydroxymethyl)tetrahydro-2H-pyran-3,4,5-triol (Intermediate C)

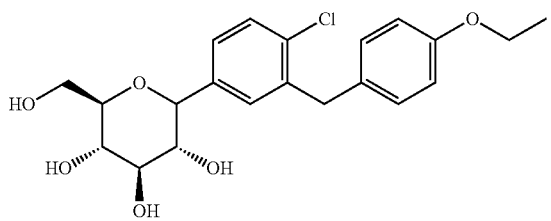

To a stirred solution of 4-bromo-1-chloro-2-(4-ethoxybenzyl)benzene (intermediate B) (8 g, 24 mmol) in 30 mL of dry THF:toluene (1:2) under Ar was added n-BuLi (2.5 M, 0.7 mL) dropwise at −78° C. After stirring for an additional 30 min, the solution was transferred to a stirred solution of 2,3,4,6-tetra-O-trimethylsilyl-β-D-glucolactone (also called (3R,4S,5R,6R)-3,4,5-tris(trimethylsilyloxy)-6-((trimethylsilyloxy)methyl)tetrahydro-2H-pyran-2-one) (0.28 g, 0.60 mmol) in 30 mL of toluene. The solution was stirred for 1 h at −78° C. prior to quenching by addition of 50 mL of methanol containing MeSO$_3$H (1.5 mL, 24 mmol). The mixture was stirred overnight, then quenched by the addition of aqueous NaHCO$_3$ and extracted with EtOAc. The organic layer was washed with brine and dried over Na$_2$SO$_4$. After concentration, the residue was dissolved in hot (50° C.) toluene (20 mL). The resulting solution was poured into 100 mL of stirred hexane. The precipitate was collected by filtration and concentrated to give the crude intermediate, which was used without further purification. The crude intermediate (6 g, 13.6 mmol) was dissolved in 40 mL of DCM:MeCN (1:1) and Et$_3$SiH (4.4 mL, 27.3 mmol) was added, followed by addition of BF$_3$.Et$_2$O (2.0 mL, 20.5 mmol) at a rate to insure the temperature remained under 0° C. The stirred solution was allowed to to 0° C. over 5 h. When TLC showed it was complete, the reaction was quenched by addition of saturated aqueous NaHCO$_3$. The mixture was removed and the residue was extracted with EtOAc. The organic layer was washed with water and brine and dried over Na$_2$SO$_4$. The product was concentrated to give intermediate C, which was used without further purification.

Preparation of (3R,4R,5S,6R)-2-(4-chloro-3-(4-hydroxybenzyl)phenyl)-6-(hydroxymethyl)tetrahydro-2H-pyran-3,4,5-triol (Intermediate D)

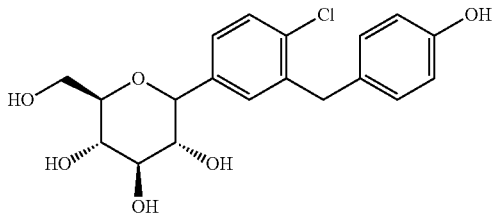

To a stirred solution of (3R,4R,5S,6R)-2-(4-chloro-3-(4-ethoxybenzyl)phenyl)-6-(hydroxymethyl)tetrahydro-2H-pyran-3,4,5-triol (Intermediate C) (2 g, 5.9 mmol) in dichloromethane was added BBr$_3$ (14.6 mL, 1 M) dropwise at −78° C. After the addition was complete, the mixture was allowed to warm to 0° C. and held at this temperature for 2 h. When LC-MS showed that no starting material remained, the mixture was cooled to −78° C. again, and quenched with water. When the temperature was stable, saturated NaHCO$_3$ solution was added. The mixture was evaporated under reduced pressure, and the residue was extracted with EtOAc. The organic layer was washed with NaHCO$_3$ and brine, dried over Na$_2$SO$_4$, evaporated and purified to obtain intermediate D (0.7 g).

In addition, for use in the synthesis of certain compounds of the invention, the 2S isomer (intermediate D1) and the 2R isomer (intermediate D2) of intermediate D were separated by preparative LC-MS. Intermediate D1: 1H NMR (CD$_3$OD): δ 7.30 (m, 3H), 6.97 (d, 2H, J=6.8 Hz), 6.68 (d, 2H, J=6.8 Hz), 4.56 (s, 1H), 4.16 (s, 1H), 3.91~4.02 (m, 5H), 3.79 (m, 1H), 3.64 (m, 1H). Intermediate D2: $^1$H NMR (CD$_3$OD): δ 7.29~7.33(m, 3H), 7.00 (d, 2H, J=6.8 Hz), 6.70 (d, 2H, J=6.8 Hz), 4.58 (d, 1H, J=4.0 Hz), 3.96~4.02 (m, 4H), 3.93~3.95 (m, 1H), 3.81~3.85 (m, 1H), 3.64~3.69 (m, 1H).

Example 2

The synthesis of compounds E and F within the invention is outlined in FIG. 5, with the details given below.

Preparation of (2S,3R,4R,5S,6R)-2-(4-chloro-3-(4-(2-(2-(4-methylpiperazin-1-yl)ethoxy)ethoxy)benzyl)phenyl)-6-(hydroxymethyl)tetrahydro-2H-pyran-3,4,5-triol (Compound E) and (2R,3R,4R,5S,6R)-2-(4-chloro-3-(4-(2-(2-(4-methylpiperazin-1-yl)ethoxy)ethoxy)benzyl)phenyl)-6-(hydroxymethyl)tetrahydro-2H-pyran-3,4,5-triol (Compound F)

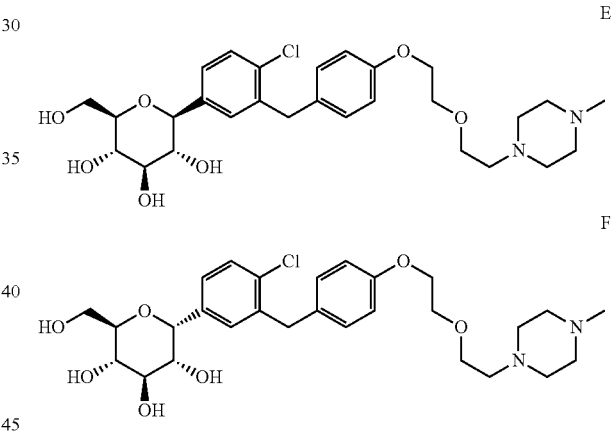

To a solution of (3R,4R,5S,6R)-2-(4-chloro-3-(4-hydroxybenzyl)phenyl)-6-(hydroxymethyl)tetrahydro-2H-pyran-3,4,5-triol (intermediate D) (50 mg, 0.13 mmol) in DMF (3.0 mL) were added 1-bromo-2-(2-bromoethoxy)ethane (91 mg, 0.39 mmol), Cs$_2$CO$_3$ (127 mg, 0.39 mmol) and 1-methylpiperazine (66 mg, 0.66 mmol). After being vigorously stirred at an external temperature of 80° C. overnight, the solution was purified by preparative HPLC to give compounds E (35 mg) and F (12 mg) as yellow oil. Compound E: $^1$H NMR (CD$_3$OD): δ 7.37-7.27 (m, 3H), 7.13 (d, 2H, J=8.4 Hz), 6.84 (d, 2H, J=8.4Hz), 4.12-4.03 (m, 5H), 3.89-3.67 (m, 3H), 3.45-3.38 (m, 3H), 3.32-3.27 (m, 1H), 2.95-2.67 (m, 10H), 2.61 (s, 3H); MS ESI (m/z): 551 (M+H)$^+$, calc. 550. Compound F: $^1$H NMR (CD3OD): δ 7.34-7.29 (m, 3H), 7.11 (d, 2H, J=8.4 Hz), 6.85 (d, 2H, J=8.4 Hz), 4.58 (d, 1H, J=3.6 Hz), 4.18-3.93 (m, 7H), 3.82-3.73 (m, 5H), 2.91-2.82 (m, 9H); 2.63 (s, 3H).

Example 3

The synthesis of compound G within the invention is outlined in FIG. 6, with the details given below.

Preparation of (2S,3R,4R,5S,6R)-2-(4-chloro-3-(4-(2-(2-morpholinoethoxy)ethoxy)benzyl)phenyl)-6-(hydroxymethyl)tetrahydro-2H-pyran-3,4,5-triol (Compound G)

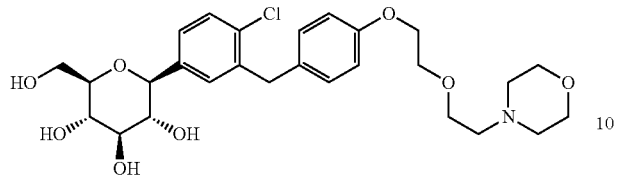

To a solution of (3R,4R,5S,6R)-2-(4-chloro-3-(4-hydroxybenzyl)phenyl)-6-(hydroxymethyl)tetrahydro-2H-pyran-3,4,5-triol (intermediate D) (50 mg, 0.13 mmol) in DMF (3.0 mL) were added 1-bromo-2-(2-bromoethoxy)ethane (91 mg, 0.39 mmol), $Cs_2CO_3$ (127 mg, 0.39 mmol) and morpholine (68 mg, 0.79 mmol). After being vigorously stirred at an external temperature of 80° C. overnight, the solution was purified by preparative HPLC to give compound G (35 mg). $^1$H NMR ($CD_3OD$): δ 7.60-7.40 (m, 3H), 7.12-7.09 (m, 2H), 6.85 (d, 2H, J=8.4 Hz), 4.60 (d, 1H, J=3.2 Hz), 4.24-4.11 (m, 4H), 4.09-3.90 (m, 4H), 3.83-3.78 (m, 9H), 3.72-3.70 (m, 4H), 3.65-3.64 (m, 2H), 3.04-2.98 (m, 5H); MS ESI (m/z) 538 $(M+H)^+$, calc. 537.

Example 4

The synthesis of compounds K and L within the invention is outlined in FIG. 7, with the details given below.

Preparation of 4-(5-bromo-2-chlorobenzyl)phenol (Intermediate H)

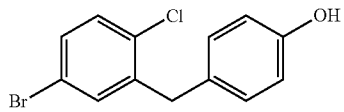

To a stirred solution of 4-bromo-1-chloro-2-(4-ethoxybenzyl)benzene (intermediate B) (3.0 g, 9.3 mmol) in dichloromethane (20 mL) was added $BBr_3$ (1M in dichloromethane, 18.5 mL, 18.5 mmol) under the temperature of −78° C. The mixture was allowed to warm to room temperature, and the reaction was monitored using TLC (PE:EA = 10:1). When TLC showed the reaction was complete, the mixture was poured onto ice and extracted with dichloromethane. The organic layer was washed with saturated $NaHCO_3$ solution, water, and brine, dried over $Na_2SO_4$, and evaporated under reduced pressure to obtain intermediate H (2.75 g, yield 90%). $^1$H NMR ($CDCl_3$): δ 7.23-7.29 (m, 3H), 7.08 (d, 2H, J=8.8Hz), 6.79 (d, 2H, J=8.8Hz), 4.00 (s, 1H).

Preparation of 2-(4-(5-bromo-2-chlorobenzyl)phenoxy)ethanol (Intermediate I)

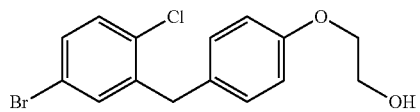

To a stirred solution of 4-(5-bromo-2-chlorobenzyl)phenol (intermediate H) (5.5 g, 18 mmol) in DMF (50 mL) was added $Cs_2CO_3$ (12 g, 36 mmol). After stirring at room temperature for 0.5 h, 2-bromoethanol (4.6 g, 36 mmol) was added dropwise, and the mixture was stirred at 80° C. overnight. The mixture was extracted twice with ethyl acetate, and the organic layer was washed with water and brine, dried over $Na_2SO_4$, and evaporated under reduced pressure to obtain intermediate I (4.8 g, yield 76%).

Preparation of 4-bromo-2-(4-(2-(but-2-ynyloxy)ethoxy)benzyl)-1-chlorobenzene (Intermediate J)

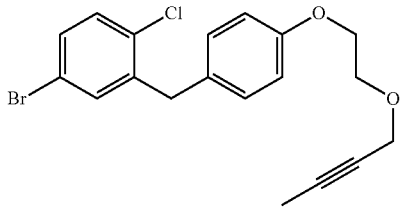

To a stirred solution of 2-(4-(5-bromo-2-chlorobenzyl)phenoxy)ethanol (intermediate I) (0.5 g, 1.46 mmol) in THF (10 mL) was added NaH (0.084 g, 1.76 mmol) at 0° C. degree. The mixture was stirred for 0.5 h, and then 1-bromobut-2-yne (0.23 g, 1.76 mmol) was added dropsise. The solution was stirred at room temperature overnight and then poured over ice and extracted with ethyl acetate. The organic layer was washed with water and brine, dried over $Na_2SO_4$, concentrated under reduced pressure and purified by column chromatography to obtain intermediate J (0.45 g, yield 78.1%).

Preparation of (2S,3R,4R,5S,6R)-2-(3-(4-(2-(but-2-ynyloxy)ethoxy)benzyl)-4-chlorophenyl)-6-(hydroxymethyl)tetrahydro-2H-pyran-3,4,5-triol (Compound K) and (2R,3R,4R,5S,6R)-2-(3-(4-(2-(but-2-ynyloxy)ethoxy)benzyl)-4-chlorophenyl)-6-(hydroxymethyl)tetrahydro-2H-pyran-3,4,5-triol (Compound L)

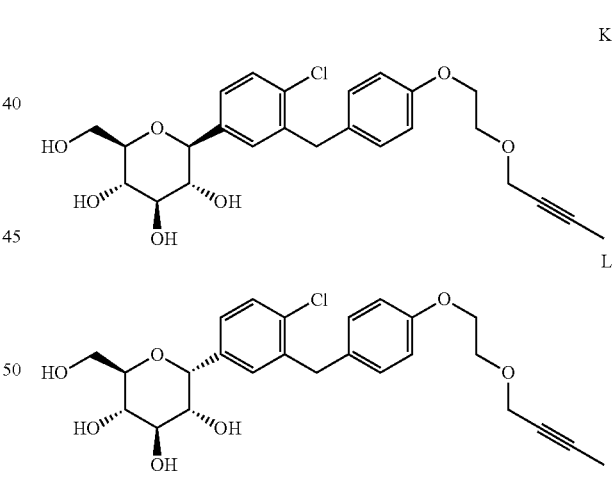

To a −78° C. solution of 4-bromo-2-(4-(2-(but-2-ynyloxy)ethoxy)benzyl)-1-chlorobenzene (intermediate J) (0.2 g, 0.50 mmol) in 10 mL of dry THF:toluene (1:2) under Ar was added n-BuLi (2.5 M, 0.22 mL) in hexane. After stirring for 30 min following the addition, this solution was transferred to a stirred −78° C. solution of 2,3,4,6-tetra-O-trimethylsilyl-β-D-glucolactone (also called (3R,4S,5R,6R)-3,4,5-tris(trimethylsilyloxy)-6-((trimethylsilyloxy)methyl)tetrahydro-2H-pyran-2-one) (0.28 g, 0.60 mmol) in 10 mL of toluene. The solution was stirred for 2 h prior to quenching by addition of 10 mL of MeOH containing $MeSO_3H$ (0.1 mL). The mixture was stirred for 30 min, quenched by addition of aqueous NaHCO$_3$, diluted with 10 mL of H$_2$O and extracted twice with EtOAc. The combined EtOAc fractions were washed with brine, dried over Na$_2$SO$_4$, evaporated and used directly for the next step. To a stirred 0° C. solution of the above crude product in CH$_2$Cl$_2$ (10 mL) was added Et$_3$SiH (0.06 g, 1.0 mmol) followed by BF$_3$.Et$_2$O (0.1 g, 0.76 mmol). The solution was stirred at this temperature for 5 h, quenched by addition of saturated aqueous NaHCO$_3$, and the organic volatiles were removed under reduced pressure. The residue was partioned between 10 mL each of EtOAc and H$_2$O, and the organic layer was evaporated and purified by preparative HPLC to obtain compounds K and L. Compound K: $^1$H NMR (CD$_3$OD): δ 7.30~7.37 (m, 3H), 7.11 (d, 2H, J=8.8 Hz), 6.84 (d, 2H, J=8.8 Hz), 4.18~4.20 (m, 2H), 4.09~4.11 (m, 3H), 4.03 (d, 2H, J=8 Hz), 3.87~3.90 (m, 3H), 3.82 (m, 1H), 3.39~3.44 (m, 3H), 3.30 (m,1H); MS ESI (m/z): 477 (M+H)$^+$, calc. 476. Compound L: $^1$H NMR (CD$_3$OD): δ 7.31~7.34 (m, 3H), 7.10 (d, 2H, J=8.8 Hz), 6.85 (d, 2H, J=8.8 Hz), 4.58 (d, 1H, J=4 Hz), 4.19 (m, 3H), 4.10 (m, 2H), 4.09 (s, 4H), 4.03 (d, 1H, J=4.0 Hz), 3.82 (m, 3H), 3.82 (m,1H).

Example 5

The synthesis of compounds M and N within the invention is outlined in FIG. 8, with the details given below.

Preparation of (2S,3R,4R,5S,6R)-2-(4-chloro-3-(4-(2-(2-methoxyethoxy)ethoxy)benzyl)phenyl)-6-(hydroxymethyl)tetrahydro-2H-pyran-3,4,5-triol (Compound M) and (2R,3R,4R,5S,6R)-2-(4-chloro-3-(4-(2-(2-methoxyethoxy)ethoxy)benzyl)phenyl)-6-(hydroxymethyl)tetrahydro-2H-pyran-3,4,5-triol (Compound N)

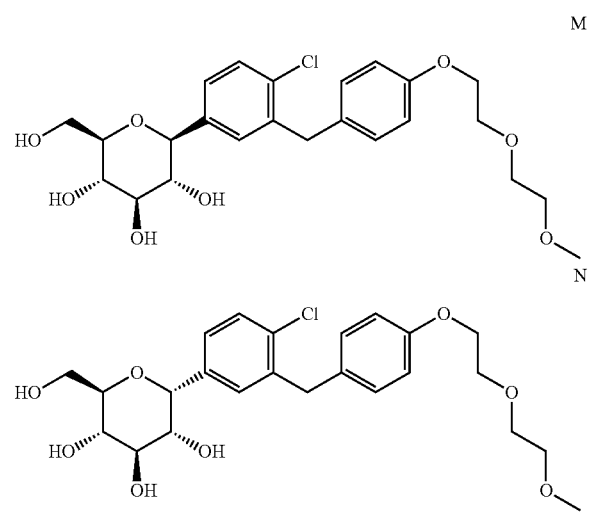

M

N

To a stirred solution of (3R,4R,5S,6R)-2-(4-chloro-3-(4-hydroxybenzyl)phenyl)-6-(hydroxymethyl)tetrahydro-2H-pyran-3,4,5-triol (intermediate D) (200 mg, 0.47 mmol) in DMF (20 mL) was added Cs$_2$CO$_3$ (0.30 g, 0.94 mmol). The mixture was allowed to stir at room temperature for 0.5 h, and then 2-(2-methoxyethoxy)ethyl methanesulfonate (112 mg, 0.56 mmol) was added dropwise. The mixture was then stirred at 50° C. overnight, after which the mixture was evaporated and purified by preparative HPLC to obtain compounds M (17.6 mg) and N (13.9 mg). Compound M: $^1$H NMR (CD$_3$OD): δ 7.31~7.48 (m, 3H), 7.09 (d, 2H, J=8.8 Hz), 6.82 (d, 2H, J=8.8 Hz), 4.06~4.09 (m, 3H), 4.01 (d, 2H, J=8 Hz), 3.79~3.81 (m, 3H), 3.66~3.68 (m, 3H), 3.53~3.56 (m, 2H), 3.39 (m, 3H), 3.35 (s, 3H), 3.29 (m,1H); MS ESI (m/z) 483 (M+H)$^+$, calc. 482. Compound N: $^1$H NMR (CD$_3$OD): δ 7.28~7.32 (m, 3H), 7.07 (d, 2H, J=8.8 Hz), 6.82 (d, 2H, J=8.8 Hz), 4.61 (s, 3H), 4.56 (d, 1H, J=4.0 Hz), 4.16 (m, 1H), 4.07 (m, 2H), 3.99 (m, 4H), 3.91 (m, 1H), 3.79 (m, 3H), 3.56 (m, 3H), 3.35 (m, 2H), 3.30 (s,3H).

Example 6

Figure 9:
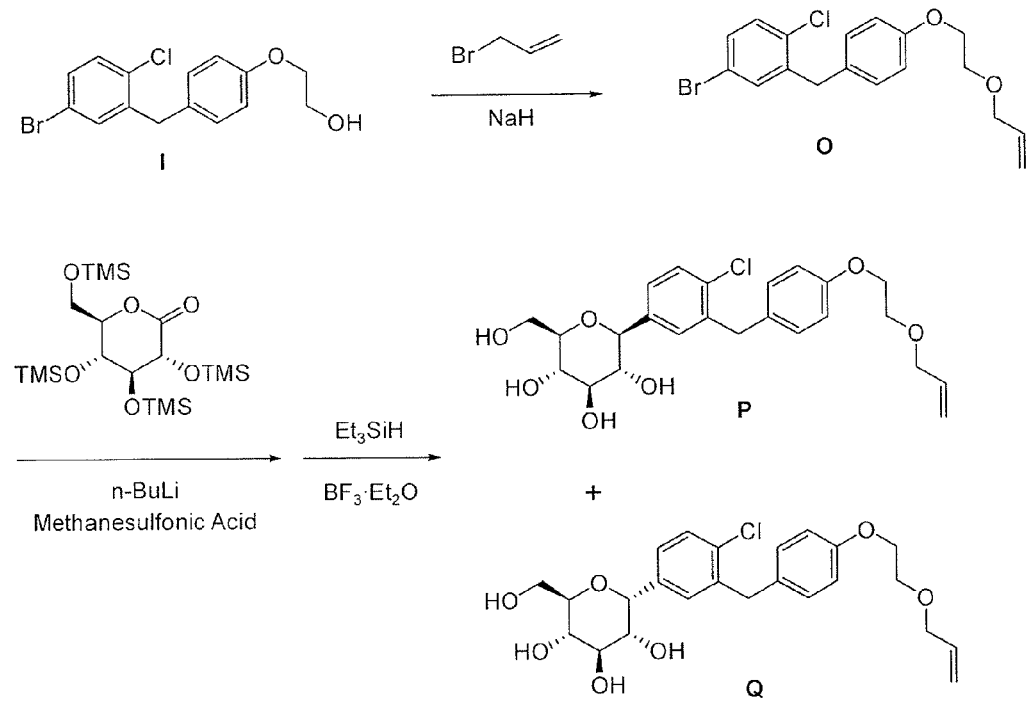
FIG. 9 is the outline for the synthesis of compounds P and Q of the invention.

The synthesis of compounds P and Q within the invention is outlined in FIG. 9, with the details given below.

Preparation of 2-(4-(2-(allyloxy)ethoxy)benzyl)-4-bromo-1-chlorobenzene (Intermediate O)

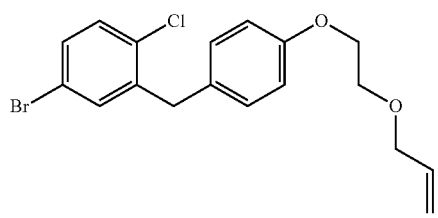

To a stirred solution of 2-(4-(5-bromo-2-chlorobenzyl)phenoxy)ethanol (intermediate I) (0.5 g, 1.47 mmol) in anhydrous THF was added NaH (84 mg, 1.76 mmol) at 0° C. The mixture was stirred at this temperature for 30 min, and then allyl bromide (3-bromoprop-1-ene) (0.21 g, 1.75 mmol) was added and the temperature of the mixture was allowed to rise to the room temperature. The reaction was quenched by pouring it over ice-water, and the mixture was extracted with ethyl acetate. The organic layer was washed with water and brine, dried over Na$_2$SO$_4$, and then purified by column chromatography (EA:PE=1:20 to 1:10) to obtain intermediate O (0.3 g, yield 54%).

Preparation of (2S,3R,4R,5S,6R)-2-(3-(4-(2-(allyloxy)ethoxy)benzyl)-4-chlorophenyl)-6-(hydroxymethyl)tetrahydro-2H-pyran-3,4,5-triol (Compound P) and (2R,3R,4R,5S,6R)-2-(3-(4-(2-(allyloxy)ethoxy)benzyl)-4-chlorophenyl)-6-(hydroxymethyl)tetrahydro-2H-pyran-3,4,5-triol (Compound Q)

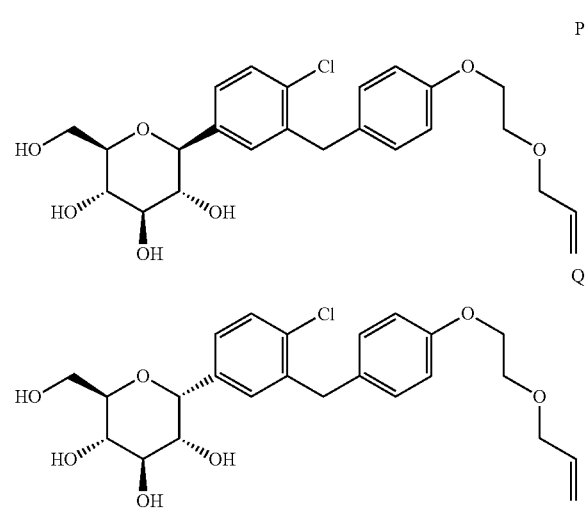

P

Q

To a stirred solution of 2-(4-(2-(allyloxy)ethoxy)benzyl)-4-bromo-1-chlorobenzene (intermediate O) (1.0 g, 2.6 mmol)

in 20 mL of dry THF:toluene (1:2) under argon was added n-BuLi (2.5 M, 1.1 mL) dropwise at −78° C. After stirring for 30 min following the addition, this solution was transferred to a stirred solution of 2,3,4,6-tetra-O-trimethylsilyl-β-D-glucolactone (also called (3R,4S,5R,6R)-3,4,5-tris(trimethylsilyloxy)-6-((trimethylsilyloxy)methyl)tetrahydro-2H-pyran-2-one) (1.47 g, 3.1 mmol) in 20 mL of toluene. The solution was stirred for 1 h at −78° C. prior to quenching by addition of 10 mL of MeOH containing methanesulfonic acid (0.20 mL). The mixture was stirred for 1 h, and then the reaction was quenched by addition of aqueous NaHCO$_3$. The mixture was extracted with ethyl acetate, and the organic layer was washed with brine, dried over Na$_2$SO$_4$ and evaporated to obtain the crude product (1.20 g), which was used for the next step without further purification. To the crude product in dichloromethane (20 mL) was added Et$_3$SiH (0.28 g, 4.8 mmol) followed by addition of BF$_3$.Et$_2$O (0.45 mL, 3.6 mmol) at ~5° C. The solution was allowed to stir at 0° C. for 3 h. When LC-MS revealed the reaction was complete, the reaction was quenched by addition of aqueous NaHCO$_3$ (20 mL), the organic volatiles were removed under reduced pressure, and the residue was partitioned between 20 mL each of EtOAc and H$_2$O. After separating phases, the organic layer was washed with brine, dried over Na$_2$SO$_4$, evaporated and purified by preparative HPLC to obtain compounds P and Q. Compound P: $^1$H NMR (CD$_3$OD): δ 7.27~7.36 (m, 3H), 7.10 (d, 2H, J=8.8 Hz), 6.83 (d, 2H, J=8.8 Hz), 5.90 (m, 1H), 5.28~5.38 (m, 1H), 5.17~5.20 (m, 1H), 4.07~4.11 (m, 3H), 3.99 (d, 1H, J=8.0 Hz), 3.87 (m, 1H), 3.76 (m, 2H), 3.68 (m, 1H), 3.38 (m, 3H), 3.28 (m, 1H); MS ESI (m/z): 465 (M+H)$^+$, calc. 464. Compound Q: $^1$H NMR (CD$_3$OD): δ 7.12~7.34 (m, 3H), 7.09 (d, 2H, J=8.8 Hz), 6.84 (d, 2H, J=8.8 Hz), 5.90 (m, 1H), 5.28~5.33 (m, 2H), 4.86~5.20 (m, 2H), 4.58 (d, 1H, J=4.0 Hz), 4.19 (m, 1H), 4.01~4.10 (m, 8H), 3.94 (m, 1H), 3.78 (m, 3H), 3.76 (m, 1H).

Example 7

Figure 10:
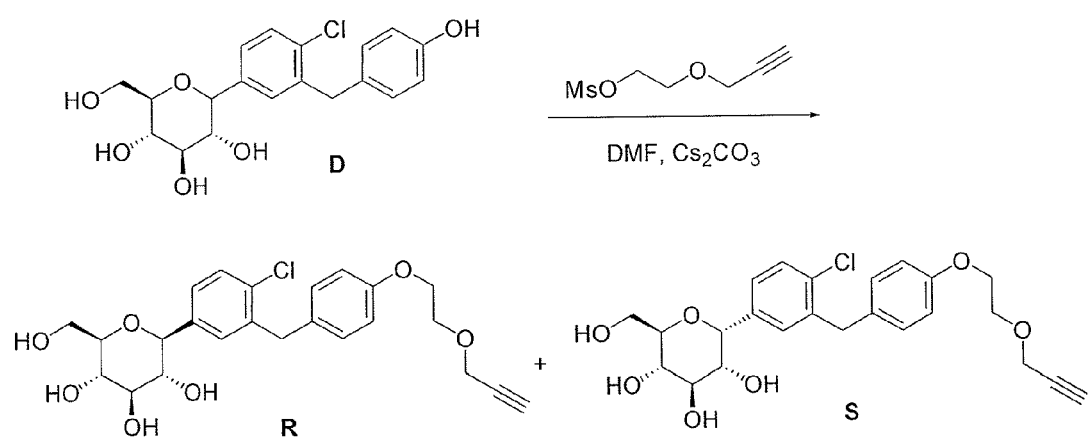
FIG. 10 is the outline for the synthesis of compounds R and S of the invention.

The synthesis of compounds R and S within the invention is outlined in FIG. 10, with the details given below.

Preparation of (2S,3R,4R,5S,6R)-2-(4-chloro-3-(4-(2-(prop-2-ynyloxy)ethoxy)benzyl)phenyl)-6-(hydroxymethyl)tetrahydro-2H-pyran-3,4,5-triol (Compound R) and (2R,3R,4R,5S,6R)-2-(4-chloro-3-(4-(2-(prop-2-ynyloxy)ethoxy)benzyl)phenyl)-6-(hydroxymethyl)tetrahydro-2H-pyran-3,4,5-triol (Compound S)

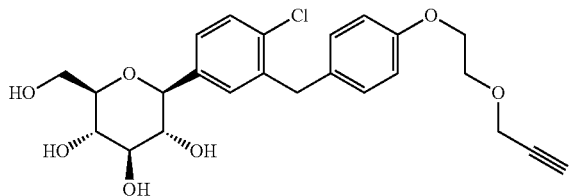

R

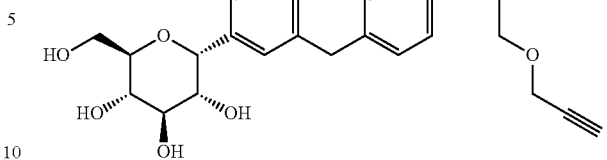

S

To a stirred solution of (3R,4R,5S,6R)-2-(4-chloro-3-(4-hydroxybenzyl)phenyl)-6-(hydroxymethyl)tetrahydro-2H-pyran-3,4,5-triol (intermediate D) (200 mg) in DMF (20 mL) was added Cs$_2$CO$_3$ (0.26 g). The mixture was allowed to stir at room temperature for 30 min, and then 2-(prop-2-ynyloxy) ethyl methanesulfonate (140 mg) was added dropwise. The mixture was stirred at 60° C. overnight, whereupon LC-MS showed intermediate D was completely consumed. The mixture was filtered, evaporated under reduced pressure, and purified by preparative HPLC to give compounds R (35 mg) and S (20.9 mg). Compound R: $^1$H NMR (CD$_3$OD): δ 7.32~7.35 (m, 3H), 7.10 (d, 2H, J=8.8 Hz), 6.83 (d, 2H, J=8.8 Hz), 4.23 (d, 1H, J=2.4 Hz), 4.07~4.10 (m, 3H), 4.02 (d, 2H, J=8.4 Hz), 3.83~3.85 (m, 3H), 3.65 (m, 1H), 3.35 (m, 3H), 3.32 (s, 1H), 2.86 (t, 1H, J=2.4 Hz); MS ESI (m/z): 463 (M+H)$^+$, calc. 462. Compound S: $^1$H NMR (CD$_3$OD): δ 7.30~7.33 (m, 3H), 7.09 (d, 2H, J=8.8 Hz), 6.84 (d, 2H, J=8.8 Hz), 4.92 (d, 1H, J=4.0 Hz), 4.25 (d, 2H, J=2Hz), 4.17 (m, 1H), 4.10 (m, 2H), 4.00 (m, 4H), 3.92 (m, 1H), 3.85 (m, 3H), 3.81 (m, 1H).

Example 8

Figure 11:
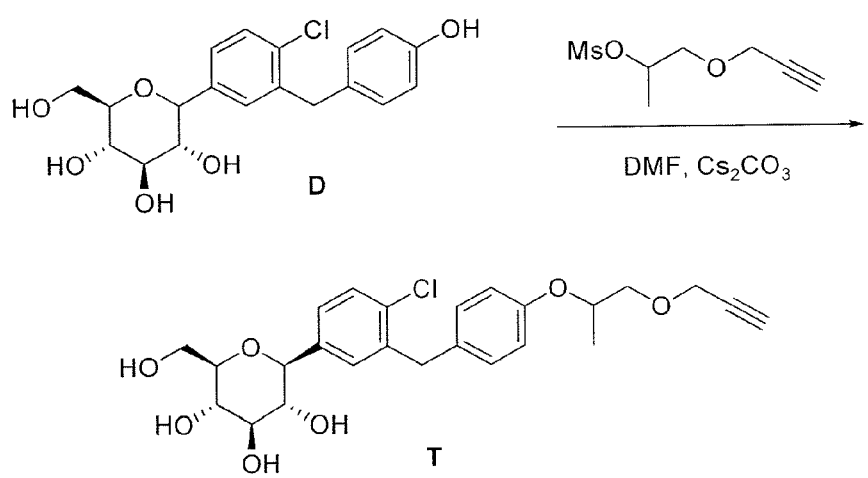
FIG. 11 is the outline for the synthesis of compound T of the invention.

The synthesis of compound T within the invention is outlined in FIG. 11, with the details given below.

Preparation of (2S,3R,4R,5S,6R)-2-(4-chloro-3-(4-(1-(prop-2-ynyloxy)propan-2-yloxy)benzyl)phenyl)-6-(hydroxymethyl)tetrahydro-2H-pyran-3,4,5-triol (Compound T)

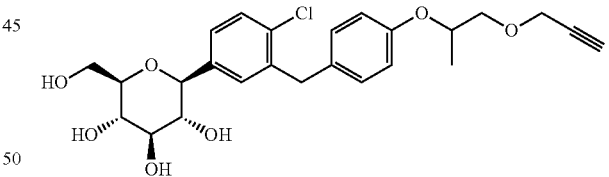

To a stirred solution of (3R,4R,5S,6R)-2-(4-chloro-3-(4-hydroxybenzyl)phenyl)-6-(hydroxymethyl)tetrahydro-2H-pyran-3,4,5-triol (intermediate D) (50 mg, 0.13 mmol) in DMF (10 mL) was added Cs$_2$CO$_3$ (64 mg, 0.20 mmol) and the mixture was stirred for 0.5 h. Then 1-(prop-2-ynyloxy)propan-2-yl methanesulfonate (38 mg, 0.20 mmol) was added, and the mixture was stirred at 40° C. overnight. The mixture then was filtered, evaporated under reduced pressure, and the residue was purified by preparative HPLC to obtain compound T (8.9 mg) as a white powder. $^1$H NMR (CD$_3$OD): δ 7.25~7.34 (m, 3H), 7.08 (d, 2H, J=8.8 Hz), 6.82 (d, 2H, J=8.8 Hz), 4.56 (S, 1H), 4.18 (m, 1H), 5.28~5.33 (m, 2H), 4.07 (m, 2H), 4.01 (d, 1H, J=8.0 Hz), 3.87 (d, 1H, J=1.2Hz), 3.85 (m, 1H), 3.60 (m, 3H), 3.38 (m, 3H), 3.28 (m,1H), 2.82 (m, 1H), 1.24 (d, 2H).

Example 9

Figure 12:
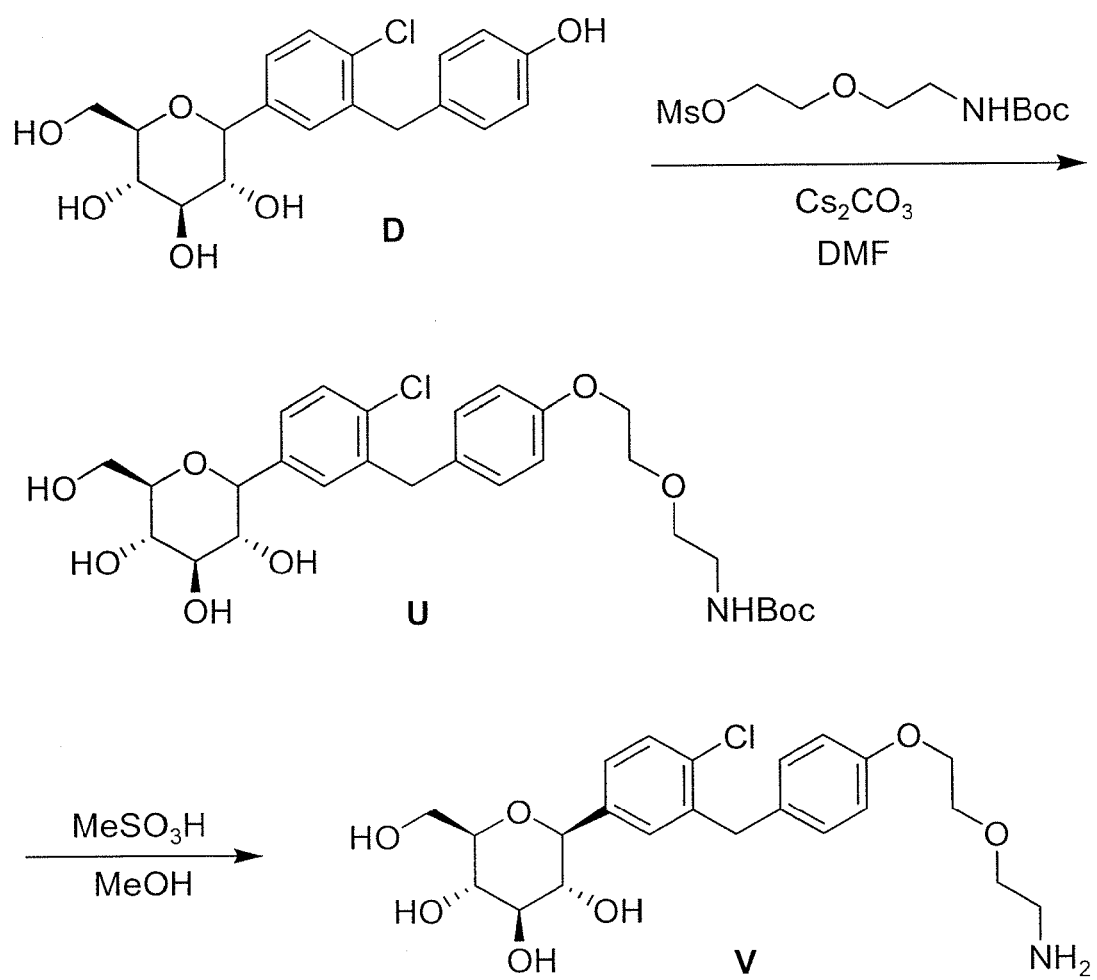
FIG. 12 is the outline for the synthesis of compound V of the invention.

The synthesis of compound V within the invention is outlined in FIG. 12, with the details given below.

Preparation of (2S,3R,4R,5S,6R)-2-(3-(4-(2-(2-aminoethoxy)ethoxy)benzyl)-4-chlorophenyl)-6-(hydroxymethyl)tetrahydro-2H-pyran-3,4,5-triol (Compound V)

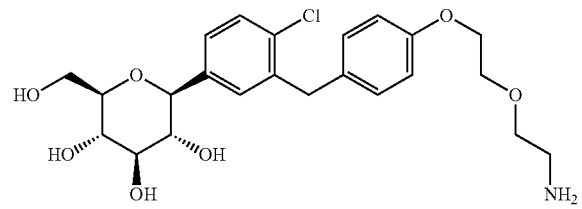

(3R,4R,5S,6R)-2-(4-chloro-3-(4-hydroxybenzyl)phenyl)-6-(hydroxymethyl)tetrahydro-2H-pyran-3,4,5-triol (intermediate D) (30 mg, 78.7 mmol), 2-(2-(tert-butoxycarbonylamino)ethoxy)ethyl methanesulfonate (26.8 mg, 94.5 mmol) and $Cs_2CO_3$ (30.8 mg, 94.5 mmol) were dissolved in DMF (3 ml) at room temperature and stirred overnight. The mixture was then extracted with EtOAc, washed with $NH_4Cl$ and NaCl, dried over $Na_2SO_4$, and evaporated to get the crude product, tert-butyl 2-(2-(4-(2-chloro-5-((2S,3R,4R,5S,6R)-3,4,5-trihydroxy-6-(hydroxymethyl)tetrahydro-2H-pyran-2-yl)benzyl)phenoxy)ethoxy)ethylcarbamate (intermediate U) (40 mg), which was used for the next step without further purification. The crude intermediate U was dissolved in MeOH (0.5 mL), $MeSO_3H$ (6 μL) was added, and the mixture was stirred overnight at room temperature. Then the reaction was quenched with $NaHCO_3$, the mixture was extracted with ethyl acetate, and the organic layer was washed with brine, dried over $Na_2SO_4$, concentrated, and separated by preparative HPLC to obtain compound V (11.6 mg). $^1H$ NMR ($CD_3OD$): δ 7.40~7.27 (m, 3H), 7.14~7.10 (m, 2 H), 6.87~6.85 (m, 2 H), 4.54 (d, J=16, 1H), 4.19~4.18 (m, 1H), 4.16~4.14 (m, 2H), 4.05~4.01 (m, 4 H), 3.94~3.93 (m, 1H), 3.88~3.86 (m, 2H), 3.83~3.76 (m, 3H), 3.67~3.57 (m, 1H), 3.16~3.13 (m, 2 H); MS ESI (m/z): 468 (M+H)+, calc. 467.

Example 10

Figure 13:
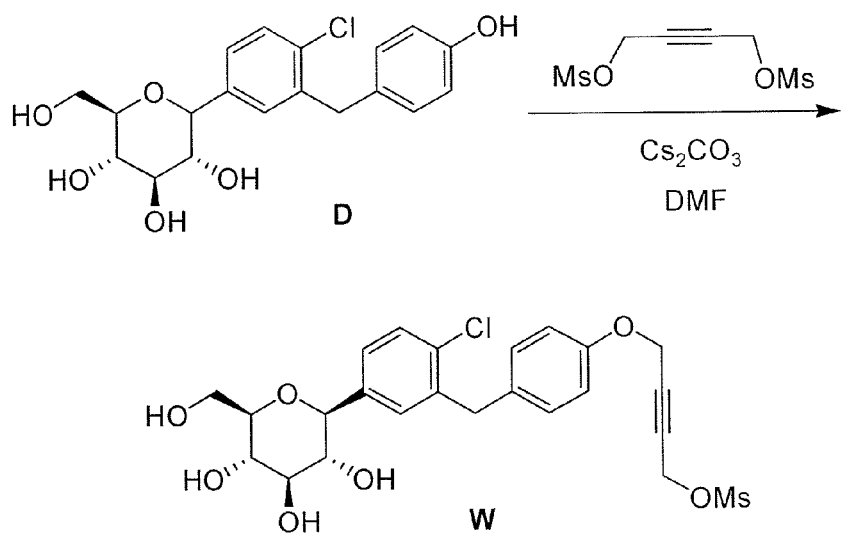
FIG. 13 is the outline for the synthesis of compound W of the invention.

The synthesis of compound W within the invention is outlined in FIG. 13, with the details given below.

Preparation of 4-(4-(2-chloro-5-((2S,3R,4R,5S,6R)-3,4,5-trihydroxy-6-(hydroxymethyl)tetrahydro-2H-pyran-2-yl)benzyl)phenoxy)but-2-ynyl methanesulfonate (Compound W)

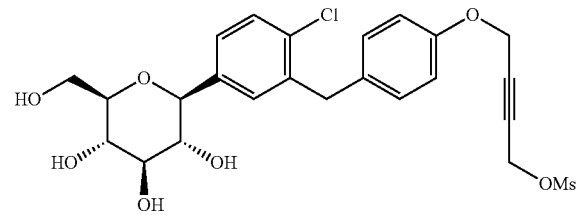

To a solution of (3R,4R,5S,6R)-2-(4-chloro-3-(4-hydroxybenzyl)phenyl)-6-(hydroxymethyl)tetrahydro-2H-pyran-3,4,5-triol (intermediate D) (30 mg) and but-2-yne-1,4-diyl dimethanesulfonate (16.9 mg) in anhydrous DMF (10 mL) was added $Cs_2CO_3$ (51.5 mg). The mixture was stirred overnight at room temperature, whereupon LC-MS showed that intermediate D was exhausted. Then the mixture was poured into water and extracted with EtOAc, washed with water and brine, and dried with anhydrous $Na_2SO_4$. The solvent was then evaporated under reduced pressure, and the crude product was purified by preparative HPLC to obtain compound W (21.36 mg, yield 51.3%). $^1H$ NMR ($CD_3OD$): δ 7.32 (m, 3H), 7.11 (d, J=8.8 Hz, 2H), 6.88 (d, J=8.8 Hz, 2H), 4.93 (t, J=1.2 Hz, 2H), 4.81 (t, J=1.2 Hz, 2H), 4.59 (d, J=3.2 Hz, 1H), 4.18 (m, 1H), 4.02 (m, 4H), 3.94 (m, 1H), 3.83 (m, 1H), 3.67 (m, 1H), 2.99 (s, 3H); MS ESI (m/z): 527 (M+H)+, calc. 526.

Example 11

Figure 14:
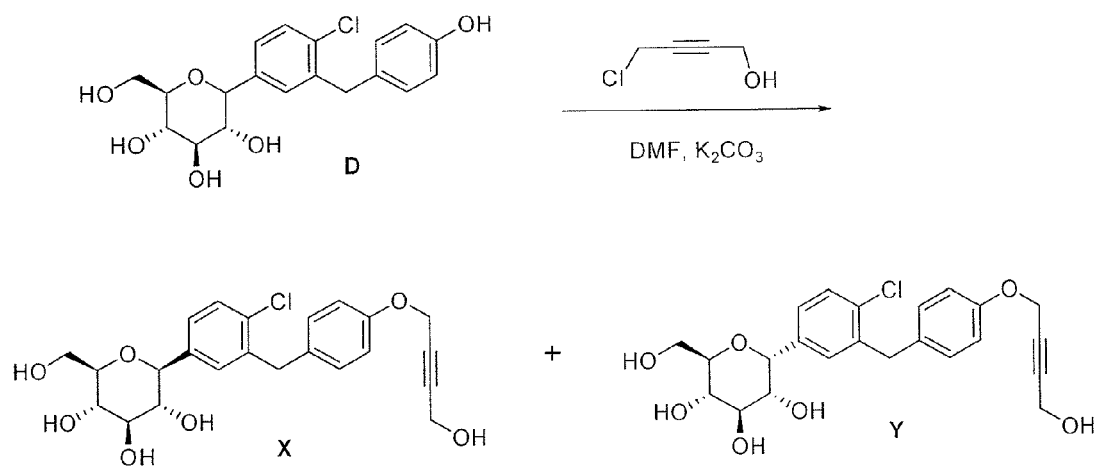
FIG. 14 is the outline for the synthesis of compounds X and Y of the invention.

The synthesis of compounds X and Y within the invention is outlined in FIG. 14, with the details given below.

Preparation of (2S,3R,4R,5S,6R)-2-(4-chloro-3-(4-(4-hydroxybut-2-ynyloxy)benzyl)phenyl)-6-(hydroxymethyl)tetrahydro-2H-pyran-3,4,5-triol (Compound X) and (2R,3R,4R,5S,6R)-2-(4-chloro-3-(4-(4-hydroxybut-2-ynyloxy)benzyl)phenyl)-6-(hydroxymethyl)tetrahydro-2H-pyran-3,4,5-triol (Compound Y)

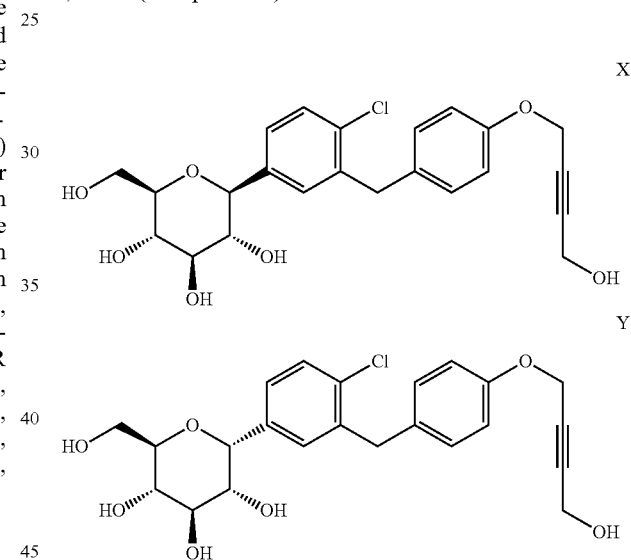

To a solution of (3R,4R,5S,6R)-2-(4-chloro-3-(4-hydroxybenzyl)phenyl)-6-(hydroxymethyl)tetrahydro-2H-pyran-3,4,5-triol (intermediate D) (30 mg) and 4-chlorobut-2-yn-1-ol (16.9 mg) in anhydrous DMF (10 mL) was added $K_2CO_3$ (51.5 mg). The mixture was stirred overnight at room temperature, whereupon LC-MS showed that intermediate D was exhausted. Then the mixture was poured into water and extracted with EtOAc, washed with water and brine, and dried with anhydrous $Na_2SO_4$. The solvent was then evaporated under reduced pressure, and the crude product was purified by preparative HPLC to obtain compounds X (17.68 mg) and Y (10.32 mg). Compound X: $^1H$ NMR ($CD_3OD$): δ 7.32 (m, 3H), 7.11 (d, J=8.8 Hz, 2H), 6.86 (d, J=8.8 Hz, 2H), 4.71 (t, J=1.2 Hz, 2H), 4.19 (t, J=1.2 Hz, 2H), 4.05 (m, 3H), 3.87 (m, 1H), 3.67 (m, 1H), 3.42 (m, 3H), 3.27 (m, 1H); MS ESI (m/z): 449 (M+H)+, calc. 448. Compound Y: $^1H$ NMR ($CD_3OD$): δ 7.32 (m, 3H), 7.13 (d, J=8.8 Hz, 2H), 6.90 (d, J=8.8 Hz, 2H), 4.73 (t, J=1.2 Hz, 2H), 4.58 (d, J=4.0 Hz, 1H), 4.20 (t, J=1.2 Hz, 2H), 4.18 (m, 1H), 4.02 (m, 4H), 3.94 (m, 1H), 3.82 (m, 1H), 3.66 (m, 1H).

Example 12

Figure 15:
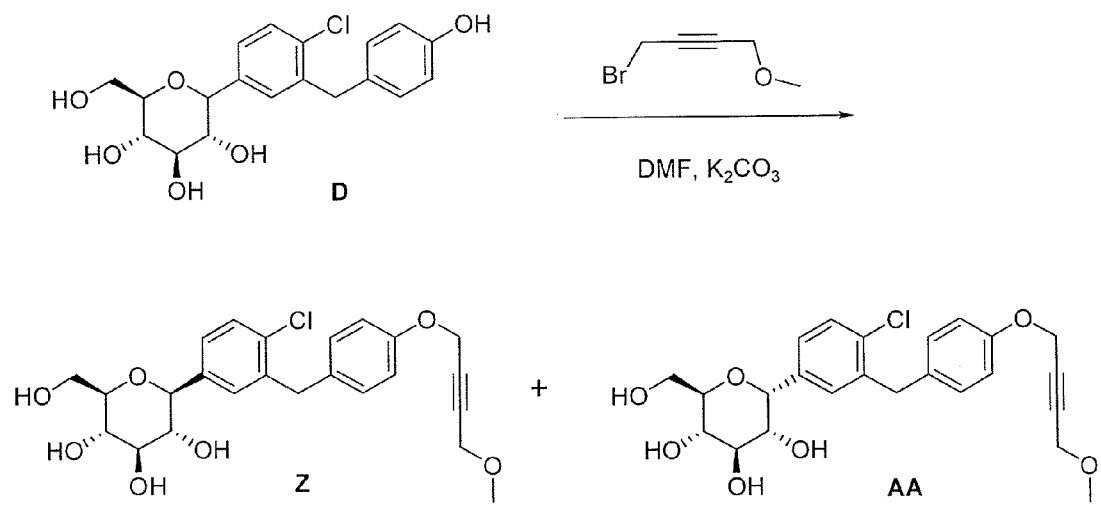
FIG. 15 is the outline for the synthesis of compounds Z and AA of the invention.

The synthesis of compounds Z and AA within the invention is outlined in FIG. 15, with the details given below.

Preparation of (2S,3R,4R,5S,6R)-2-(4-chloro-3-(4-(4-methoxybut-2-ynyloxy)benzyl)phenyl)-6-(hydroxymethyl)tetrahydro-2H-pyran-3,4,5-triol (Compound Z) and (2R,3R,4R,5S,6R)-2-(4-chloro-3-(4-(4-methoxybut-2-ynyloxy)benzyl)phenyl)-6-(hydroxymethyl)tetrahydro-2H-pyran-3,4,5-triol (Compound AA)

Z

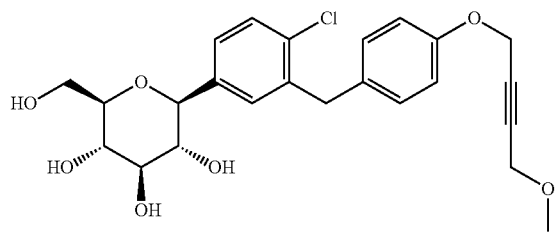

AA

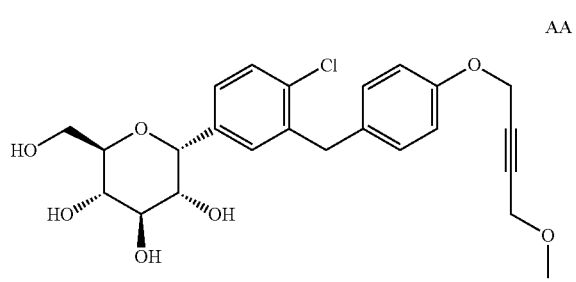

To a solution of (3R,4R,5S,6R)-2-(4-chloro-3-(4-hydroxybenzyl)phenyl)-6-(hydroxymethyl)tetrahydro-2H-pyran-3,4,5-triol (intermediate D) (30 mg) and 1-bromo-4-methoxybut-2-yne (30 mg) in anhydrous DMF (10 mL) was added $K_2CO_3$ (27.1 mg). The mixture was stirred overnight at room temperature, whereupon LC-MS showed that intermediate D was exhausted. Then the mixture was poured into water and extracted with EtOAc, washed with water and brine, and dried with anhydrous $Na_2SO_4$. The solvent was then evaporated under reduced pressure, and the crude product was purified by preparative HPLC to obtain compounds Z (9.68 mg) and AA (5.87 mg). Compound Z: $^1$H NMR (CD$_3$OD): δ 7.30 (m, 3H), 7.11 (d, J=8.8 Hz, 2H), 6.87 (d, J=8.8 Hz, 2H), 4.73 (t, J=1.2 Hz, 2H), 4.58 (d, J=4.0 Hz, 1H), 4.11 (t, J=1.2 Hz, 2H), 4.03 (m, 3H), 3.87 (m, 1H), 3.69 (m, 1H), 3.42 (m, 3H), 3.29 (s, 3H); MS ESI (m/z): 463 (M+H)$^+$, calc. 462. Compound AA: $^1$H NMR (CD$_3$OD): δ 7.30 (m, 3H), 7.11 (d, J=8.8 Hz, 2H), 6.87 (d, J=8.8 Hz, 2H), 4.73 (t, J=1.2 Hz, 2H), 4.57 (s, 2H), 4.56 (t, J=1.2 Hz, 1H), 4.17 (m, 1H), 3.87 (m, 1H), 4.11 (m, 2H), 3.92 (m, 1H), 3.80 (s, 1H), 3.64 (m, 1H), 3.47 (m, 1H), 3.12 (m, 1H).

Example 13

Figure 16:
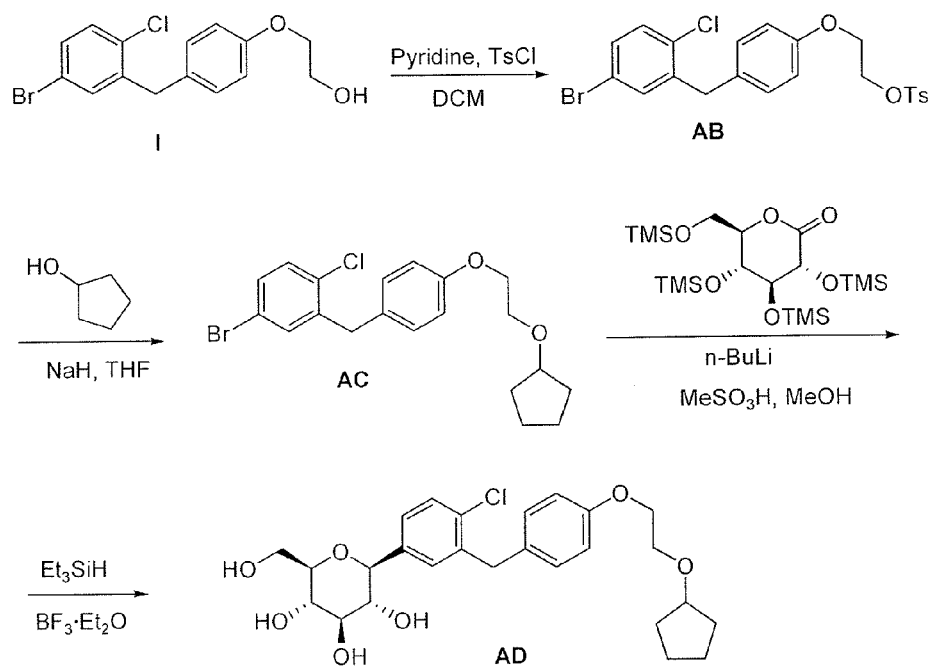
FIG. 16 is the outline for the synthesis of compound AD of the invention.

The synthesis of compound AD within the invention is outlined in FIG. 16, with the details given below.

Preparation of 2-(4-(5-bromo-2-chlorobenzyl)phenoxy)ethyl 4-methylbenzenesulfonate (Intermediate AB)

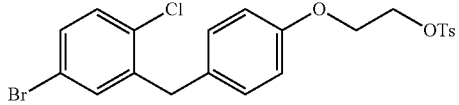

To a solution of 2-(4-(5-bromo-2-chlorobenzyl)phenoxy)ethanol (intermediate I) (3.41 g) in anhydrous DCM (20 mL), pyridine (2.0 eq) was added, and then the mixture was stirred and cooled to 0° C. Then TsCl (1.3 eq) was added in portions, and the mixture was allowed to warmed to room temperature and stirred overnight. TLC (PE:EA=4:1) showed the reaction was complete. Then the mixture was poured into water and extracted with DCM, washed with water and brine, and dried with anhydrous $Na_2SO_4$. The solvent was then evaporated under reduced pressure, and the solid crude product was purified by column chromatography (PE:EA=30:1) to obtain intermediate AB (4.05 g, yield 81.7%).

Prep Preparation of 4-bromo-1-chloro-2-(4-(2-(cyclopentyloxy)ethoxy)benzyl)benzene (Intermediate AC)

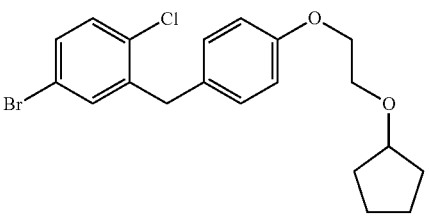

To a solution of cyclopentanol (0.86 g) in anhydrous THF (8.6 mL), NaH (2.0 eq) was added in portions at 0° C., and then the mixture was stirred at 0° C. for 3 h. Then 2-(4-(5-bromo-2-chlorobenzyl)phenoxy)ethyl 4-methylbenzenesulfonate (intermediate AB) (2.43 g, 0.5 eq) was added in portions. The mixture was stirred at room temperature overnight, whereupon TLC showed the reaction was complete. Then the reaction mixture was quenched with saturated NH$_4$Cl, extracted with EtOAc, washed with water and brine, dried with anhydrous $Na_2SO_4$, and concentrated to a crude oil. The crude oil was purified by column chromatography (PE:EA=100:1) to obtain oil AC (1.0 g, yield ~50%).

Preparation of (2S,3R,4R,5S,6R)-2-(4-chloro-3-(4-(2-(cyclopentyloxy)ethoxy)benzyl)phenyl)-6-(hydroxymethyl)tetrahydro-2H-pyran-3,4,5-triol (Compound AD)

To a solution of 4-bromo-1-chloro-2-(4-(2-(cyclopentyloxy)ethoxy)benzyl)benzene (Intermediate AC) (0.41 g) in anhydrous toluene/THF (v/v=2:1, 10 mL), n-BuLi (1.3 eq) was added dropwise at −78° C. and stirred for 1 h. Then the mixture was transferred to a solution of 2,3,4,6-tetra-O-trimethylsilyl-β-D-glucolactone (also called (3R,4S,5R,6R)-3,4, 5-tris(trimethylsilyloxy)-6-((trimethylsilyloxy)methyl)tetrahydro-2H-pyran-2-one) (1.5 eq) in anhydrous toluene (10 mL) at −78° C. The mixture was stirred at −78° C. for 2 h until starting material was consumed. The reaction was quenched with methanesulfonic acid (0.3 g in 10 mL MeOH), and the mixture was allowed to warm to room temperature and stirred overnight. Then 20 mL of water was added. The organic phase was separated, and the water phase was extracted with EtOAc. The organic phases were combined, washed with saturated NaHCO$_3$, water and brine, and then dried with anhydrous Na$_2$SO$_4$, filtered and concentrated. The residue was purified on a flash column (0.8 g, R$_f$=0.1-0.2, EA:PE=2:1) to collect the crude product. The crude product was dissolved in anhydrous CH$_3$CN (10 mL), Et$_3$SiH (1 mL) was added, the mixture was cooled to −5° C., and BF$_3$.Et$_2$O (0.6 mL) was added dropwise. Then the reaction was allowed to warm to 20° C. and stirred overnight. After the reaction reached completion, it was quenched with saturated aqueous NaHCO$_3$. The solvent was removed under reduced pressure and the residue was extracted with EtOAc and washed with water and brine. The product was dried with anhydrous Na$_2$SO$_4$, filtered, concentrated to a solid, and purified by preparative HPLC to obtain compound AD as a white powder upon freeze-drying. $^1$H NMR (CD$_3$OD): δ 7.30 (m, 3H), 7.11 (d, J=8.8 Hz, 2H), 6.87 (d, J=8.8 Hz, 2H), 4.07 (m, 5H), 3.87 (s, 1H), 3.71 (m, 3H), 3.15 (m, 1H), 3.10 (m, 2H), 3.07 (m, 6H), 1.72 (m, 6H), 1.55 (m, 2H); MS ESI (m/z): 494 (M+H)$^+$, calc. 493.

Example 14

Figure 17:
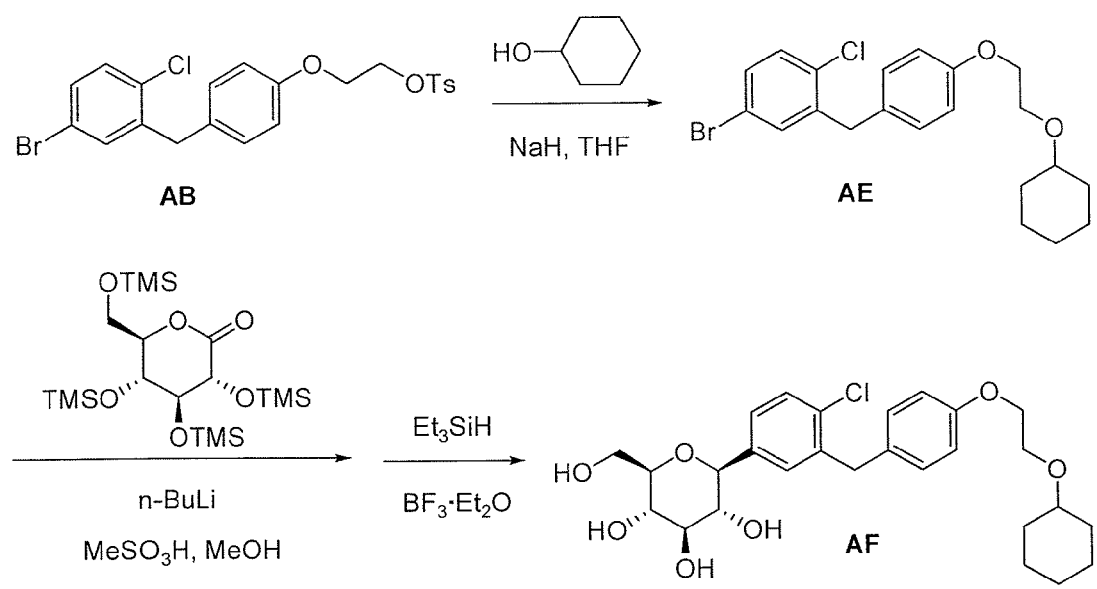
FIG. 17 is the outline for the synthesis of compound AF of the invention.

The synthesis of compound AF within the invention is outlined in FIG. 17, with the details given below.

Preparation of 4-bromo-1-chloro-2-(4-(2-(cyclohexyloxy)ethoxy)benzyl)benzene (Intermediate AE)

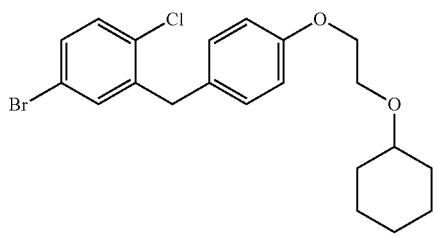

To a solution of cyclohexanol (0.76 g, 7.56 mmol) in anhydrous THF (10 mL), NaH (60%, 0.18 g, 7.56 mmol) was added in portions at 0° C. The mixture was stirred at 0° C. for 0.5 h, and then 2-(4-(5-bromo-2-chlorobenzyl)phenoxy)ethyl 4-methylbenzenesulfonate (intermediate AB) (0.66 g, 1.26 mmol) was added in portions. Then the mixture was stirred at room temperature overnight, whereupon TLC showed the reaction was complete. Then the reaction mixture was quenched with saturated NH$_4$Cl, extracted with EtOAc, washed with water and brine, dried with anhydrous Na$_2$SO$_4$, and concentrated to a crude oil. The crude oil was purified by column chromatography (PE:EA=100:1) to obtain oil AE (0.3 g, yield 56.6%). $^1$H NMR (400 MHz, CD$_3$OD): δ 7.28-7.21 (m, 3H), 7.07 (d, 2H, J=8.8 Hz), 6.86 (d, 2H, J=8.4 Hz), 4.08 (t, 2H, J=4.8 Hz), 3.98 (s, 2H), 3.80 (t, 2H, J=4.8 Hz), 3.40-3.20 (m,1H), 1.95-1.93 (m, 2H), 1.76-1.73 (m, 2H), 1.32-1.22 (m, 6H).

Preparation of (2S,3R,4R,5S,6R)-2-(4-chloro-3-(4-(2-(cyclohexyloxy)ethoxy)benzyl)phenyl)-6-(hydroxymethyl)tetrahydro-2H-pyran-3,4,5-triol (Compound AF)

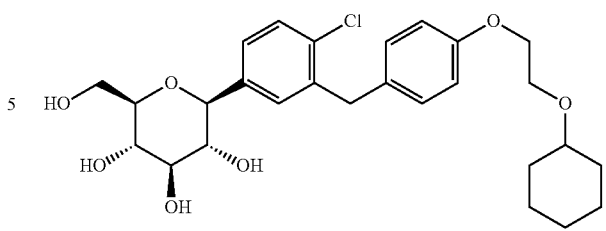

To a solution of 4-bromo-1-chloro-2-(4-(2-(cyclohexyloxy)ethoxy)benzyl)benzene (intermediate AE) (0.3 g, 0.64 mmol) in anhydrous toluene/THF (v/v=2:1, 6 mL), n-BuLi (2.5 N, 0.39 mL, 0.96 mmol) was added dropwise at −78° C. and stirred for 1 h. Then the mixture was transferred to a solution of 2,3,4,6-tetra-O-trimethylsilyl-β-D-glucolactone (also called (3R,4S,5R,6R)-3,4,5-tris(trimethylsilyloxy)-6-((trimethylsilyloxy)methyl)tetrahydro-2H-pyran-2-one) (0.447 g, 0.96 mmol) in anhydrous toluene (5 mL) at −78° C. The mixture was stirred at −78° C. for 2 h until starting material was consumed. The reaction was quenched with methanesulfonic acid (0.3 g in 10 mL MeOH), and the mixture was allowed to warm to room temperature and stirred overnight. Then 20 mL of water was added. The organic phase was separated, and the water phase was extracted with EtOAc. The organic phases were combined, washed with saturated NaHCO$_3$, water and brine, and then dried with anhydrous Na$_2$SO$_4$, filtered and concentrated. The residue was dissolved in anhydrous CH$_3$CN (4 mL), Et$_3$SiH (0.2 mL, 1.25 mmol) was added and the mixture was cooled to −20° C. Then BF$_3$.Et$_2$O (0.12 mL, 0.94 mmol) was added dropwise, and the mixture was allowed to warm to 20° C. and stirred overnight. After the reaction reached completion, it was quenched with saturated aqueous NaHCO$_3$. The solvent was removed under reduced pressure and the residue was extracted with EtOAc and washed with water and brine. The product was dried with anhydrous Na$_2$SO$_4$, filtered, concentrated to a solid, and purified by preparative HPLC to obtain compound AF as a white powder upon freeze-drying. $^1$H NMR (400 MHz, CD$_3$OD): δ 7.37-7.30 (m, 3H), 7.12 (d, 2H, J=8.8 Hz), 6.85 (d, 2H, J=8.8 Hz), 4.11-4.03 (m, 5H), 3.87-3.79 (m, 4H), 3.47-3.33 (m, 4H); 3.32-3.30 (m, 1H), 2.00-1.90 (m, 2H), 1.76-1.75 (m, 2H), 1.60-1.50 (m, 1H), 1.33-1.28 (m, 5H); MS ESI (m/z): 508 (M+H)$^+$, calc. 507.

Example 15

Figure 18:
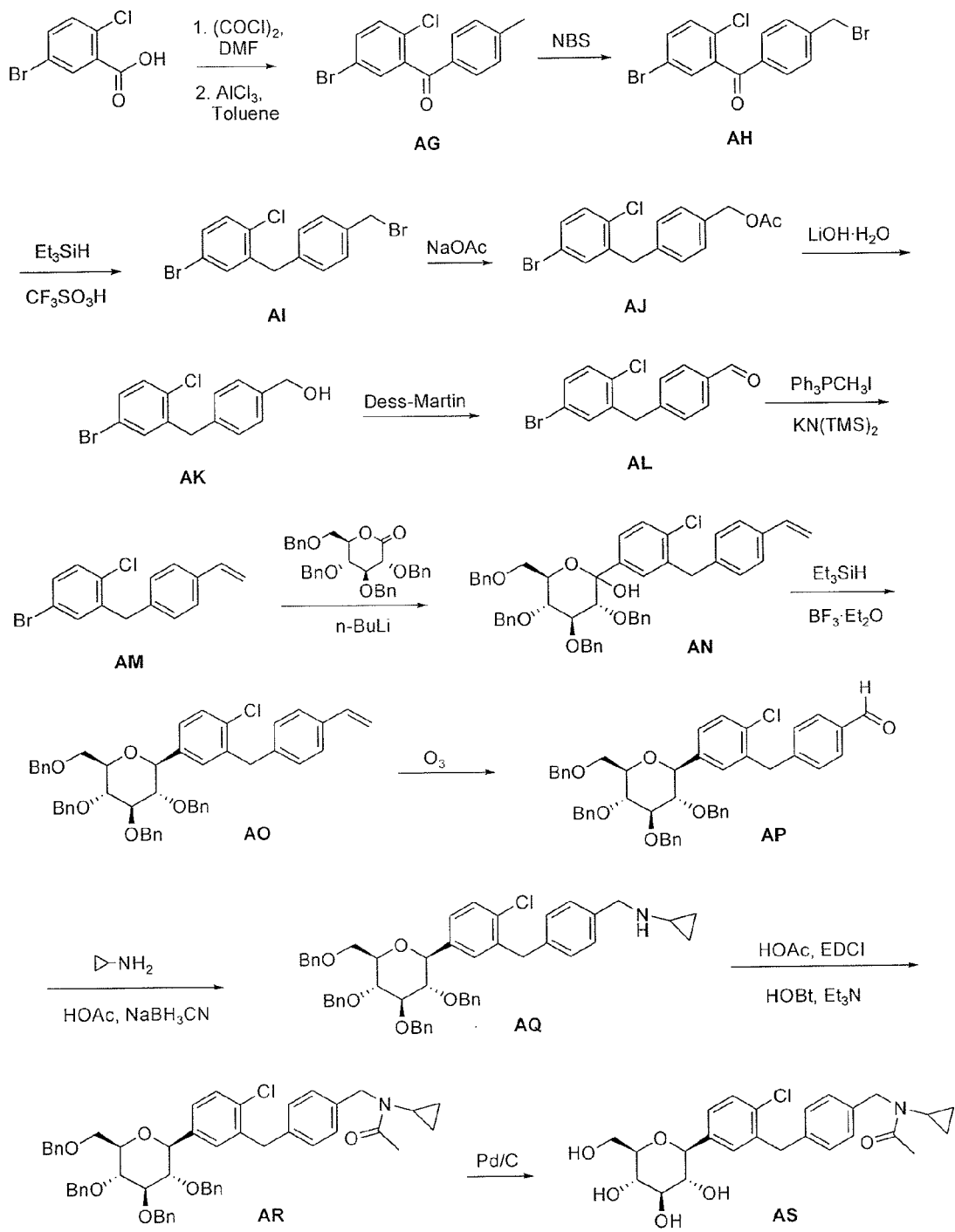
FIG. 18 is the outline for the synthesis of compound AS of the invention.

The synthesis of compound AS within the invention is outlined in FIG. 18, with the details given below.

Preparation of (5-bromo-2-chlorophenyl)(p-tolyl)methanone (Intermediate AG)

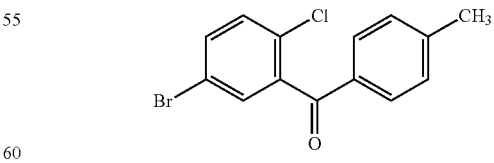

To a stirred suspension of compound 5-bromo-2-chlorobenzoic acid (20 g, 85.5 mmol) in 200 mL of CH$_2$Cl$_2$ containing oxalyl chloride (11.2 mL) was added 0.5 mL of DMF. Once the vigorous evolution of gas ceased, the reaction was stirred overnight and then the volatiles were removed under reduced pressure. After dissolving the crude 5-bromo- 2-chlorobenzoyl chloride in 150 mL of toluene, the solution was cooled to −10° C. Then AlCl$_3$ (22.4 g, 170 mmol) was added while insuring the temperature did not exceed 0° C. HCl gas emission was trapped by passing the gas over a stirred concentrated NaOH solution. HPLC-MS revealed the reaction to be 98% complete after the addition was finished. The reaction was quenched by pouring over ice. The suspension was diluted with H$_2$O and extracted 3× with CH$_2$Cl$_2$. The combined organic extracts were washed 2× with 1N HCl, 1× with H$_2$O, 2× with 1M NaOH, and 2× with brine prior to drying over Na$_2$SO$_4$. After removal of the volatiles, crystallization of the crude product from ethanol (80 mL) yielded intermediate AG (16 g).

Preparation of (5-bromo-2-chlorophenyl)(4-(bromomethyl)phenyl)methanone (Intermediate AH)

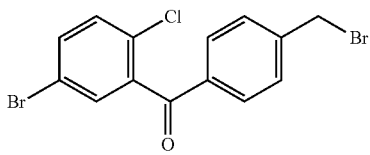

To a solution of (5-bromo-2-chlorophenyl)(p-tolyl)methanone (intermediate AG) (16 g, 48.9 mmol) in CCl$_4$ (80 mL), NBS (10.08 g, 57 mmol) and AIBN (0.848 g) was added. Then the mixture was heated to 90° C. After 3 h, CCl$_4$ was removed under reduced pressure. The residue was dissolved in CH$_2$Cl$_2$ and the solution was washed 1× with HCl (1M) and 2× with brine prior to drying over Na$_2$SO$_4$. Solvent was removed under reduced pressure to obtain crude intermediate AH (20.75 g).

Preparation of 4-bromo-2-(4-(bromomethyl)benzyl)-1-chlorobenzene (Intermediate AI)

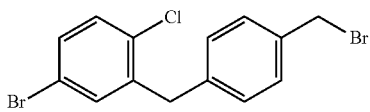

To a stirred solution of Et$_3$SiH (17 mL) and (5-bromo-2-chlorophenyl)(4-(bromomethyl)phenyl)methanone (intermediate AH) (20.75 g, 54 mmol) in TFA (100 mL) at 30° C. was added CF$_3$SO$_3$H (0.05 mL). Within a few minutes the temperature of the solution increased causing it to reflux violently. After 3 h, the volatiles were removed under reduced pressure. The residue was poured into brine and extracted 3× with ethyl acetate. The combined organic layers were washed 3× with H$_2$O, 2× with aqueous Na$_2$SO$_4$ and 2× with brine, and dried over Na$_2$SO$_4$. The solvent was evaporated under reduced pressure, and the product was purified by column chromatography to obtain pure intermediate AI (15.5 g).

Preparation of 4-(5-bromo-2-chlorobenzyl)benzyl acetate (Intermediate AJ)

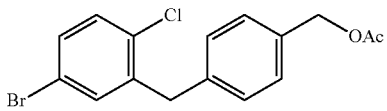

To a solution of 4-bromo-2-(4-(bromomethyl)benzyl)-1-chlorobenzene (intermediate AI) (15.5 g) in DMF (70 mL), NaOAc (16.27 g) was added. The solution was heated to 70° C. After 3 h, H$_2$O (100 mL) and ethyl acetate (200 mL) were added. The organic layer was separated, washed with brine, and dried over Na$_2$SO$_4$. The solvent was evaporated under reduced pressure, and the product was purified by column chromatography to obtain pure intermediate AJ (8.86 g).

Preparation of (4-(5-bromo-2-chlorobenzyl)phenyl)methanol (Intermediate AK)

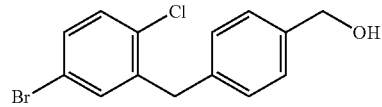

To a solution of 4-(5-bromo-2-chlorobenzyl)benzyl acetate (intermediate AJ) (8.86 g) in 60 mL of a mixture of THF:MeOH:H$_2$O (v/v/v=2:3:1), LiOH.H$_2$O (2.10 g) was added. The solution was stirred at room temperature. After 1 h, H$_2$O (10 mL) and ethyl acetate (100 mL) were added. The aqueous layer was extracted 2× with ethyl acetate. The combined ethyl acetate layers were washed with brine and dried over Na$_2$SO$_4$. The solvent was evaporated under reduced pressure, and the product was purified by column chromatography to obtain pure intermediate AK (6 g).

Preparation of 4-(5-bromo-2-chlorobenzyl)benzaldehyde (Intermediate AL)

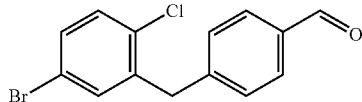

To a solution of (4-(5-bromo-2-chlorobenzyl)phenyl)methanol (intermediate AK) (1 g) in CH$_2$Cl$_2$ (10 mL), the solution of Dess-Martin periodinane (DMP) (1.22 g) in CH$_2$Cl$_2$ (10 mL) was added dropwise at 0° C. The mixture was warmed to room temperature, and the reaction was monitored by TLC. After 1 h, CH$_2$Cl$_2$ was added to dilute the solution and 1 M NaOH was added to quench the reaction. The CH$_2$Cl$_2$ layer was separated and washed with aqueous NaHSO$_3$ and brine, and dried over Na$_2$SO$_4$. The solvent was evaporated under reduced pressure, and the product was purified by column chromatography to obtain pure intermediate AL (0.62 g).

Preparation of 4-bromo-1-chloro-2-(4-vinylbenzyl)benzene (Intermediate AM)

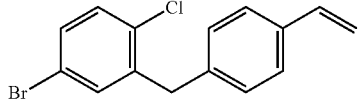

To a solution of Ph$_3$PCH$_3$I (0.97 g) in toluene (5 mL), KN(TMS)$_2$ (0.5M in toluene, 4.8 mL) was added dropwise at room temperature. After 10 min, the solution of 4-(5-bromo-2-chlorobenzyl)benzaldehyde (intermediate AL) (0.62 g) in toluene (2 mL) was added dropwise. After 2 h, aqueous NaHCO$_3$ was added to quench the reaction, and the resulting mixture was extracted with ethyl acetate. The organic layers were combined, washed with brine, and dried over Na$_2$SO$_4$. The solvent was evaporated under reduced pressure, and the product was purified by column chromatography to obtain pure intermediate AM (0.5 g).

Preparation of (3R,4S,5R,6R)-3,4,5-tris(benzyloxy)-6-(benzyloxymethyl)-2-(4-chloro-3-(4-vinylbenzyl)phenyl)tetrahydro-2H-pyran-2-ol (Intermediate AN)

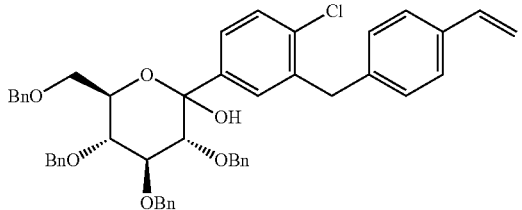

To a solution of 4-bromo-1-chloro-2-(4-vinylbenzyl)benzene (intermediate AM) (215 mg) in toluene:THF (2:1) (3 mL) at −78° C. was added n-BuLi (0.34 mL, 2.5 M in hexane) dropwise. After 45 min, the above mixture was added dropwise into a pre-cooled (−78° C.) solution of (3R,4S,5R,6R)-3,4,5-tris(benzyloxy)-6-(benzyloxymethyl)tetrahydro-2H-pyran-2-one (453 mg) in toluene (3 mL). After being stirred for 2.5 h at −78° C., the reaction mixture was quenched by saturated NH$_4$Cl and diluted with ethyl acetate. The organic layer was separated, washed with brine and dried over Na$_2$SO$_4$. Concentration gave the crude product which was purified by chromatography to provide intermediate AN (712 mg) as an oil.

Preparation of (2R,3R,4R,5S,6S)-3,4,5-tris(benzyloxy)-2-(benzyloxymethyl)-6-(4-chloro-3-(4-vinylbenzyl)phenyl)tetrahydro-2H-pyran (Intermediate AO)

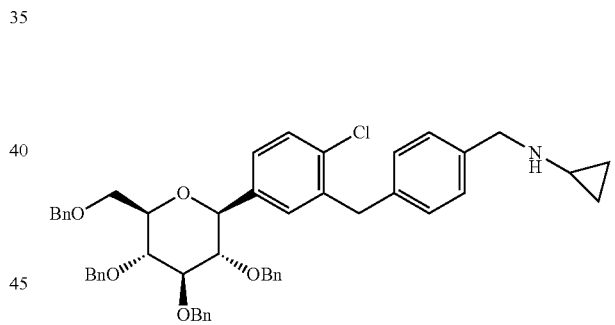

To a stirred solution of (3R,4S,5R,6R)-3,4,5-tris(benzyloxy)-6-(benzyloxymethyl)-2-(4-chloro-3-(4-vinylbenzyl)phenyl)tetrahydro-2H-pyran-2-ol (intermediate AN) (350 mg) in 4 mL of CH$_2$Cl$_2$:CH$_3$CN (1:1) at −15° C. was added Et$_3$SiH (0.146 mL), followed by BF$_3$.Et$_2$O (0.09 mL). During the period of addition, the temperature was maintained at approximately −5° C. to −10° C. The stirred solution was allowed to warm to 0° C. over 5 h. The reaction was monitored by TLC, and after the starting material was consumed, the reaction was quenched by addition of saturated aqueous NaHCO$_3$. The solvent was removed under reduced pressure. The residue was then dissolved in a mixture of 40 mL of ethyl acetate and water (1:1). After separation of the organic layer, the aqueous phase was extracted 2× with 20 mL of ethyl acetate. The organic phases were combined and washed with brine and water before drying over Na$_2$SO$_4$. Concentration of the solution yielded a yellow gel, which was purified by preparative TLC to obtain pure intermediate AO (100 mg).

Preparation of 4-(2-chloro-5-((2S,3S,4R,5R,6R)-3,4,5-tris(benzyloxy)-6-(benzyloxymethyl)tetrahydro-2H-pyran-2-yl)benzyl)benzaldehyde (Intermediate AP)

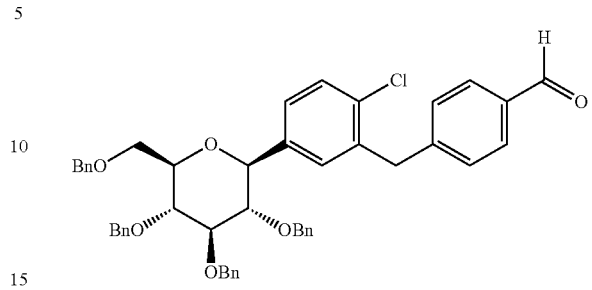

Into a solution of (2R,3R,4R,5S,6S)-3,4,5-tris(benzyloxy)-2-(benzyloxymethyl)-6-(4-chloro-3-(4-vinylbenzyl)phenyl)tetrahydro-2H-pyran (intermediate AO) (100 mg) in CH$_2$Cl$_2$ (10 mL) at −78° C. was bubbled O$_3$ until the color of the solution turned blue. After TLC showed the starting material was consumed, a solution of PPh$_3$ (70 mg) in CH$_2$Cl$_2$ (2 mL) was added dropwise at −78° C. The solution was then warmed to room temperature over a period of 1 h. The precipitate was removed by filtration, and solvent was removed from the filtrate under reduced pressure. The crude product was purified by preparative TLC to obtain intermediate AP (83 mg). MS ESI (m/z): 770 (M+NH$_4$)$^+$.

Preparation of N-(4-(2-chloro-5-((2S,3S,4R,5R,6R)-3,4,5-tris(benzyloxy)-6-(benzyloxymethyl)tetrahydro-2H-pyran-2-yl)benzyl)benzyl)cyclopropanamine (Intermediate AQ)

A solution of 4-(2-chloro-5-((2S,3S,4R,5R,6R)-3,4,5-tris(benzyloxy)-6-(benzyloxymethyl)tetrahydro-2H-pyran-2-yl)benzyl)benzaldehyde (intermediate AP) (40 mg) in CH$_2$Cl$_2$:CH$_3$CN (v/v=1:1) (1.0 mL) was cooled to 0° C., followed by addition of cyclopropylamine (15 mg) and acetic acid (1 mg). After 30 min, NaBH$_3$CN (17 mg) was added. The reaction was monitored by LC-MS. After the starting material was consumed, ethyl acetate (20 mL) and water (5 mL) were added to quench the reaction. The organic layer was separated and the aqueous layer was extracted with ethyl acetate. The organic extracts were combined and washed with brine. Removal of ethyl acetate under reduced pressure and purification of the crude product by preparative TLC gave intermediate AQ (30 mg). MS ESI (m/z): 794 (M+H)$^+$.

Preparation of N-(4-(2-chloro-5-((2S,3S,4R,5R,6R)-3,4,5-tris(benzyloxy)-6-(benzyloxymethyl)tetrahydro-2H-pyran-2-yl)benzyl)benzyl)-N-cyclopropylacetamide (Intermediate AR)

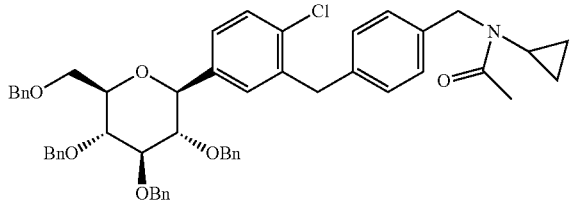

To a solution of acetic acid (0.11 g) and Et₃N (0.14 mL) in CH₂Cl₂ (1 mL) at room temperature, EDCI (96 mg) and HOBt (68 mg) was added. The mixture was stirred for 30 min at room temperature. A solution of N-(4-(2-chloro-5-((2S,3S,4R,5R,6R)-3,4,5-tris(benzyloxy)-6-(benzyloxymethyl)tetrahydro-2H-pyran-2-yl)benzyl)benzyl)cyclopropanamine (Intermediate AQ) (40 mg) in CH₂Cl₂ (0.2 mL) was added dropwise. The reaction was monitored by LC-MS. After the starting material was consumed, CH₂Cl₂ was added to dilute the solution. The resulting mixture was then washed with H₂O, 1N HCl, aqueous NaHCO₃ and brine. CH₂Cl₂ was removed under reduced pressure, and the crude product was purified by preparative TLC to give intermediate AR (20 mg). MS ESI (m/z): 836 (M+H)⁺, 853 (M+NH₄)⁺.

Preparation of N-(4-(2-chloro-5-((2S,3R,4R,5S,6R)-3,4,5-trihydroxy-6-(hydroxymethyl)tetrahydro-2H-pyran-2-yl)benzyl)benzyl)-N-cyclopropylacetamide (Compound AS)

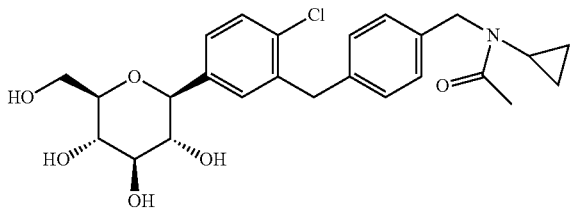

To a solution of N-(4-(2-chloro-5-((2S,3S,4R,5R,6R)-3,4,5-tris(benzyloxy)-6-(benzyloxymethyl)tetrahydro-2H-pyran-2-yl)benzyl)benzyl)-N-cyclopropylacetamide (intermediate AR) (20 mg) in THF:CH₃OH (v/v=1:1) (4 mL) at room temperature was added Pd/C and 1,2-dichlorbenzene (0.05 mL). The mixture was stirred under H₂. After LC-MS showed the starting material was consumed, Pd/C was removed by filtration, and the solvent was removed under reduced pressure. The crude product was purified by preparative LC-MS to give compound AS (4 mg). ¹H NMR (400 Hz, CD₃OD): δ 0.77-0.87 (4H, m), 2.26 (3H, s), 2.62-2.66 (1H, m), 3.26 (1H, d, J=8.8 Hz), 3.36-3.46 (3H, m), 3.66-3.69 (1H, m), 3.86 (1H, d, J=12.8 Hz), 4.02-4.12 (3H, m), 4.56 (2H, s), 7.11-7.16 (4H, m), 7.26-7.29 (1H, m), 7.33-7.35 (2H, m); MS ESI (m/z): 520 (M+HCO₂)⁻.

Example 16

Figure 19:
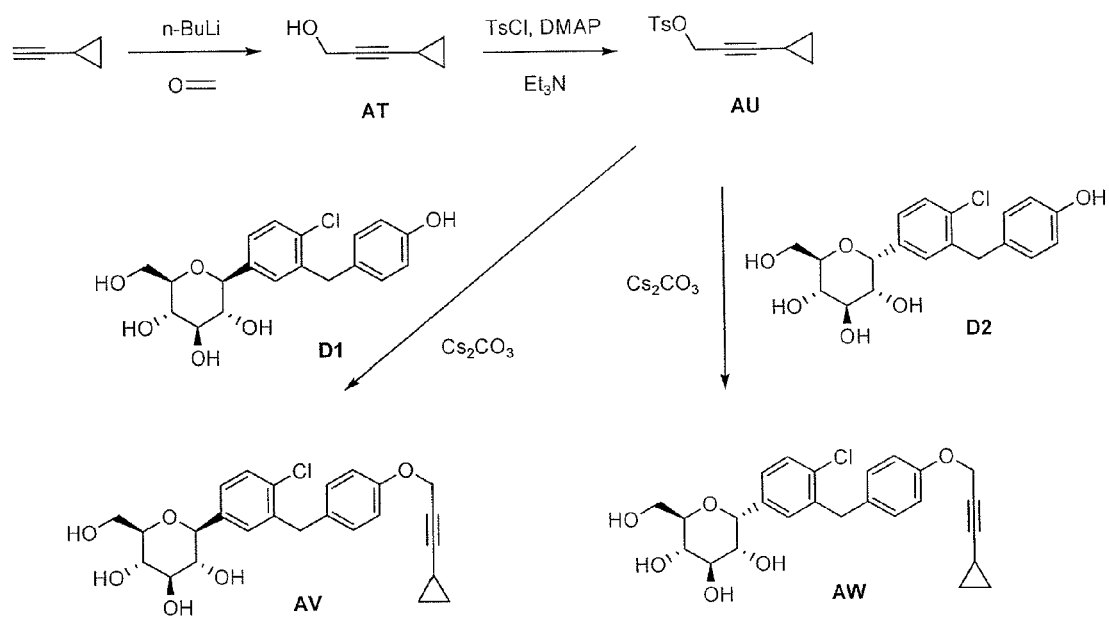
FIG. 19 is the outline for the synthesis of compounds AV and AW of the invention.

The synthesis of compounds AV and AW within the invention is outlined in FIG. 19, with the details given below.

Preparation of 3-cyclopropylprop-2-yn-1-ol (Intermediate AT)

Under Ar, n-butyllithium in hexane (3.33 mL, 2.5 M, 8.33 mmol) was added dropwise to a solution of ethynylcyclopropane (0.5 g, 7.58 mmol) in anhydrous THF (5 mL) at 0° C. The solution was stirred for 1 h after the addition was completed. To this solution, paraformaldehyde (0.273 g, 9.09 mmol) was added. The mixture was stirred for 1 h at 0° C., and allowed to warm to room temperature for another 2h. The reaction was gradually quenched with 6N HCl (2 mL) in an ice bath. The aqueous layer was extracted twice with 20 mL of ethyl acetate. The organic layer was washed with saturated NaHCO₃ solution and water prior to drying over anhydrous Na₂SO₄. The organic phase was concentrated to give crude intermediate AT (550 mg), which was used in the next step without purification.

Preparation of 3-cyclopropylprop-2-ynyl 4-methylbenzenesulfonate (Intermediate AU)

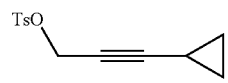

To a stirred solution of crude 3-cyclopropylprop-2-yn-1-ol (intermediate AT) (0.55 mg) in 10 mL of CH₂Cl₂ was added TsCl (1.33 g, 6.87 mmol) and DMAP (0.035 g, 0.2865 mmol) at 0° C. Triethylamine (0.96 mL, 6.87 mmol) was added dropwise to the mixture and the reaction temperature was held so as not to exceed 0° C. After stirring for 3h, the mixture was quenched with 10 mL of water. The aqueous layer was extracted twice with 20 mL each of CH₂Cl₂. The organic layer was washed with 20% HCl and water prior to drying over anhydrous Na₂SO₄. The organic phase was concentrated and the crude product was purified by gel column chromatography to obtain intermediate AU (0.4 g).

Preparation of (2S,3R,4R,5S,6R)-2-(4-chloro-3-(4-(3-cyclopropylprop-2-ynyloxy)benzyl)phenyl)-6-(hydroxymethyl)tetrahydro-2H-pyran-3,4,5-triol (Compound AV)

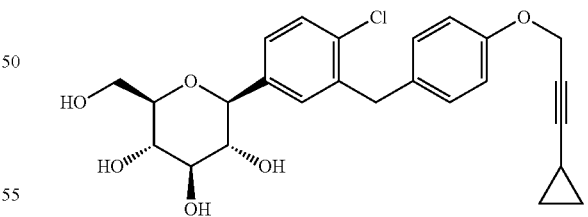

To a stirred solution of (2S,3R,4R,5S,6R)-2-(4-chloro-3-(4-hydroxybenzyl)phenyl)-6-(hydroxymethyl)tetrahydro-2H-pyran-3,4,5-triol (intermediate D1) (20 mg, 0.0526 mmol) in 1 mL of DMF was added Cs₂CO₃ (21 ng, 0.063 mmol) and 3-cyclopropylprop-2-ynyl 4-methylbenzenesulfonate (intermediate AU) (20 mg, 0.079 mmol) at room temperature. After stirring for 2 h, the reaction was quenched with 1 mL of ice water. The mixture was extracted 3× with ethyl acetate (5 mL each). The combined organic layers were washed 2× with water (5 mL each) and brine prior to drying over Na₂SO₄. Concentration of the solution and purification of the crude product by preparative LC-MS afforded compound AV (10 mg). ¹H NMR (CD₃OD): δ 7.37~7.34 (2H, m), 7.30~7.28 (1H, dd, J=8.8, 2 Hz), 7.13~7.11 (2H, d, J=8.8 Hz), 6.87~6.83 (2H, d, J=8.8 Hz), 4.61 (2H, d, J=2 Hz), 4.11 (1H, d, J=9.2 Hz), 4.10~4.04 (2H, dd, J=23.6, 14.8 Hz), 3.90~3.87 (1H, m), 3.72~3.68 (1H, m), 3.49~3.39 (3H, m), 3.31~3.28 (1H, m), 1.31~1.24 (1H, m), 0.79~0.75 (2H, m), 0.62~0.59 (2H, m).

Preparation of (2R,3R,4R,5S,6R)-2-(4-chloro-3-(4-(3-cyclopropylprop-2-ynyloxy)benzyl)phenyl)-6-(hydroxymethyl)tetrahydro-2H-pyran-3,4,5-triol (Compound AW)

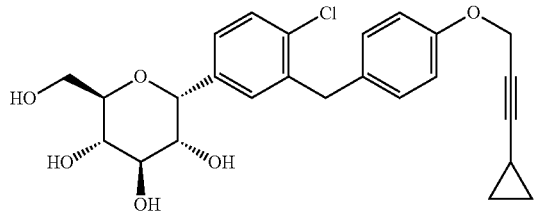

Compound AW was prepared by reaction of (2R,3R,4R,5S,6R)-2-(4-chloro-3-(4-hydroxybenzyl)phenyl)-6-(hydroxymethyl)tetrahydro-2H-pyran-3,4,5-triol (intermediate D2) with 3-cyclopropylprop-2-ynyl 4-methylbenzenesulfonate (intermediate AU) in the presence of Cs₂CO₃ using the same procedure as described above for compound AV. ¹H NMR (CD₃OD): δ 7.34~7.30 (3H, m), 7.11~7.08 (2H, d, J=8.8 Hz), 6.86~6.84 (2H, d, J=8.8 Hz), 4.61 (2H, d, J=1.6 Hz), 4.58 (1H, d, J=4 Hz), 4.19~4.17 (1H, m), 4.03~4.00 (4H, m), 3.94~3.93 (1H, q), 3.84~3.80 (1H, m), 3.68~3.64 (1H, q), 1.29~1.24 (1H, m), 0.78~0.75 (2H, m), 0.62~0.59 (2H, m).

Example 17

Figure 20:
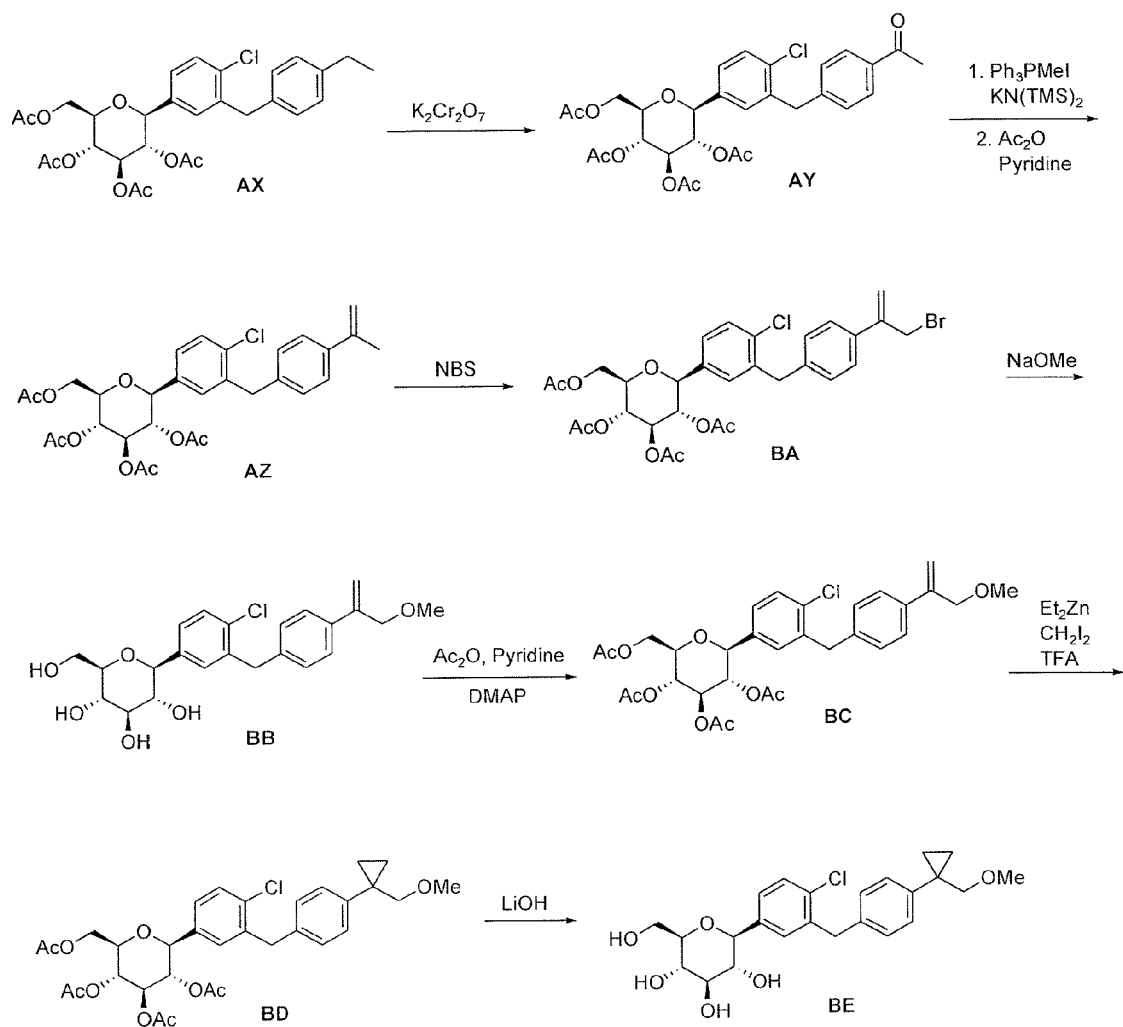
FIG. 20 is the outline for the synthesis of compound BE of the invention.

The synthesis of compound BE within the invention is outlined in FIG. 20, with the details given below.

Preparation of (2R,3R,4R,5S,6S)-2-(acetoxymethyl)-6-(3-(4-acetylbenzyl)-4-chlorophenyl)tetrahydro-2H-pyran-3,4,5-triyl triacetate (Intermediate AY)

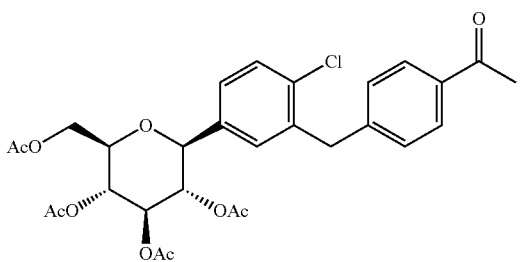

To a stirred solution of (2R,3R,4R,5S,6S)-2-(acetoxymethyl)-6-(4-chloro-3-(4-ethylbenzyl)phenyl)tetrahydro-2H-pyran-3,4,5-triyl triacetate (intermediate AX) (10 g, 10.83 mmol) (prepared by methods analogous to those described in US20040138439) in AcOH (130 mL) at 120° C. was added K₂CrO₇ (6.3 g, 21.42 mmol) in one portion. The mixture was stirred for 22 h at the same temperature. Volatiles were removed under reduced pressure, AcOEt was added, and the solids were removed by filtration. The organic layer was washed with a saturated solution of NaHCO₃ and brine prior to drying over Na₂SO₄. Concentration of the organic solution and purification of the resulting residue by silical gel column (PE:EA=3:1) provided intermediate AY (2.3 g).

Preparation of (2R,3R,4R,5S,6S)-2-(acetoxymethyl)-6-(4-chloro-3-(4-(prop-1-en-2-yl)benzyl)phenyl)tetrahydro-2H-pyran-3,4,5-triyl triacetate (Intermediate AZ)

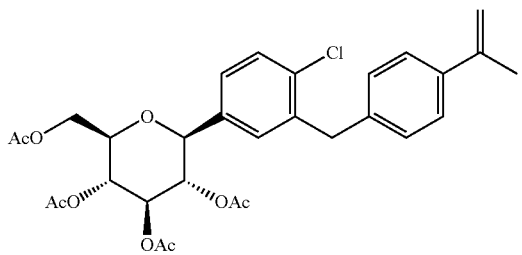

To a solution of Ph₃PMeI (378 mg, 0.935 mmol) in toluene (3 mL) was added KN(TMS)₂ (0.5 M, 1.8 mL) dropwise. After stirring for 40 min, (2R,3R,4R,5S,6S)-2-(acetoxymethyl)-6-(3-(4-acetylbenzyl)-4-chlorophenyl)tetrahydro-2H-pyran-3,4,5-triyl triacetate (intermediate AY) (360 mg, 0.626 mmol) in toluene (5 mL) was added. After stirring overnight, the reaction was quenched with a saturated solution of NaHCO₃. The mixture was extracted 3× with AcOEt. The combined organic extracts were washed 1× with brine prior to drying over Na₂SO₄. Concentration of the solution gave an oily residue, which was redissolved in 3 mL of CH₂Cl₂, and then 0.2 mL of pyridine (2.47 mmol), 0.23 mL of Ac₂O (2.44 mmol) and DMAP (catalytic quantity) were added. The mixture was stirred for 2 h at room temperature. Additional CH₂Cl₂ (20 mL) was added, the mixture was washed 2× with 1N HCl and 1× with brine prior to drying over Na₂SO₄. Concentration of the solution and purification of the crude product by silical gel column gave intermediate AZ (286 mg).

Preparation of (2R,3R,4R,5S,6S)-2-(acetoxymethyl)-6-(3-(4-(3-bromoprop-1-en-2-yl)benzyl)-4-chlorophenyl)tetrahydro-2H-pyran-3,4,5-triyl triacetate (Intermediate BA)

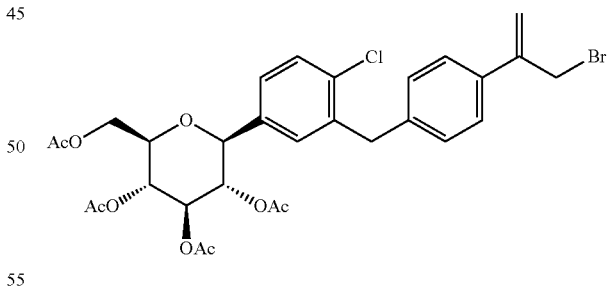

A mixture of (2R,3R,4R,5S,6S)-2-(acetoxymethyl)-6-(4-chloro-3-(4-(prop-1-en-2-yl) benzyl)phenyl)tetrahydro-2H-pyran-3,4,5-triyl triacetate (intermediate AZ) (236 mg, 0.412 mmol) and NBS (110 mg, 0.618 mmol) in chlorobenzene (5 mL) was stirred at 135° C. for 2 h. The solids were filtered and washed with AcOEt. The organic portion was washed 1× with H₂O and 1× with brine prior to drying over Na₂SO₄. Concentration and purification of the resulting residue by preparative TLC gave intermediate AZ (144 mg).

Preparation of (2S,3R,4R,5S,6R)-2-(4-chloro-3-(4-(3-methoxyprop-1-en-2-yl)benzyl)phenyl)-6-(hydroxymethyl)tetrahydro-2H-pyran-3,4,5-triol (Intermediate BB)

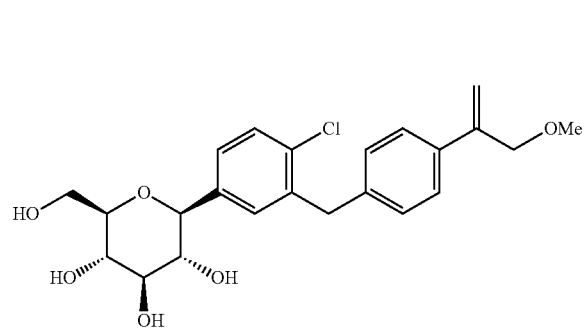

The solution of (2R,3R,4R,5S,6S)-2-(acetoxymethyl)-6-(3-(4-(3-bromoprop-1-en-2-yl)benzyl)-4-chlorophenyl)tetrahydro-2H-pyran-3,4,5-triyl triacetate (intermediate BA) (110 mg, 0.169 mmol) and 4 mL of 0.3M NaOMe in MeOH (freshly-distilled) was stirred at 70° C. for 2.5 h. Then the reaction was quenched with $H_2O$. After removing the volatiles, the aqueous layer was extracted 3× with AcOEt. The organic portion was washed 1× with a saturated solution of $NH_4Cl$ and 1× with brine prior to drying over $Na_2SO_4$. Concentration and purification of the crude product by preparative TLC gave intermediate BA (48 mg).

Preparation of (2R,3R,4R,5S,6S)-2-(acetoxymethyl)-6-(4-chloro-3-(4-(3-methoxyprop-1-en-2-yl)benzyl)phenyl)tetrahydro-2H-pyran-3,4,5-triyl triacetate (Intermediate BC)

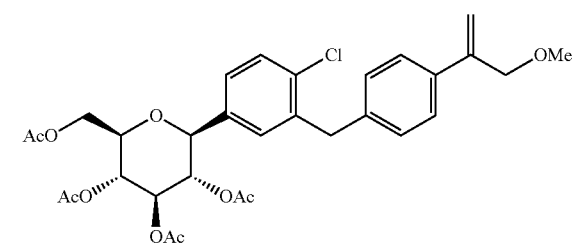

To a solution of (2S,3R,4R,5S,6R)-2-(4-chloro-3-(4-(3-methoxyprop-1-en-2-yl)benzyl)phenyl)-6-(hydroxymethyl)tetrahydro-2H-pyran-3,4,5-triol (intermediate BB) (48 mg, 0.11 mmol) in $CH_2Cl_2$ (1 mL) was added pyridine (0.1 mL, 1.06 mmol) followed by $Ac_2O$ (0.09 mL, 1.11 mmol) and DMAP (catalytic quantity) added in one portion. The mixture was stirred overnight at room temperature. Then 20 mL of $CH_2Cl_2$ was added, and the mixture was washed 2× with 1N HCl and 1× with brine prior to drying over $Na_2SO_4$. Concentration and purification of the crude product by preparative TLC afforded intermediate BC (32 mg).

Preparation of (2R,3R,4R,5S,6S)-2-(acetoxymethyl)-6-(4-chloro-3-(4-(1-(methoxymethyl)cyclopropyl)benzyl)phenyl)tetrahydro-2H-pyran-3,4,5-triyl triacetate (Intermediate BD)

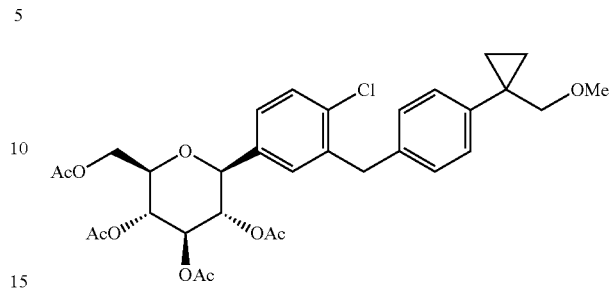

To a cooled (0° C.) solution of $ZnEt_2$ (0.16 mL, 0.16 mmol) in $CH_2Cl_2$ (0.4 mL) was added a solution of TFA (12 µL, 0.16 mmol) in $CH_2Cl_2$ (0.2 mL). After stirring for 20 min, a solution of $CH_2I_2$ (43 mg, 0.16 mmol) in $CH_2Cl_2$ (0.2 mL) was added. After stirring for an additional 20 min, a solution of (2R,3R,4R,5S,6S)-2-(acetoxymethyl)-6-(4-chloro-3-(4-(3-methoxyprop-1-en-2-yl)benzyl)phenyl)tetrahydro-2H-pyran-3,4,5-triyl triacetate (intermediate BC) (32 mg, 0.053 mmol) in $CH_2Cl_2$ (0.4 mL) was added. The mixture was stirred overnight prior to quenching with a saturated solution of $NaHCO_3$. The mixture was extracted 3× with $CH_2Cl_2$, and the organic portion was washed with brine prior to drying over $Na_2SO_4$. Concentration of the solution gave crude intermediate BC (25 mg).

Preparation of (2S,3R,4R,5S,6R)-2-(4-chloro-3-(4-(1-(methoxymethyl)cyclopropyl)benzyl)phenyl)-6-(hydroxymethyl)tetrahydro-2H-pyran-3,4,5-triol (Compound BE)

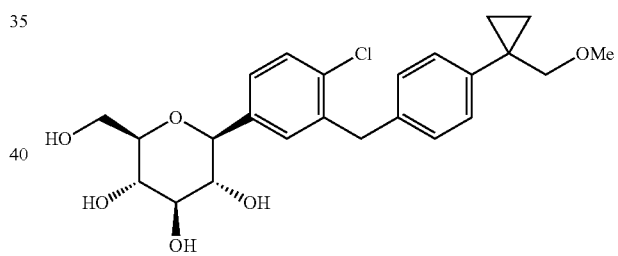

To a solution of the above crude (2R,3R,4R,5S,6S)-2-(acetoxymethyl)-6-(4-chloro-3-(4-(1-(methoxymethyl)cyclopropyl)benzyl)phenyl)tetrahydro-2H-pyran-3,4,5-triyl triacetate (intermediate BD) (25 mg) in $THF:MeOH:H_2O$ (2:3:1) (1 mL) was added $LiOH.H_2O$ (4.66 mg). After stirring for about 2.5 h, the volatiles were removed with a rotary evaporator. The residue was taken up with water (5 mL) and AcOEt (20 mL), the organic layer was separated, and the aqueous layer was extracted 3× with AcOEt. The combined organic phase was washed 1× with brine prior to drying over $Na_2SO_4$. Concentration and purification of the crude product by preparative HPLC afforded compound BE (7.5 mg). $^1H$ NMR ($CD_3OD$, 400 MHz) δ 7.35-7.33 (m, 2H), 7.27 (dd, J=8.0, 2.0 Hz, 1H), 7.21 (d, J=8.4 Hz, 2H), 7.10 (d, J=8.4 Hz, 2H), 4.11-4.01 (m, 3H), 3.87 (d, J=9.6 Hz, 1H), 3.70-3.66 (m, 1H), 3.48 (s, 2H), 3.45-3.34 (m, 4H), 3.26 (s, 3H), 0.83-0.82 (m, 4H); MS ESI (m/z): 449 $(M+H)^+$, 466 $(M+NH_4)^+$, 493 $(M+HCO_2)^-$.

Example 18

Figure 21:
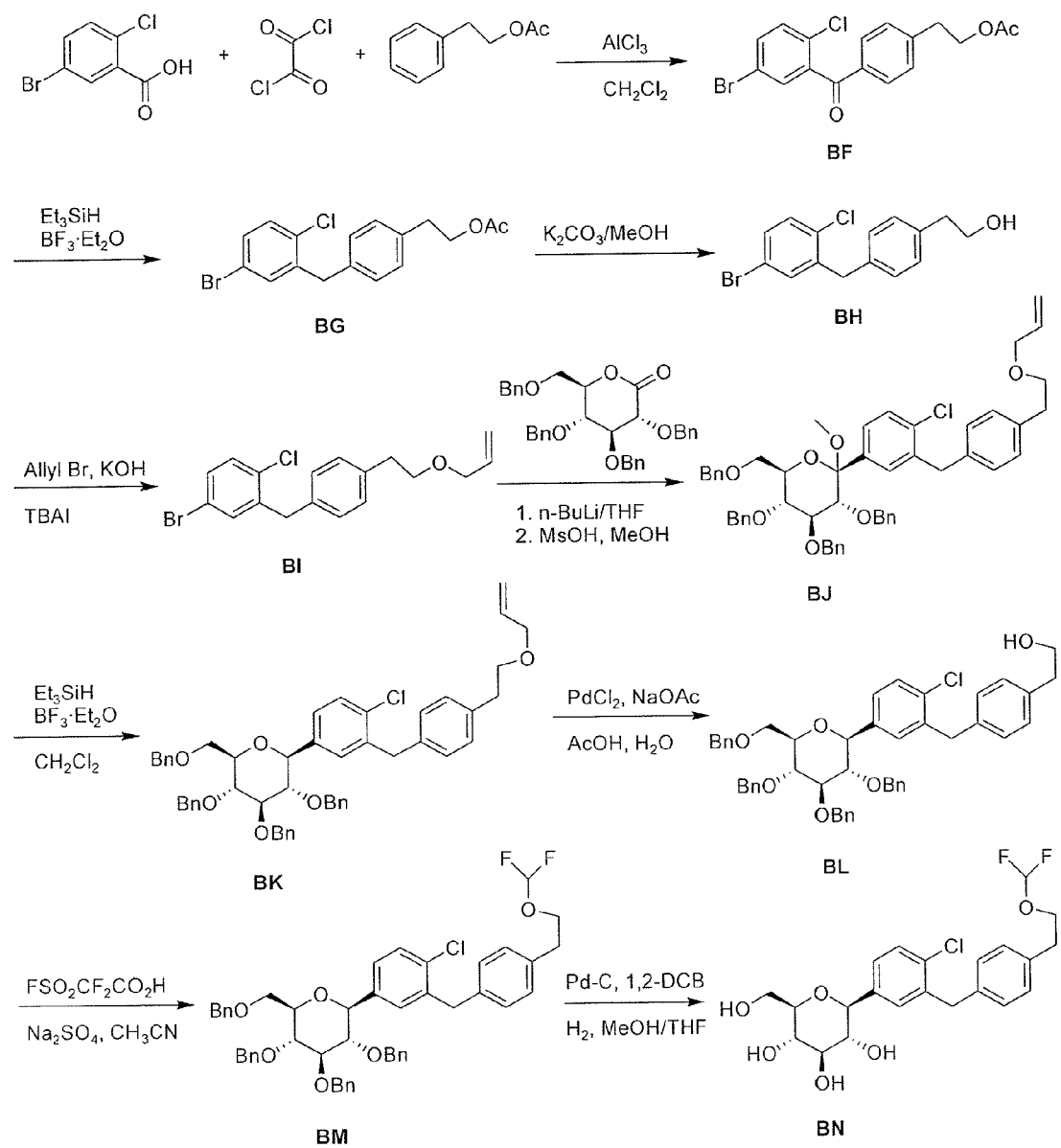
FIG. 21 is the outline for the synthesis of compound BN of the invention.

The synthesis of compound BN within the invention is outlined in FIG. 21, with the details given below. The structures of compounds synthesized in this example were confirmed using the following procedures: $^1$H NMR data were acquired on a Varian Mercury 300 spectrometer at 300 MHz, with chemical shifts referenced to internal TMS. Liquid chromatography electrospray ionization mass spectrometry (LC-ESI-MS) analysis was performed on instrumentation consisting of Shimadzu LC-10AD vp series HPLC pumps and dual wavelength UV detector, a Gilson 215 autosampler, a Sedex 75c evaporative light scattering (ELS) detector, and a PE/Sciex API 150EX mass spectrometer. The ELS detector was set to a temperature of 40° C., a gain setting of 7, and a $N_2$ pressure of 3.3 atm. The Turbo IonSpray source was employed on the API 150 with an ion spray voltage of 5 kV, a temperature of 300° C., and orifice and ring voltages of 5 V and 175 V respectively. Positive ions were scanned in Q1 from 160 to 650 m/z. 5.0 μL injections were performed for each sample, on a Phenomenex Gemini 5 μm C18 column. Mobile phases consisted of 0.05% formic acid in both HPLC grade water (A) and HPLC grade acetonitrile (B) using the following gradients with a flow rate of 2 mL/min: 0.00 min, 95% A, 5% B; 4.00 min, 0% A, 100% B; 5.80 min, 0% A, 100% B; 6.00 min, 95% A, 5% B; 7.00 min, 95% A, 5% B.

Preparation of 4-(5-bromo-2-chlorobenzoyl)phenethyl acetate (Intermediate BF)

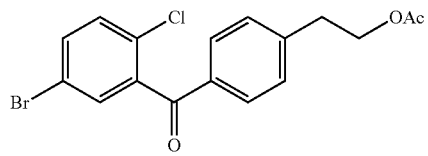

To a solution of commercially available 5-bromo-2-chlorobenzoic acid (5 g, 21.23 mmol) in 30 mL of anhydrous DCM was added a catalytic amount of DMF followed by oxalyl chloride (1.95 mL, 22.3 mmol) and stirred for 2 h at room temperature. A mixture of aluminum trichloride (3.68 g, 27.6 mmol) and phenethyl acetate (3.38 mL, 21.23 mmol) in 15 mL DCM was cooled in an ice-bath and the acid chloride was transferred to it using a canula. The mixture was stirred at room temperature for 4 h. The mixture was poured into 100 mL of ice-cold water and the organic layer was isolated. The aqueous solution was extracted with 25 mL DCM. The combined organic solution was washed with brine (25 mL) and dried ($Na_2SO_4$), filtered and evaporated. Purification on silica gel using an ISCO column with 5:1 hexane:EtOAc followed by 10:1 hexane:EtOAc gave intermediate BF (2.1 g, yield 26%). $^1$H NMR (300 MHz, $CDCl_3$): δ 8.12 (d, J=2.4 Hz, 1H), 7.71 (d, J=8.4 Hz, 1H), 7.59 (d, J=2.7 Hz, 1H), 7.56 (d, J=8.4 Hz, 1H), 7.36 (s, 1H), 7.33 (d, J=8.4 Hz, 1H), 7.30 (d, J=8.4 Hz, 1H), 4.31 (t, J=6.9, 6.6 Hz, 2H), 3.01 (t, J=6.9, 6.6 Hz, 2H), 2.04 (s, 3H).

Preparation of 4-(5-bromo-2-chlorobenzyl)phenethyl acetate (Intermediate BG)

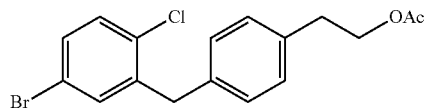

A mixture of 4-(5-bromo-2-chlorobenzoyl)phenethyl acetate (intermediate BF) (1 g, 2.62 mmol), borontrifluoride diethylether (0.65 mL, 10.4 mmol) and triethylsilane (0.84 mL, 10.4 mmol) was heated at 85° C. for 2 h in a sealed tube. The reaction vessel was cooled to room temperature and ice-water (50 mL) was added. The product was extracted with ethyl acetate (2×25 mL), washed with brine (25 mL), dried ($Na_2SO_4$), filtered and evaporated. Purification on silica gel using an ISCO column with 5% ethyl acetate in hexane gave intermediate BG (620 mg, yield 65%). $^1$H NMR (300 MHz, $CDCl_3$): δ 7.27-7.10 (m, 7H), 4.27 (t, J=6.9, 7.2 Hz, 2H), 4.03 (s, 2H), 2.92 (t, J=6.9, 7.2 Hz, 2H), 2.05 (s, 3H).

Preparation of 2-(4-(5-bromo-2-chlorobenzyl)phenyl)ethanol (Intermediate BH)

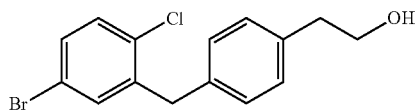

4-(5-bromo-2-chlorobenzyl)phenethyl acetate (intermediate BG) (400 mg, 1.09 mmol) and potassium carbonate (481 mg, 3.48 mmol) were stirred at room temperature in a mixture of 3 mL methyl alcohol and 0.5 mL water for 3 h. Solvents were evaporated and the residue taken up in 25 mL ether was washed with water (5 mL) and brine (20 mL), dried ($Na_2SO_4$), filtered and evaporated. Purification on silica gel using an ISCO column with 15:1 hexane:EtOAc gave intermediate BH (271 mg, yield 76%). $^1$H NMR (300 MHz, $CDCl_3$): δ 7.27-7.07 (m, 7H), 4.02 (s, 2H), 3.84 (m, 2H), 2.86 (m, 3H); LC-ESI-MS (m/z): 325 (M+H).

Preparation of 2-(4-(2-(allyloxy)ethyl)benzyl)-4-bromo-1-chlorobenzene (Intermediate BI)

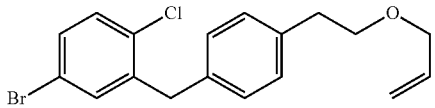

A mixture of 2-(4-(5-bromo-2-chlorobenzyl)phenyl)ethanol (intermediate BH) (245 mg, 0.75 mmol), allyl bromide (2.6 mL, 3.01 mmol), potassium hydroxide (84 mg, 1.5 mmol) and tetra-n-butylammonium iodide (13.9 mg, 0.037 mmol) was stirred at room temperature for 6 h. Water (1 mL) was added and extracted with chloroform (3×1 mL), washed with brine (1 mL) and dried ($Na_2SO_4$), filtered and evaporated. Preparative TLC using 10:1 hexane:EtOAc gave intermediate BI (246 mg, yield 89%). $^1$H NMR (300 MHz, $CDCl_3$): δ 7.26-7.08 (m, 7H), 5.90 (m, 1H), 5.22 (m, 2H), 4.02 (s, 2H), 3.99 (m, 2H), 3.64 (t, J=6.9, 7.2 Hz, 2H), 2.89 (t, J=6.9, 7.2 Hz, 2H).

Preparation of (2S,3R,4S,5R,6R)-2-(3-(4-(2-(allyloxy)ethyl)benzyl)-4-chlorophenyl)-3,4,5-tris(benzyloxy)-6-(benzyloxymethyl)-2-methoxytetrahydro-2H-pyran (Intermediate BJ)

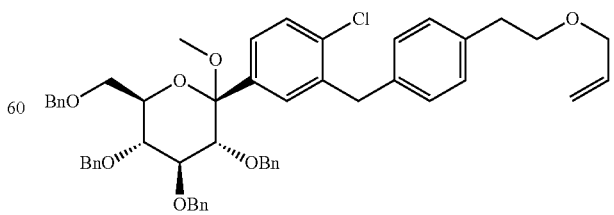

To a mixture of 2-(4-(2-(allyloxy)ethyl)benzyl)-4-bromo-1-chlorobenzene (intermediate BI) (123 mg, 0.34 mmol) and (3R,4S,5R,6R)-3,4,5-tris(benzyloxy)-6-(benzyloxymethyl)tetrahydro-2H-pyran-2-one (362 mg, 0.67 mmol) in anhydrous THF (1.5 mL) under argon and kept at −78° C. was added dropwise a 1.6 M solution of n-butyl lithium in hexane (0.63 mL) over 15 min. The mixture was stirred at −78° C. for 1.5 h. A solution of methanesulfonic acid (0.1 mL) in methanol (1 mL) was added to the reaction mixture and allowed to warm to room temperature over time. The mixture was stirred at room temperature for 21 h. A saturated solution of sodium bicarbonate was slowly added to the reaction mixture to bring the pH to 8. Water (2 mL) was added and the product was extracted into ethyl acetate (3×2 mL), the combined ethyl acetate solution was washed with brine (1.5 mL), dried (Na$_2$SO$_4$), filtered and evaporated. Preparative thin layer chromatography (TLC) using 12:1 hexane:EtOAc gave intermediate BJ (80 mg, yield 28%). LC-ESI-MS (m/z): 807 (M−OMe).

Preparation of (2S,3S,4R,5R,6R)-2-(3-(4-(2-(allyloxy)ethyl)benzyl)-4-chlorophenyl)-3,4,5-tris(benzyloxy)-6-(benzyloxymethyl)tetrahydro-2H-pyran (Intermediate BK)

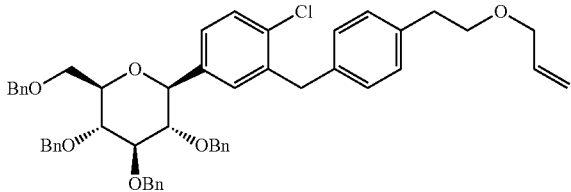

(2S,3R,4S,5R,6R)-2-(3-(4-(2-(allyloxy)ethyl)benzyl)-4-chlorophenyl)-3,4,5-tris(benzyloxy)-6-(benzyloxymethyl)-2-methoxytetrahydro-2H-pyran (intermediate BJ) (55 mg, 0.065 mmol) was taken up in 1 mL anhydrous DCM kept under argon, and triethylsilane (31.4 μL, 0.197 mmol) was added. The mixture was brought to −20° C. and borontrifluoride diethyletherate (20.1 μL, 0.164 mmol) was added. The mixture was allowed to warm and stirred at −5° C. to 0° C. for 3 h. Water (0.5 mL) was added to quench the reaction and the organic layer was separated. The aqueous layer was extracted with DCM (1 mL), and the combined organic solution was washed with brine (1 mL), dried (Na$_2$SO$_4$), filtered and evaporated. Preparative TLC using 10:1 hexane:EtOAc gave intermediate BK (39.5 mg, yield 60%). $^1$H NMR (300 MHz, CDCl$_3$): δ 7.30-7.03 (m, 27H), 5.90 (m, 1H), 5.22 (m, 2H), 4.88-4.70 (m, 3H), 4.65-4.38 (m, 5H), 4.16-4.08 (m, 3H), 4.05-3.88 (m, 4H), 3.82-3.72 (m, 5H), 3.60-3.52 (m, 3H); LC-ESI-MS (m/z): 808 (M+H).

Preparation of 2-(4-(2-chloro-5-((2S,3S,4R,5R,6R)-3,4,5-tris(benzyloxy)-6-(benzyloxymethyl)tetrahydro-2H-pyran-2-yl)benzyl)phenyl)ethanol (Intermediate BL)

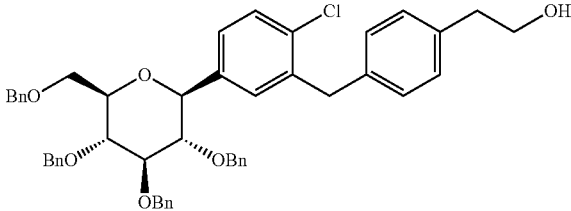

(2S,3S,4R,5R,6R)-2-(3-(4-(2-(allyloxy)ethyl)benzyl)-4-chlorophenyl)-3,4,5-tris(benzyloxy)-6-(benzyloxymethyl)tetrahydro-2H-pyran (intermediate BK) (50 mg, 0.061 mmol) was taken up in 90% aqueous acetic acid (1 mL), and sodium acetate (30.4 mg, 0.37 mmol) was added, followed by palladium(II)chloride (27.4 mg, 0.154 mmol). The mixture was heated at 70° C. for 5 h. Solvent was evaporated and the residue was taken up in 2 mL DCM and the mixture was filtered through a short Celite® pad. The pad was washed with a copious amount of DCM until all material had eluted. After evaporation of solvent, the residue was purified by TLC using 4:1 hexane:EtOAc to obtain intermediate BL (20 mg, yield 42%). LC-ESI-MS (m/z): 770 (M+H), 791 (M+H+Na).

Preparation of (2R,3R,4R,5S,6S)-3,4,5-tris(benzyloxy)-2-(benzyloxymethyl)-6-(4-chloro-3-(4-(2-(difluoromethoxy)ethyl)benzyl)phenyl)tetrahydro-2H-pyran (Intermediate BM)

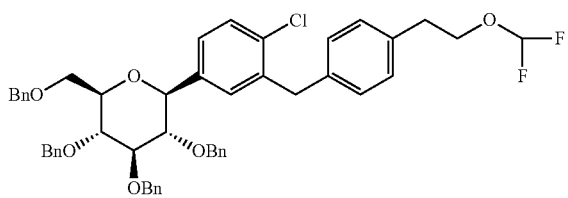

To a mixture of 2-(4-(2-chloro-5-((2S,3S,4R,5R,6R)-3,4,5-tris(benzyloxy)-6-(benzyloxymethyl)tetrahydro-2H-pyran-2-yl)benzyl)phenyl)ethanol (intermediate BL) (20 mg, 0.020 mmol) and sodium sulfate (0.40 mg, 0.003 mmol) in anhydrous acetonitrile (0.5 mL) kept at 45° C. was added 2,2-difluoro-2-(fluorosulfonyl)acetic acid (4.63 mg, 2.7 μL, 0.026 mmol). The mixture was stirred at this temp for 1 h and poured into 3 mL water. Product was extracted into ether (3×1 mL), dried (Na$_2$SO$_4$) and evaporated. The residue was purified by TLC using 6:1 hexane:EtOAc to obtain intermediate BM (7 mg, yield 33%).

Preparation of (2S,3R,4R,5S,6R)-2-(4-chloro-3-(4-(2-(difluoromethoxy)ethyl)benzyl)phenyl)-6-(hydroxymethyl)tetrahydro-2H-pyran-3,4,5-triol (Compound BN)

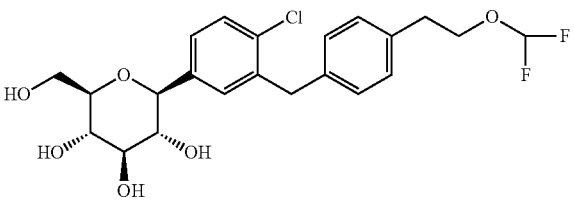

(2R,3R,4R,5S,6S)-3,4,5-tris(benzyloxy)-2-(benzyloxymethyl)-6-(4-chloro-3-(4-(2-(difluoromethoxy)ethyl)benzyl)phenyl)tetrahydro-2H-pyran (intermediate BM) was taken up in a mixture of 4:1 methanol:tetrahydrofuran (0.5 mL) and 9.6 μL of 1,2-dichlorobenzene was added followed by palladium on charcoal (10%, 5 mg). The mixture was stirred at room temperature under a hydrogen balloon for 30 min. The mixture was passed through a short Celite® pad to remove the catalyst, and the pad was washed with methanol (1 mL). Solvent was evaporated and the product was purified by TLC using 8:1 dichloromethane:methanol to obtain compound BN (2.5 mg, yield 64%). $^1$H NMR (300 MHz, CDCl$_3$): δ 7-33-7.11 (m, 7H), 6.30 (t, J$_{C-F}$=75.6 Hz, 1H), 4.13 (d, J=9 Hz, 1H), 4.04 (m, 4 H), 3.86-3.80 (m, 3H), 3.64 (t, J=4.5, 6.6 Hz, 2H), 3.47-3.41 (m, 2H), 2.90 (t, J=6.9, 7.2 Hz, 2H); LC-ESI-MS (m/z): 457 (M−H).

Example 19

The synthesis of compound BQ within the invention is given below.

Preparation of 2-cyclopropoxyethanol (Intermediate BO)

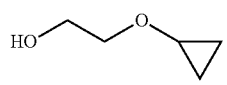

To a suspension of Mg powder (0.87 g, 36.1 mmol) and iodine (catalytic) in THF (4 mL) was added slowly BrCH$_2$CH$_2$Br (4.6 g, 24.5 mmol) in THF (8 mL). The exothermic reaction was cooled in an ice-bath. After complete addition of BrCH$_2$CH$_2$Br, a solution of 2-(2-bromoethyl)-1,3-dioxolane (1 g, 5.6 mmol) was added dropwise. The reaction mixture was then kept at reflux for 24 h, quenched by addition of aqueous NH$_4$Cl, and extracted with DCM. The combined organic layers were washed with brine, dried over Na$_2$SO$_4$, and concentrated to give crude intermediate BO (400 mg) as yellow oil.

Preparation of 2-cyclopropoxyethyl 4-methylbenzenesulfonate (Intermediate BP)

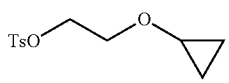

To a solution of 2-cyclopropoxyethanol (400 mg, 3.92 mmol) in DCM (10 mL) were added TsCl (821 mg, 4.31 mmol) and Et$_3$N (0.6 mL, 4.31 mmol). The reaction was stirred at room temperature overnight. Then, 1N HCl was added, and the reaction was extracted with DCM. The combined organic layers were washed with brine, dried over Na$_2$SO$_4$, and concentrated to give a yellow oil. The oil was purified by preparative TLC to obtain intermediate BP (50 mg) as a yellow oil.

Preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol (Compound BQ)

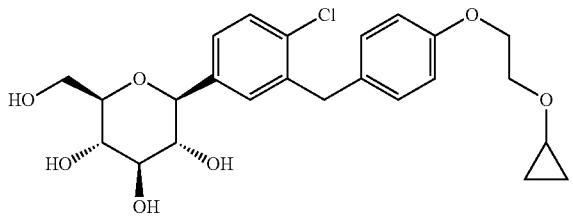

To a solution of (2S,3R,4R,5S,6R)-2-(4-chloro-3-(4-hydroxybenzyl)phenyl)-6-(hydroxymethyl)tetrahydro-2H-pyran-3,4,5-triol (intermediate D1) (30 mg, 0.08 mmol) in anhydrous DMF (1 mL) were added 2-cyclopropoxyethyl 4-methylbenzenesulfonate (intermediate BP) (20 mg, 0.08 mmol) and Cs$_2$CO$_3$ (52 mg, 0.16 mmol). The mixture was stirred at room temperature for 12 h. Then the reaction mixture was poured into water, extracted with EA, washed with brine, dried with anhydrous Na$_2$SO$_4$ and concentrated to an oil. The oil was purified by preparative HPLC to obtain compound BQ (11 mg) as a colorless oil. $^1$H NMR (CD$_3$OD): δ 7.30 (m, 3H), 7.11 (d, J=8.8 Hz, 2H), 6.82 (d, J=8.8 Hz, 2H), 4.13 (m, 5H), 3.85 (m, 3H), 3.81 (m, 1H), 3.40 (m, 4H), 3.30 (m, 1H), 0.52 (m, 4H); MS ESI (m/z) 465 (M+H)$^+$, calc. 464.

Example 20

The synthesis of compound BT within the invention is given below.

Preparation of 2-(2,2,2-trifluoroethoxy)ethanol (Intermediate BR)

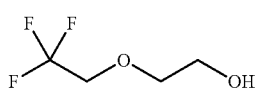

2,2,2-trifluoroethanol (15 g), 1,3-dioxolan-2-one (19.8 g) and Et$_3$N (15 g) were mixed together, and then the mixture was heated to 100° C. and stirred for 24 h. Then the reaction mixture was distilled to obtain intermediate BR (12.7 g).

Preparation of 2-(2,2,2-trifluoroethoxy)ethyl 4-methylbenzenesulfonate (Intermediate BS)

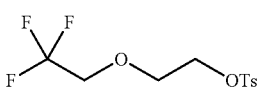

2-(2,2,2-trifluoroethoxy)ethanol (intermediate BR) (12.7 g) was dissolved in anhydrous pyridine, then TsCl (1.3 eq) was added, and the mixture was stirred at room temperature for 16 h, after which TLC showed the reaction was complete. Then the mixture was poured into water, extracted with EA, washed with water and brine, and dried with anhydrous Na$_2$SO$_4$. The solvent was removed and the residue purified by column chromatography to obtain intermediate BS (0.3 g).

Preparation of (2S,3R,4R,5S,6R)-2-(4-chloro-3-(4-(2-(2,2,2-trifluoroethoxy)ethoxy)benzyl)phenyl)-6-(hydroxymethyl)tetrahydro-2H-pyran-3,4,5-triol (Compound BT)

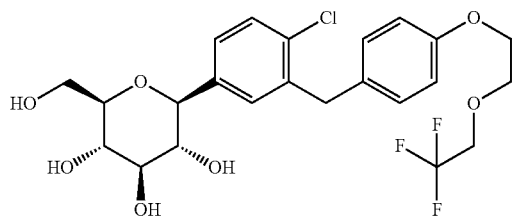

To (2S,3R,4R,5S,6R)-2-(4-chloro-3-(4-hydroxybenzyl)phenyl)-6-(hydroxymethyl)tetrahydro-2H-pyran-3,4,5-triol (intermediate D1) (200 mg) in anhydrous DMF were added 2-(2,2,2-trifluoroethoxy)ethyl 4-methylbenzenesulfonate (intermediate BS) (1.5 eq) and Cs$_2$CO$_3$ (2 eq). The mixture was stirred at room temperature for 12 h, after which LC-MS showed the reaction was complete. The reaction mixture was poured into water, extracted with EA, washed with water and brine, and then dried with anhydrous Na$_2$SO$_4$ and concentrated to an oil. The oil was purified by preparative-HPLC to obtain compound BT (117 mg). $^1$H NMR (CD$_3$OD, 400 MHz): δ 7.32 (m, 3H), 7.11 (d, J=8.8 Hz, 2H), 6.86 (d, J=8.8 Hz, 2H), 4.62 (s, 2H), 4.08~4.12 (m, 3H), 4.02~4.05 (m, 3H), 4.00~3.94 (m, 2H), 3.90~3.87 (m, 1H), 3.72~3.68 (m, 1H), 3.46~3.39 (m, 3H), 3.30~3.27 (m, 1H); MS ESI (m/z) 507 (M+H)$^+$, calc. 506.

Example 21

The synthesis of compound BW within the invention is given below.

Preparation of 2-(cyclohex-2-enyloxy)ethanol (Intermediate BU)

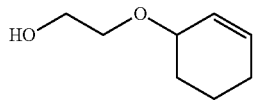

To a solution of 3-bromocyclohex-1-ene (0.5 g) in anhydrous DMF (5 mL) were added ethylene glycol (3 eq) and $Cs_2CO_3$ (5 g). The mixture was heated to 80° C. and stirred overnight, after which TLC (PE:EA=20:1) showed the reaction was complete. Then the mixture was poured into water and extracted with EA, washed with water and brine, and concentrated to an oil, which was purified by column chromatography to obtain intermediate BU (0.3 g).

Preparation of 2-(cyclohex-2-enyloxy)ethyl 4-methylbenzenesulfonate (Intermediate BV)

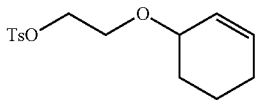

To 2-(cyclohex-2-enyloxy)ethanol (intermediate BU) (0.3 g) in anhydrous pyridine was added TsCl (1.3 eq). The mixture was stirred at room temperature for 16 h, after which TLC showed the reaction was complete. The mixture was poured into water, extracted with EA, washed with water and brine, and dried with anhydrous $Na_2SO_4$. Solvent was removed and the residue purified by column chromatography to obtain intermediate BV (0.3 g).

Preparation of (2S,3R,4R,5S,6R)-2-(4-chloro-3-(4-(2-(cyclohex-2-enyloxy)ethoxy)benzyl)phenyl)-6-(hydroxymethyl)tetrahydro-2H-pyran-3,4,5-triol (Compound BW)

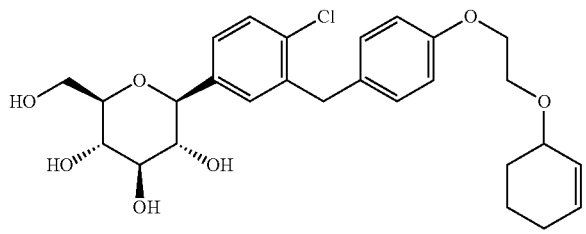

To (2S,3R,4R,5S,6R)-2-(4-chloro-3-(4-hydroxybenzyl)phenyl)-6-(hydroxymethyl)tetrahydro-2H-pyran-3,4,5-triol (intermediate D1) (30 mg) in anhydrous DMF were added 2-(cyclohex-2-enyloxy)ethyl 4-methylbenzenesulfonate (intermediate BV) (1.5 eq) and $Cs_2CO_3$ (2 eq). The mixture was stirred at room temperature for 16 h, after which LC-MS showed the reaction was complete. The reaction mixture was poured into water, extracted with EA, washed with water and brine, and then dried with anhydrous $Na_2SO_4$ and concentrated to an oil. The crude oil was purified by preparative-HPLC to obtain compound BW (17.1 mg). $^1H$ NMR ($CD_3OD$, 400 MHz): δ 7.32 (m, 3H), 7.11 (d, J=8.8 Hz, 2H), 6.86 (d, J=8.8 Hz, 2H), 5.87~5.76 (s, 2H), 4.59 (s, 1H), 4.11~3.89 (m, 6H), 3.89~3.76 (m, 3H), 3.72~3.68 (m, 1H), 3.49~3.40 (m, 3H), 2.03~1.98 (m,2H), 1.89~1.84 (m, 1H), 1.80~1.62 (m, 2H), 1.79~1.51 (m, 1H); MS ESI (m/z) 506 $(M+H)^+$, calc. 505.

Example 22

The synthesis of compound BZ within the invention is given below.

Preparation of (E)-3-cyclopropylprop-2-en-1-ol (Intermediate BX)

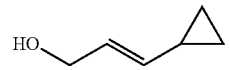

To a solution of 3-cyclopropylprop-2-yn-1-ol (intermediate AT) (1 g, 0.0096 mol, purity 92%) in 10 ml of dry ether was added carefully a suspension of $LiAlH_4$ (0.79 g, 0.021 mol) in dry ether (10 ml) at 0° C. The resulting solution was stirred at room temperature for 3.5 h, and then quenched with 20 ml of ice-water. The aqueous layer was extracted 3×10 ml of ether, and the combined organic layers were washed with saturated $NH_4Cl$ and brine, dried over anhydrous $Na_2SO_4$, and concentrated to obtain intermediate BX (0.75 g, purity 62%, yield 79.8%) as a crude yellow oil, which was used in the next step without further purification.

Preparation of (E)-(3-bromoprop-1-enyl)cyclopropane (Intermediate BY)

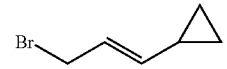

To a solution of (E)-3-cyclopropylprop-2-en-1-ol (intermediate BX) (0.375 g, 2.37 mmol, purity 62%) in dry diethyl ether (4 ml) was added phosphorus tribromide (0.36 ml, 3.83 mmol) at 0° C. After being stirred at the same temperature for 2 h, the mixture was warmed to room temperature and stirred for another 2 h. The reaction mixture was poured into ice water, and the aqueous layer was extracted 3× with 10 ml of ether. The combined organic layers were washed with water and brine, dried over anhydrous $Na_2SO_4$, and concentrated to obtain intermediate BY (0.15 g) as a crude yellow oil, which was used in the next step without further purification.

Preparation of (2S,3R,4R,5S,6R)-2-(4-chloro-3-(4-((E)-3-cyclopropylallyloxy)benzyl)phenyl)-6-(hydroxymethyl)tetrahydro-2H-pyran-3,4,5-triol (Compound BZ)

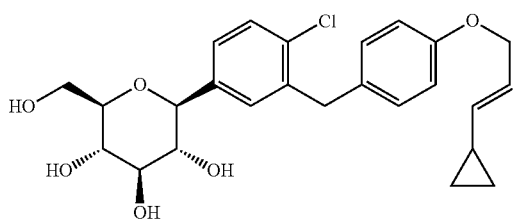

To a stirred solution of (2S,3R,4R,5S,6R)-2-(4-chloro-3-(4-hydroxybenzyl)phenyl)-6-(hydroxymethyl)tetrahydro-2H-pyran-3,4,5-triol (intermediate D1) (37 mg, 0.097 mmol) in 1.5 ml of DMF was added $Cs_2CO_3$ (48 mg, 0.146 mmol) and (E)-(3-bromoprop-1-enyl)cyclopropane (intermediate BY) (50 mg) at room temperature. After stirring for 3 h, the reaction was quenched with 2 ml of ice water. The mixture was extracted 3× with ethyl acetate (5 ml), and the combined organic layers were washed 2× with water (5 ml) and brine, dried over $Na_2SO_4$, concentrated, and purified by preparative LC-MS to obtain compound BZ (8.6 mg). ¹H NMR (CD₃OD, 400 MHz): δ 7.37~7.33 (2H, m), 7.30~7.27 (1H, dd, J=8.2, 2 Hz), 7.11~7.09 (2H, d,J=8.8 Hz), 6.82~6.79 (2H, d,J=8.8 Hz), 5.77~5.70 (1H, dt, J=15.2, 6 Hz), 5.39~5.33 (1H, dd, J=15.2, 8.8 Hz), 4.43~4.41 (2H, dd, J=6.4, 1.0 Hz), 4.10 (1H, d, J=9.6 Hz), 4.08~3.98 (2H, dd,J=23.6, 15.2 Hz), 3.90~3.87 (1H, m), 3.72~3.67 (1H, m), 3.49~3.39 (3H, m), 3.31~3.27 (1H, m), 1.47~1.45 (1H, m), 0.76~0.71 (2H, m), 0.41~0.37 (2H, m); MS ESI (m/z) 461 (M+H)⁺, calc. 460.

Example 23

Figure 22:
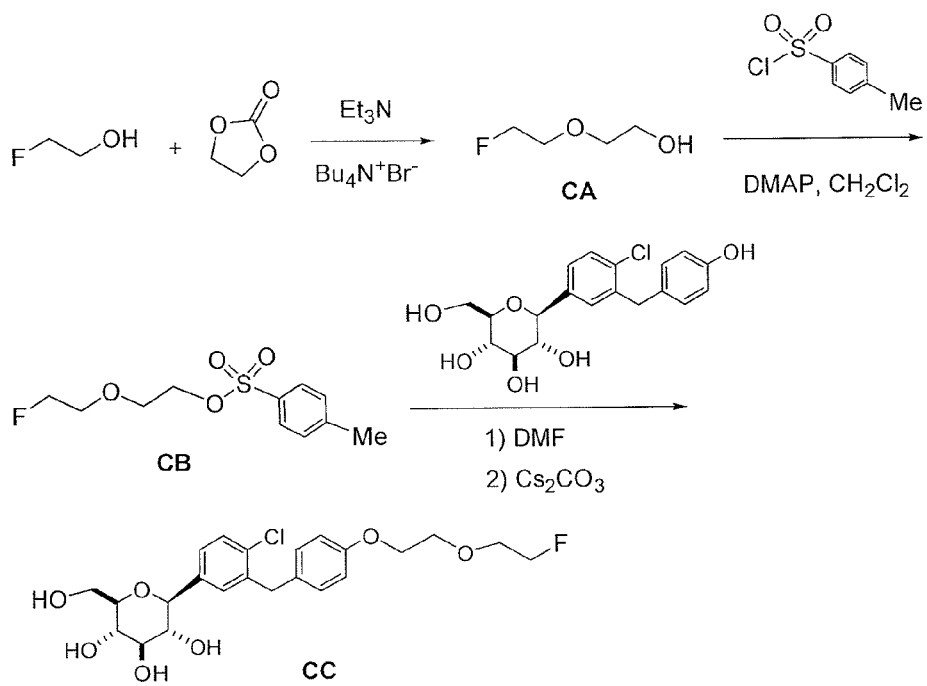
FIG. 22 is the outline for the synthesis of compound CC of the invention.

The synthesis of compound CC within the invention is outlined in FIG. 22, with the details given below. The structures of compounds synthesized in this example were confirmed using the analytical procedures as described in Example 18.

Preparation of 2-(2-fluoroethoxy)ethanol (Intermediate CA)

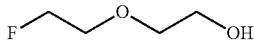

2-Fluoroethanol (5.0 g, 78 mmol), triethylamine (8.4 g, 83 mmol), and tetrabutylammonium bromide (0.50 g, 1.5 mmol) were combined and stirred at ambient temperature for 5 min. Ethylene carbonate (7.6 g, 86 mmol) was added and the resulting mixture was heated at 100° C. for 18 h. Preliminary distillation of the reaction mixture at atmospheric pressure was performed to remove low boiling point liquids. Subsequent distillation of the mixture under high vacuum was performed to obtain the title compound (1.2 g, 14%) as a clear oil. The temperature of the distillation head was 110-115° C. when the product was being collected under high vacuum. ¹H NMR (CDCl₃, 300 MHz): δ 4.52 (dt, 2H, J1=64.0 Hz, J2=5.2 Hz), 3.75-3.55 (m, 6H), 3.16 (br s, 1H).

Preparation of 2-(2-fluoroethoxy)ethyl 4-methylbenzenesulfonate (Intermediate CB)

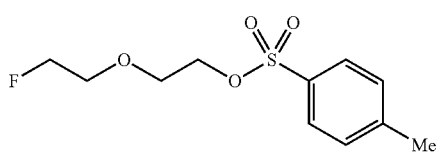

2-(2-Fluoroethoxy)ethanol (0.11 g, 1.0 mmol), p-toluenesulfonyl chloride (0.19 g, 1.0 mmol), and DMAP (0.12 g, 1.0 mmol) were dissolved in dichloromethane (2 ml) at 0° C. The resulting mixture was stirred for 2 h at 0° C., after which it was subjected directly to silica gel chromatography using dichloromethane as the eluent to give the title compound (70 mg, 27%) as a clear oil. It was observed that the size of the column affects reaction yield, with a smaller column giving a better yield. ¹H NMR (CDCl₃, 300 MHz): δ 7.79 (d, 2H, J=11.6 Hz), 7.33 (d, 2H, J=11.6 Hz), 4.48 (dt, 2H, J1=64.0 Hz, J2=5.6 Hz), 4.17 (t, 2H, J=6.4 Hz), 3.71 (t, 2H, J=6.4 Hz), 3.66 (dt, 2H, J1=5.6 Hz, J2=39.2 Hz), 2.44 (br S, 3H).

Preparation of (2S,3R,4R,5S,6R)-2-(4-chloro-3-(4-(2-(2-fluoroethoxy)ethoxy)benzyl)phenyl)-6-(hydroxymethyl)tetrahydro-2H-pyran-3,4,5-triol (Compound CC)

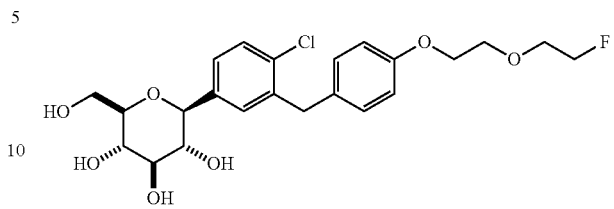

2-(2-fluoroethoxy)ethyl 4-methylbenzenesulfonate (52 mg, 0.19 mmol) dissolved in anhydrous DMF (3 mL) was added to a flask containing (2S,3R,4R,5S,6R)-2-(4-chloro-3-(4-hydroxybenzyl)phenyl)-6-(hydroxymethyl)tetrahydro-2H-pyran-3,4,5-triol (intermediate D1) (57 mg, 0.15 mmol) in DMF (3 mL) at room temperature. Cesium carbonate (0.12 g, 0.36 mmol) was added to the flask, and the resulting mixture was stirred at room temperature for 48 hr. The reaction mixture was diluted with diethyl ether (50 mL) and the organic layer was washed with aqueous solutions of ammonium chloride (50 mL), sodium bicarbonate (50 mL), and NaCl (50 mL), followed by drying over sodium sulfate. The organic layer was concentrated in vacuo, followed by preparative TLC using 15% methanol in dichloromethane as the mobile phase to yield the title compound (4.5 mg, 5.0%). ¹H NMR (CDCl₃, 300 MHz): δ 7.30 (d, 1H, J=11.6 Hz), 7.17-7.12 (br m, 2H), 7.04 (d, 2H, J=11.6 Hz), 6.78 (d, 2H, J=11.6 Hz), 4.52 (dt, 2H, J1=5.6 Hz, J2=63.6 Hz), 4.33 (br s, 1H), 4.13 (br s, 1H), 4.04-3.96 (m, 4H), 3.81-3.67 (m, 5H), 3.63-3.49 (m, 2H), 3.38-3.21 (m, 3H), 2.78 (br s, 1H), 1.77 (br s, 2H); LC/MS: theoretical mass=470.15; observed M+1=471.6, M+Na=493.4).

Example 24

Figure 23:
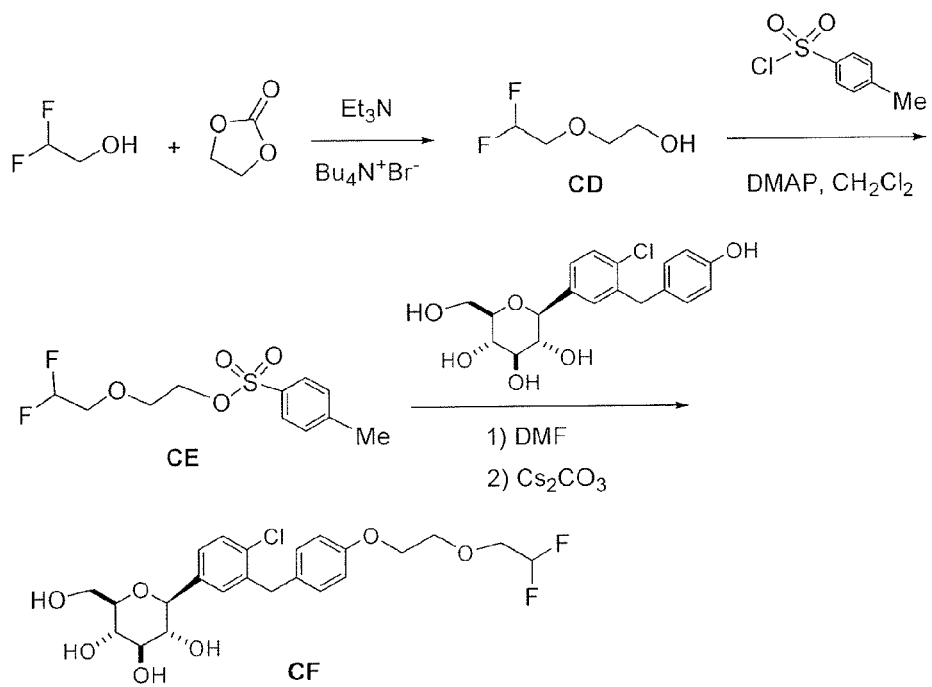
FIG. 23 is the outline for the synthesis of compound CF of the invention.

The synthesis of compound CF within the invention is outlined in FIG. 23, with the details given below. The structures of compounds synthesized in this example were confirmed using the analytical procedures as described in Example 18.

Preparation of (Intermediate CD)

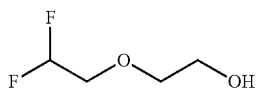

2,2-Difluoroethanol (5.1 g, 63 mmol), triethylamine (6.7 g, 66 mmol), and tetrabutylammonium bromide (0.40 g, 1.3 mmol) were mixed for 5 min at ambient temperature. Ethylene carbonate (6.1 g, 69mmol) was added and the combined mixture was refluxed at 100° C. for 18 h. Distillation at atmospheric pressure was first conducted to strip off low boiling point liquids. Then distillation was performed under high vacuum to yield the title compound as a clear oil (4.7 g, 59%). The temperature of the distillation head was 109-113° C. when the title compound was being collected under high vacuum. ¹H NMR (CDCl₃, 300 MHz): δ 5.86 (ttd, 1H, J1=73.6 Hz, J2=5.6 Hz, J3=0.8 Hz), 3.74-3.61 (m, 6H), 2.65 (br s, 1H).

Preparation of 2-(2,2-difluoroethoxy)ethyl 4-methylbenzenesulfonate (Intermediate CE)

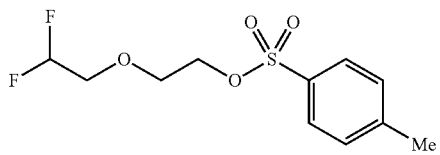

2-(2,2-difluoroethoxy)ethanol (0.13 g, 1.0 mmol), p-toluenesulfonyl chloride (0.19 g, 1.0 mmol), and DMAP (0.12 g, 1.0 mmol) were dissolved in dichloromethane (2 ml) at 0° C. and stirred for 2 h at this temperature. The reaction mixture was loaded onto a small column, which was eluted with dichloromethane to yield the title compound as a clear oil (53 mg, 19%). It was observed that the size of the column affects reaction yield, with a smaller column giving a better yield. $^1$H NMR (CDCl$_3$, 300 MHz): δ 7.78 (d, 2H, J=11.2 Hz), 7.34 (d, 2H, J=11.2 Hz), 5.76 (tt, 1H, J1=5.6 Hz, J2=73.6 Hz), 4.17 (t, 2H, J=6.0 Hz), 3.75 (t, 2H, J=6.0 Hz), 3.64 (td, 2H, J1=6.0 Hz, J2=20 Hz), 2.45 (br s, 3H).

Preparation of (2S,3R,4R,5S,6R)-2-(4-chloro-3-(4-(2-(2,2-difluoroethoxy)ethoxy)benzyl)phenyl)-6-(hydroxymethyl)tetrahydro-2H-pyran-3,4,5-triol (Compound CF)

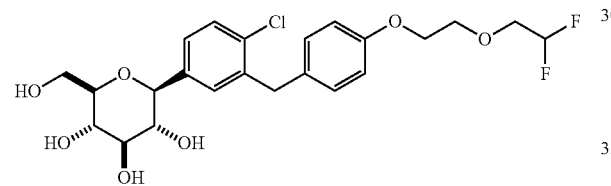

2-(2,2-difluoroethoxy)ethyl 4-methylbenzenesulfonate (53 mg, 0.19 mmol) dissolved in anhydrous DMF (3 mL) was added to a reaction flask containing (2S,3R,4R,5S,6R)-2-(4-chloro-3-(4-hydroxybenzyl)phenyl)-6-(hydroxymethyl)tetrahydro-2H-pyran-3,4,5-triol (intermediate D1) (57 mg, 0.15 mmol) in DMF (3 mL) at room temperature. Cesium carbonate (98 mg, 0.30 mmol) was added to the flask, and the resulting mixture was stirred for 48 hr at room temperature. The reaction was diluted with diethyl ether (50 mL) and the organic layer was washed with an aqueous solution of ammonium chloride (50 mL), sodium bicarbonate (50 mL), and NaCl (50 ml), after which it was dried over sodium sulfate, filtered and concentrated en vacuo. The residue was purified by preparative TLC using 15% methanol in dichloromethane as the mobile phase to yield the title compound (4.6 mg, 5.0%). $^1$H NMR (CDCl$_3$, 300 MHz); δ 7.33 (d, 1H, J=11.2 Hz), 7.15 (d, 1H, J=11.2 Hz), 7.14 (s, 1H), 7.06 (d, 2H, J=11.6 Hz), 6.79 (d, 2H, J=11.6 Hz), 5.86 (tt, 1H, J1=5.2 Hz, J2=66.4 Hz), 4.07-3.98 (m, 3H), 3.87-3.84 (m, 3 H), 3.84-3.71 (m, 2H), 3.74 (td, 2H, J1=5.6 Hz, J2=18.4 Hz), 3.66-3.54 (m, 3 H), 3.30-3.36 (m, 2H), 2.78 (br s, 1H), 2.42 (br s, 1H), 1.65 (s, 2H); LC/MS: theoretical mass=488.14; observed M+1=489.2, M+Na=511.4).

Example 25

Figure 24:
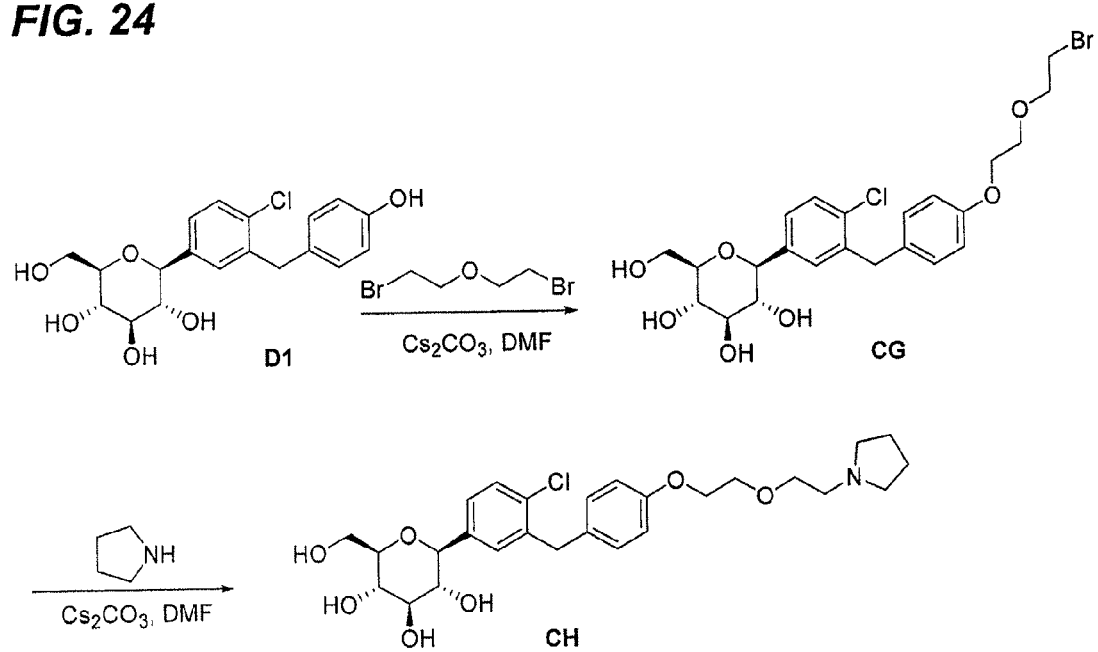
FIG. 24 is the outline for the synthesis of compound CH of the invention.

The synthesis of compound CH within the invention is outlined in FIG. 24, with the details given below.

Preparation of (2S,3R,4R,5S,6R)-2-(3-(4-(2-(2-bromoethoxy)ethoxy)benzyl)-4-chlorophenyl)-6-(hydroxymethyl)tetrahydro-2H-pyran-3,4,5-triol (Intermediate CG)

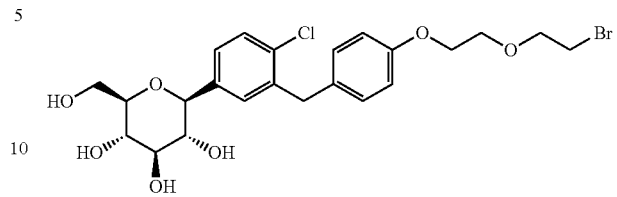

To a stirred suspension of (2S,3R,4R,5S,6R)-2-(4-chloro-3-(4-hydroxybenzyl)phenyl)-6-(hydroxymethyl)tetrahydro-2H-pyran-3,4,5-triol (intermediate D1) (100 mg, 0.26 mmol) in N,N-dimethylformamide (3 mL) and cesium carbonate (162 mg, 0.52 mmol) was added 1-bromo-2-(2-bromoethoxy)ethane (182 mg, 0.79 mmol). The mixture was stirred overnight at room temperature. The solution was diluted with water and the aqueous layer was extracted with ethyl acetate. The combined organic layers were concentrated under reduced pressure. The residue was purified by preparative TLC to give 30 mg of yellow oil (21% yield), which was used in the next step without purification.

Preparation of (2S,3R,4R,5S,6R)-2-(4-chloro-3-(4-(2-(2-(pyrrolidin-1-yl)ethoxy)ethoxy)benzyl)phenyl)-6-(hydroxymethyl)tetrahydro-2H-pyran-3,4,5-triol (Compound CH)

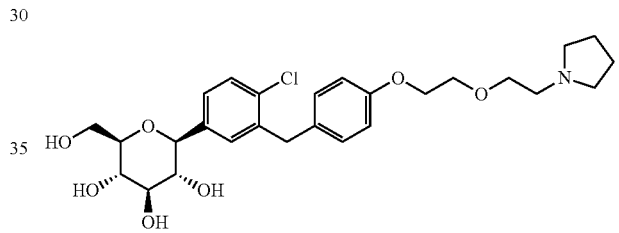

To a stirred suspension of (2R,3R,4R,5S,6R)-2-(3-(4-(2-(2-bromoethoxy)ethoxy)benzyl)-4-chlorophenyl)-6-(hydroxymethyl)tetrahydro-2H-pyran-3,4,5-triol (20 mg, 0.04 mmol) in N,N-dimethylformamide (5 mL) and cesium carbonate (25 mg, 0.08 mmol) was added pyrrolidine (26 mg, 0.38 mmol). The mixture was stirred for 5 h at 50° C. The solution was diluted with water and the aqueous layer was extracted with ethyl acetate. The combined organic layers were concentrated under reduced pressure. The residue was purified by preparative HPLC to give 15 mg of white solid (76% yield; HPLC purity: 99%). HPLC retention time: 1.85 min; Waters 2695 Separations Module equipped with a Waters 2996 Photodiode Array Detector and a Waters Micromass ZQ Detector; Waters XTerra C18 3.5 μm, 20 mm×2.1 mm column, 1.0 mL/min, detection at 190~400 nm; 1.7 min gradient 10-50% A, followed by 1.8 min gradient 50-95% A, hold 1 min at 95% A; solvent A: 0.045% formic acid in acetonitrile; solvent B: 0.1% formic acid in Milli-Q water. $^1$H NMR (CD$_3$OD, 400 MHz): δ 7.28-7.36 (m, 3H), 7.12-7.14 (d, J=8.8 Hz, 2H), 6.84-6.86 (d, J=8.8 Hz, 2H), 4.15-4.17 (m, 2H), 4.00-4.14 (m, 2H), 3.68-3.72 (m, 1H), 3.23-3.48 (m, 6H), 2.01-2.03 (m, 5H), 1.34-1.30 (m, 2H); MS ES$^-$ (m/z): 566 (M+45)$^-$.

Example 26

Figure 25:
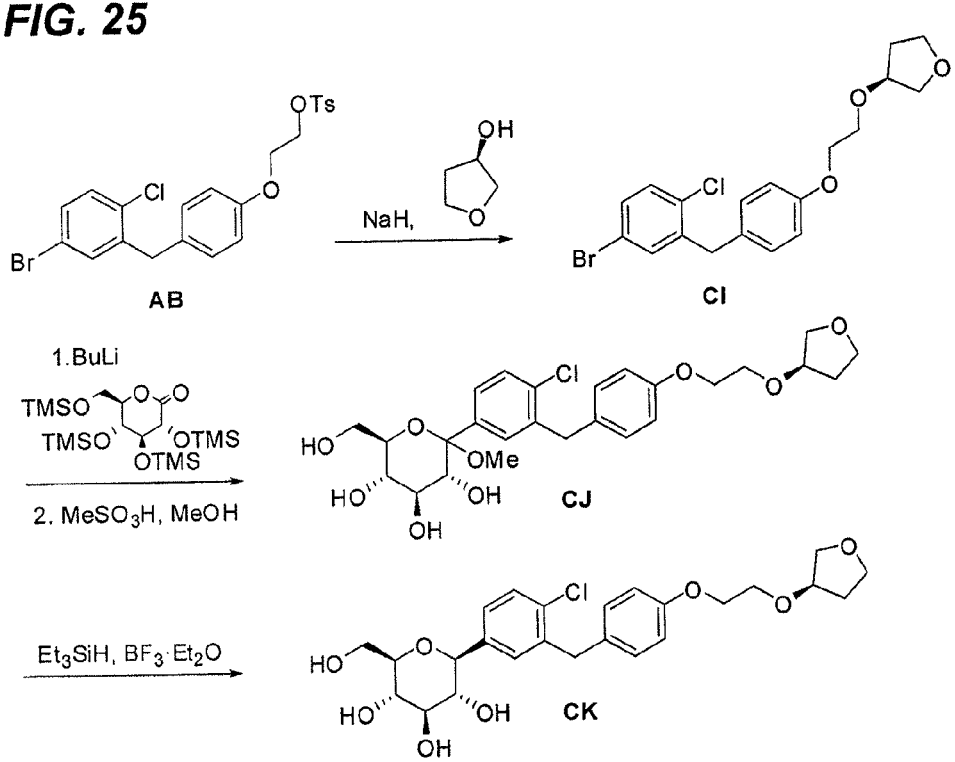
FIG. 25 is the outline for the synthesis of compound CK of the invention.

The synthesis of compound CK within the invention is outlined in FIG. 25, with the details given below.

Preparation of (S)-3-(2-(4-(5-bromo-2-chlorobenzyl)phenoxy)ethoxy)tetrahydrofuran (Intermediate CI)

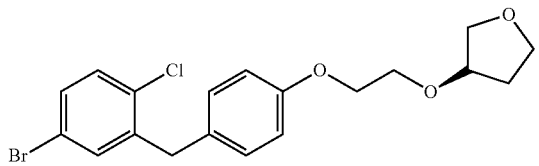

To a stirred solution of (R)-tetrahydrofuran-3-ol (320 mg, 3.63 mmol) in dry tetrahydrofuran (10 mL) was added sodium hydride (145 mg, 3.63 mmol, 60%) slowly under 0° C. The reaction was stirred at this temperature for 30 min and then 2-(4-(5-bromo-2-chlorobenzyl)phenoxy)ethyl 4-methylbenzenesulfonate (intermediate AB) (300 mg, 0.61 mmol) was added. The reaction was warmed to room temperature and then heated to reflux overnight. The reaction was quenched with saturated ammonium chloride and extracted with ethyl acetate. The organic layer was washed with brine, dried over sodium sulfate and concentrated to a yellow oil. The crude oil was purified by flash chromatography to get 200 mg of colorless oil (80% yield).

Preparation of (3R,4S,5S,6R)-2-(4-chloro-3-(4-(2-((S)-tetrahydrofuran-3-yloxy)ethoxy)benzyl)phenyl)-6-(hydroxymethyl)-2-methoxytetrahydro-2H-pyran-3,4,5-triol (Intermediate CJ)

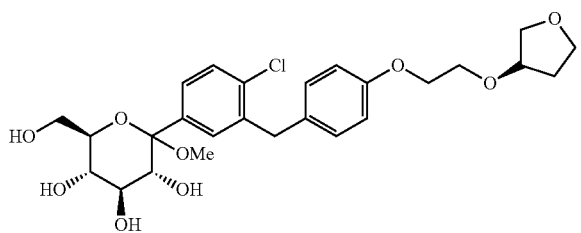

To a −65° C. solution of (S)-3-(2-(4-(5-bromo-2-chlorobenzyl)phenoxy)ethoxy)tetrahydrofuran (200 mg, 0.49 mmol) in anhydrous toluene/tetrahydrofuran (6 mL, v/v=2:1) was added dropwise n-butyllithum (2.5 M in hexane, 0.3 mL), and the pale yellow mixture was stirred for 30 min at −65° C. The mixture was transferred to a −65° C. solution of (3R,4S,5R,6R)-3,4,5-tris(trimethylsilyloxy)-6-((trimethylsilyloxy)methyl)tetrahydro-2H-pyran-2-one (280 mg, 0.73 mmol) in toluene (4 mL). The mixture was stirred at −65° C. for 2 h until starting material was consumed. The reaction was quenched with methanesulfonic acid (0.04 mL, 1.7 mmol) in methanol (6 mL), and the mixture was allowed to warm to 20° C. and stirred overnight. The reaction was quenched with saturated sodium bicarbonate. The organic phase was separated, and the aqueous phase was extracted with ethyl acetate. The organic phases were combined, washed with saturated sodium bicarbonate, then with water and then with brine prior to drying over anhydrous sodium sulfate. Removal of volatiles afforded 200 mg of crude solid product, which was used in the next step without further purification.

Preparation of (2S,3R,4R,5S,6R)-2-(4-chloro-3-(4-(2-((S)-tetrahydrofuran-3-yloxy)ethoxy)benzyl)phenyl)-6-(hydroxymethyl)tetrahydro-2H-pyran-3,4,5-triol (Compound CK)

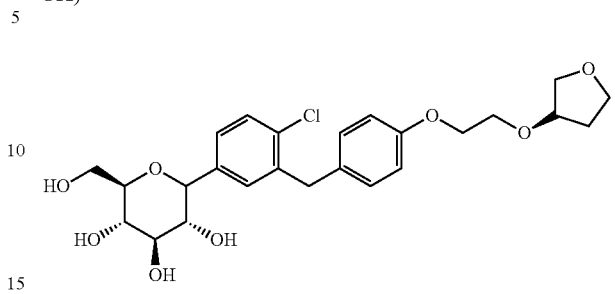

To a −15° C. solution of crude product from the previous step (200 mg, ~0.38 mmol) in 1:1 anhydrous acetonitrile/dichloromethane (4 mL) was added triethylsilane (0.12 mL, 0.76 mmol). Boron trifluoride diethyl etherate (0.08 mL, 0.57 mmol) was added dropwise, and then the mixture was stirred for 4 h at −10° C. The reaction was quenched with saturated aqueous sodium bicarbonate. The volatiles were removed under reduced pressure, and the residue was extracted with ethyl acetate, washed with water and then with brine. The residue was dried over anhydrous sodium sulfate, filtered and concentrated to a solid, which was purified by preparative HPLC-MS to give 12 mg pure product (HPLC purity: 99%). HPLC retention time: 2.2 min; Waters 2695 Separations Module equipped with a Waters 2996 Photodiode Array Detector and a Waters Micromass ZQ Detector; Waters XTerra C18 3.5 μm, 20 mm×2.1 mm column, 1.0 mL/min, detection at 190~400 nm; 1.7 min gradient 10-50% A, followed by 1.8 min gradient 50-95% A, hold 1 min at 95% A; solvent A: 0.045% formic acid in acetonitrile; solvent B: 0.1% formic acid in Milli-Q water. $^1$H NMR (CD$_3$OD, 400 MHz): δ 7.28-7.36 (m, 3H), 7.11-7.13 (d, J=8.0 Hz, 2H), 6.83-6.85 (d, J=8.4 Hz, 2H), 4.26 (s, 1H), 4.03-4.25 (m, 5H), 3.71-3.89 (m, 8H), 3.32-3.34 (m, 3H), 3.27-3.32 (m, 1H), 2.02-2.05 (m, 2H); MS ES$^-$ (m/z): 539 (M+45)$^-$.

Example 27

The synthesis of compound CM within the invention is given below.

Preparation of 4-bromo-1-chloro-2-(4-(2-cyclobutoxyethoxy)benzyl)benzene (Intermediate CL)

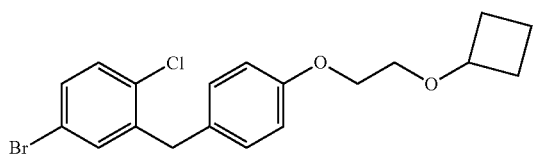

To a solution of cyclobutanol (260 mg, 3.6 mmol) in anhydrous tetrahydrofuran (4 mL) was added sodium hydride (138 mg, 5.7 mmol) in portions at 0° C. The mixture was stirred at 0° C. for 30 min, and then 2-(4-(5-bromo-2-chlorobenzyl)phenoxy)ethyl 4-methylbenzenesulfonate (intermediate AB) (300 mg, 0.6 mmol) was added in portions. The mixture was refluxed for 3 h, whereupon TLC showed the reaction was complete. The reaction mixture was quenched with saturated ammonium chloride, extracted with ethyl acetate, washed with water and and then with brine, dried over anhydrous sodium sulfate, and concentrated to a crude oil. The crude oil was purified by column chromatography (PE:EA=10:1) to get intermediate CL as an oil product (117 mg, yield: ~49%).

Preparation of (2S,3R,4R,5S,6R)-2-(4-chloro-3-(4-(2-cyclobutoxyethoxy)benzyl)phenyl)-6-(hydroxymethyl)tetrahydro-2H-pyran-3,4,5-triol (Compound CM)

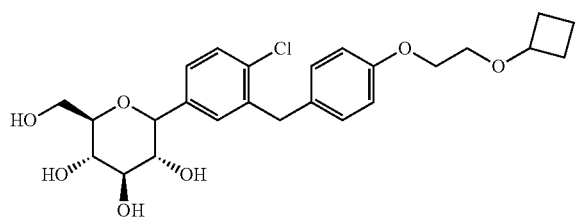

To a solution of 4-bromo-1-chloro-2-(4-(2-cyclobutoxyethoxy)benzyl)benzene (110 mg, 0.3 mmol) in anhydrous toluene/tetrahydrofuran (v/v=2/1, 2 mL) was added n-BuLi (0.17 mL, 2.5 M) dropwise at −78° C. The mixture was stirred for 30 min and then transferred to a solution of (3R,4S,5R,6R)-3,4,5-tris(trimethylsilyloxy)-6-((trimethylsilyloxy)methyl)tetrahydro-2H-pyran-2-one (195 mg, 0.4 mmol) in anhydrous toluene (1 mL) at −78° C. The mixture was stirred at −78° C. for 2 h until starting material was consumed. The reaction was quenched with methanesulfonic acid (54 µL in 1.4 mL methanol), and the mixture was allowed to warm to room temperature and stirred overnight. Then water was added, the organic phase was separated, and the water phase was extracted with ethyl acetate. The organic phases were combined, washed with saturated sodium bicarbonate, then with water and then with brine, and then dried over anhydrous sodium sulfate, filtered and concentrated to get the crude product. The crude product was dissolved in acetonitrile/dichloromethane (1.2 mL), triethylsilane (0.3 mL, 1.9 mmol) was added, the mixture was cooled to −40° C., and boron trifluoride diethyl etherate (1.8 µL, 1.4 mmol) was added quickly. After addition, the mixture was stirred for 2 h at 0° C. The reaction was quenched with saturated aqueous sodium bicarbonate. The volatiles were removed under reduced pressure, and the residue was extracted with ethyl acetate, washed with water and then with brine, and then dried over anhydrous sodium sulfate. The residue was filtered, concentrated, and purified by preparative LC-MS to obtain 16 mg of pure product. $^1$H NMR (CD$_3$OD, 400 MHz): δ 7.25-7.34 (m, 3H), 7.09-7.11 (m, 2H), 6.81-6.83 (m, 2H), 4.01-4.09 (m, 6H), 3.85-3.88 (m, 1H), 3.65-3.70 (m, 3H), 3.37-3.44 (m, 3H), 3.26-3.28 (m, 1H), 2.18-2.23 (m, 2H), 1.90-1.95 (m, 2H), 1.55-1.72 (m, 1H), 1.48-1.53 (m, 1H); MS ES$^-$ (m/z): 523 (M+45)$^-$; MS ES$^+$ (m/z): 479 (M+1)$^+$, 496 (M+18)$^+$.

Example 28

Figure 26:
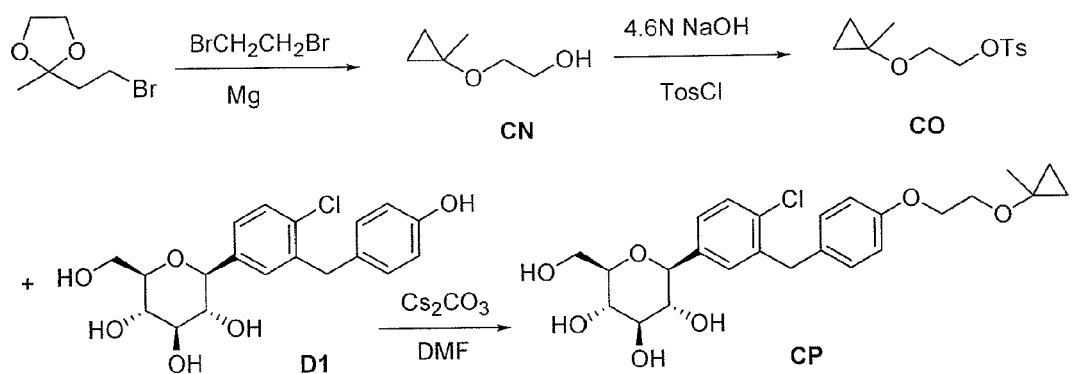
FIG. 26 is the outline for the synthesis of compound CP of the invention.

The synthesis of compound CP within the invention is outlined in FIG. 26, with the details given below.

Preparation of 2-(1-methylcyclopropoxy)ethanol (Intermediate CN)

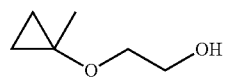

To Mg powder (250 mg, 10.25 mmol) suspended in THF (10 mL) was slowly added 1,2-dibromoethane (0.7 mL) over 3 h via funnel to maintain gentle reflux. After an additional 1 h, when the mixture had cooled to below 46° C., 2-(2-bromoethyl)-2-methyl-1,3-dioxolane (1 g, 5.1 mmol) was slowly added over 1 h to maintain the temperature below 46° C. An additional portion of THF (5 mL) was added, and the mixture was stirred overnight at 40~46° C. The reaction was quenched by addition to ammonium chloride at 0° C., and the mixture was stirred for 2 h before it was transferred to an extractor and separated. The organic layer was concentrated under vacuum, and the aqueous layer was extracted with dichloromethane (20 mL×2). The combined organic layers were washed with brine and concentrated to obtain crude product as a yellow oil (0.32 g, crude), which was used in the next step without further purification.

Preparation of 2-(1-methylcyclopropoxy)ethyl 4-methylbenzenesulfonate (Intermediate CO)

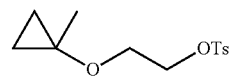

To the crude 2-(1-methylcyclopropoxy)ethanol from the previous step (0.32 g) in a mixture of 4.6N sodium hydroxide (6.3 mL, 2.52 mmol) and tetrahydrofuran (3 mL) was added 4-methylbenzene-1-sulfonyl chloride (2.1 g, 11.2 mmol) in dichloromethane (6 mL) at 0-5° C. The solution was stirred for 3 h at 0-5° C., and then extracted with dichloromethane. The organic layer was washed with brine, dried over sodium sulfate, and concentrated to obtain crude product (100 mg), which was used in the next step without further purification.

Preparation of (2S,3R,4R,5S,6R)-2-(4-chloro-3-(4-(2-(1-methylcyclopropoxy)ethoxy)benzyl)phenyl)-6-(hydroxymethyl)tetrahydro-2H-pyran-3,4,5-triol (Compound CP)

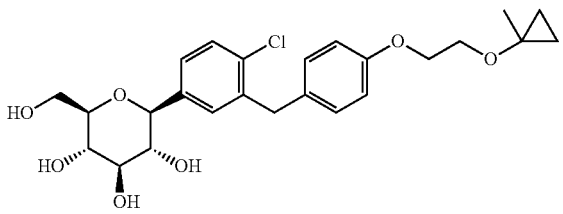

To a stirred suspension of (2S,3R,4R,5S,6R)-2-(4-chloro-3-(4-hydroxybenzyl)phenyl)-6-(hydroxymethyl)tetrahydro-2H-pyran-3,4,5-triol (intermediate D1) (140 mg, 0.26 mmol) in N,N-dimethylformamide (2 mL) and cesium carbonate (130 mg, 0.4 mmol) was added 2-(1-methylcyclopropoxy)ethyl 4-methylbenzenesulfonate (54 mg, 0.20 mmol). The mixture was stirred overnight at 50° C. The solution was diluted with water and the aqueous layer was extracted with ethyl acetate. The combined organic layers were concentrated under reduced pressure, and the residue was purified by preparative HPLC-MS to give 30 mg of white solid (31% yield; HPLC purity 97.5%). HPLC retention time: 3.27 min; Waters 2695 Separations Module equipped with a Waters 2996 Photodiode Array Detector and a Waters Micromass ZQ Detector; Waters XTerra C18 5 µm, 50 mm×2.1 mm column; 1.0 mL/min, detection at 190~400 nm; 6 min gradient 10-95% A, hold 8 min at 95% A; solvent A: 0.045% formic acid in acetonitrile, solvent B: 0.1% formic acid in Milli-Q water. $^1$H NMR (CD$_3$OD, 400 MHz): δ 7.28-7.36 (m, 3H), 7.12-7.14 (d, J=8.8 Hz, 2H), 6.83-6.86 (d, J=8.8 Hz, 2H), 4.64 (s, 1H), 4.02-4.12 (m, 5H), 3.81-3.91 (m, 3H), 3.71-3.73 (m, 1H), 3.28-3.48 (m, 5H), 1.42 (s, 3H), 0.0.81-0.83 (d, J=5.6 Hz, 2H), 0.44-0.46 (m, 2H); MS ES⁻ (m/z): 523 (M+45)⁻.

Example 29

Figure 27:
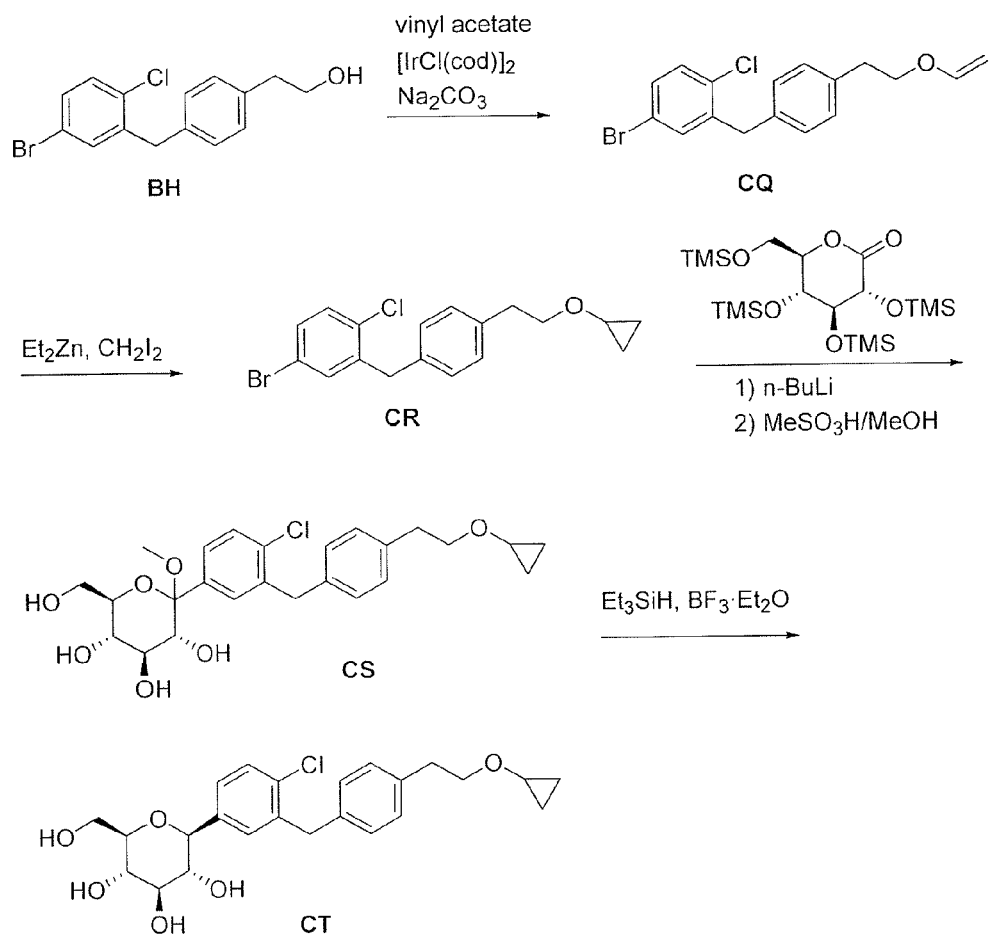
FIG. 27 is the outline for the synthesis of compound CT of the invention.

The synthesis of compound CT within the invention is outlined in FIG. 27, with the details given below.

Preparation of 4-bromo-1-chloro-2-(4-(2-(vinyloxy)ethyl)benzyl)benzene (Intermediate CQ)

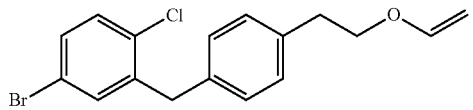

To a solution of 2-(4-(5-bromo-2-chlorobenzyl)phenyl)ethanol (intermediate BH) (500 mg, 1.46 mmol), [IrCl(cod)]₂ (9.8 mg, 0.015 mmol) and sodium carbonate (93 mg, 0.87 mmol) in toluene (2 mL) was added vinyl acetate (0.27 mL, 2.91 mmol) under argon. The reaction mixture was heated to 100° C. and stirred for 2 h. The solution was allowed to cool to room temperature, and then diluted with 50 mL of ethyl acetate. The mixture was washed with water (20 mL) and then with brine (20 mL), and dried over sodium sulfate. The residue was concentrated and purified by column chromatography (eluent EA:PE:Et₃N=1:20:0.01) to provide 445 mg of yellow solid. ¹H-NMR (CDCl₃, 400 MHz): δ 7.22~7.14 (m, 3H), 7.10 (d, 2H), 7.04 (d, 2H), 6.40 (dd, J=14.4 and 6.8 Hz, 1H), 4.11 (dd, J=14.4 and 2.0 Hz, 1H), 3.96 (s, 2H), 3.93 (dd, J=6.8 and 2.0 Hz, 1H), 3.82 (t, J=7.2 Hz, 2H), 2.88 (t, J=7.2 Hz, 2H).

Preparation of 4-bromo-1-chloro-2-(4-(2-cyclopropoxyethyl)benzyl)benzene (Intermediate CR)

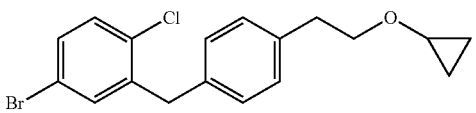

To a stirred mixture of 4-bromo-1-chloro-2-(4-(2-(vinyloxy)ethyl)benzyl)benzene (100 mg, 0.27 mmol) and Et₂Zn (0.68 mL, 0.68 mmol, 1.0 M in hexane) in dry ethyl ether (2 mL) was added diiodomethane (0.06 mL, 0.68 mmol) dropwise during 20 min at room temperature under argon. After stirring overnight, the reaction mixture was poured slowly into ice cold dilute hydrochloride solution with stirring. The mixture was extracted with ethyl acetate (3×10 mL). The combined organic layers were washed with water (10 mL) and then with brine (10 mL), and then dried over sodium sulfate. The residue was concentrated and purified by preparative TLC (eluent EA:PE=1:25) to obtain intermediate CR (86 mg) as a light yellow oil. ¹H-NMR (CDCl₃, 400 MHz): δ 7.32~7.24 (m, 3H), 7.18 (d, 2H), 7.12 (d, 2H), 4.05 (s, 2H), 3.73 (t, J=7.2 Hz, 2H), 3.32~3.29 (m, 1H), 2.88 (t, J=7.2 Hz, 2H), 0.57~0.44 (m, 4H).

Preparation of (3R,4S,5S,6R)-2-(4-chloro-3-(4-(2-cyclopropoxyethyl)benzyl)phenyl)-6-(hydroxymethyl)-2-methoxytetrahydro-2H-pyran-3,4,5-triol (Intermediate CS)

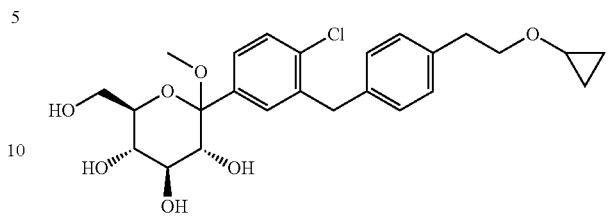

To a solution of 4-bromo-1-chloro-2-(4-(2-cyclopropoxyethyl)benzyl)benzene (105 mg, 0.29 mmol) in anhydrous toluene/THF (1.2 mL, v/v=2:1) was added dropwise n-BuLi (2.5 M in hexane, 0.14 mL) at −65° C., and the mixture was stirred for 30 min at −65° C. Then a −65° C. solution of (3R,4S,5R,6R)-3,4,5-tris(trimethylsilyloxy)-6-((trimethylsilyloxy)methyl)tetrahydro-2H-pyran-2-one (148 mg, 0.32 mmol) in toluene (1.2 mL) was added dropwise over 15 min. The mixture was stirred at −65° C. for 3 h until starting material was consumed. The reaction was quenched with methanesulfonic acid (0.04 mL, 0.60 mmol) in methanol (1 mL), and the mixture was allowed to warm to room temperature and stirred overnight. The reaction was quenched with saturated sodium bicarbonate, the organic phase was separated and the aqueous phase was extracted with ethyl acetate. The combined organic phases were washed with saturated bicarbonate, then with water, and then with brine, and dried over sodium sulfate. Removal of the volatiles afforded a residue (134 mg), which was used in the next step without further purification.

Preparation of (2S,3R,4R,5S,6R)-2-(4-chloro-3-(4-(2-cyclopropoxyethyl)benzyl)phenyl)-6-(hydroxymethyl)tetrahydro-2H-pyran-3,4,5-triol (Compound CT)

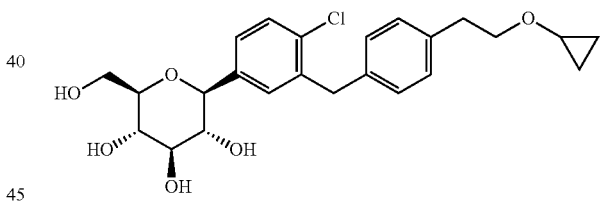

To a −15° C. solution of crude product from the previous step (134 mg, 0.28 mmol) in anhydrous acetonitrile/dichloromethane (2 mL, 1:1) was added triethylsilane (0.18 mL, 1.12 mmol). Then BF₃.Et₂O (0.11 mL, 0.84 mmol) was added dropwise, and the mixture was stirred for 3 h at −15° C. The reaction was quenched with saturated aqueous bicarbonate and the volatiles were removed under reduced pressure. The residue was extracted with ethyl acetate, washed with water, then with brine, and dried over sodium sulfate. The sample was concentrated and purified by preparative HPLC-MS to give 42 mg of white solid. ¹H NMR (CD₃OD, 400 MHz): δ 7.37~7.28 (m, 3H), 7.12 (s, 4H), 4.11 (d, J=9.2 Hz, 1H), 4.13~4.03 (dd, J=24.4 and 14.8 Hz, 2H), 3.88 (d, J=14.4 Hz, 1H), 3.72~3.68 (m, 3H), 3.48~3.39 (m, 3H), 3.32~3.28 (m, 2H), 2.80 (t, J=6.8 Hz, 2H), 0.47~0.44 (m, 4H); MS ESI (m/z): 449 [M+H]⁺, calc. 448.

Example 30

Figure 28:
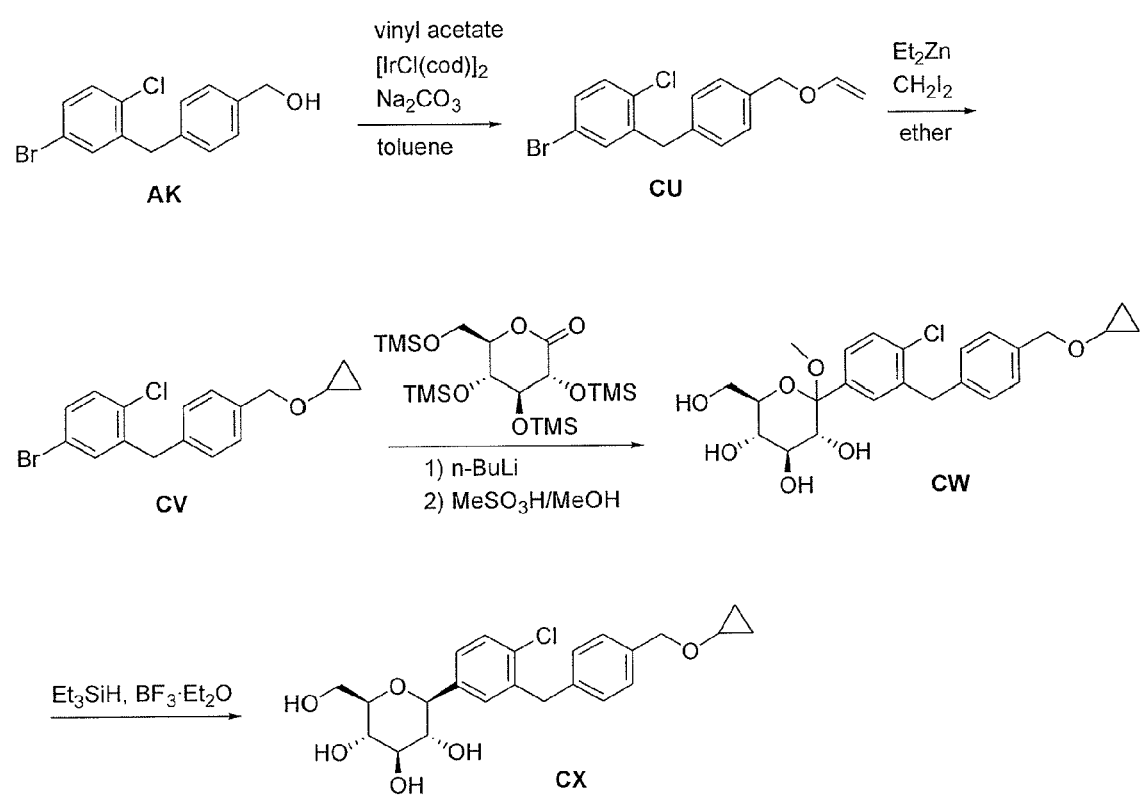
FIG. 28 is the outline for the synthesis of compound CX of the invention.

The synthesis of compound CX within the invention is outlined in FIG. 28, with the details given below.

Preparation of 4-bromo-1-chloro-2-(4-(vinyloxymethyl)benzyl)benzene (Intermediate CU)

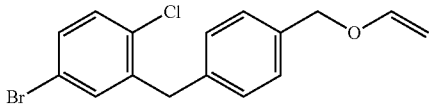

To a solution of (4-(5-bromo-2-chlorobenzyl)phenyl)methanol (intermediate AK) (1.5 g, 4.81 mmol), [IrCl(cod)]$_2$ (31 mg, 0.046 mmol) and sodium carbonate (0.29 g, 2.73 mmol) in toluene (6 mL) was added vinyl acetate (0.84 mL, 9.10 mmol) under argon. The reaction mixture was heated to 100° C. and stirred for 4 h. The solution was allowed to cool to room temperature, and then diluted with 50 mL of ethyl acetate. The mixture was washed with water (20 mL) and then with brine (20 mL), and dried over sodium sulfate. The residue was concentrated and purified by column chromatography (eluent EA:PE:Et$_3$N=1:30:0.01) to provide 1.09 g of white solid. $^1$H NMR (CDCl$_3$, 400 MHz): δ 7.36~7.28 (m, 5H), 7.22 (d, 2H), 6.61 (dd, J=14.4 and 6.8 Hz, 1H), 4.78 (s, 2H), 4.37~4.33 (dd, J=14.4 and 2.4 Hz, 1H), 4.14~4.12 (dd, J=6.8 and 2.4 Hz, 1H), 4.09 (s, 2H).

Preparation of 4-bromo-1-chloro-2-(4-(cyclopropoxymethyl)benzyl)benzene (Intermediate CV)

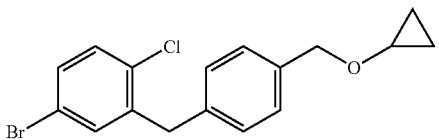

To a stirred mixture of 4-bromo-1-chloro-2-(4-(vinyloxymethyl)benzyl)benzene (0.7 g, 2.07 mmol) and Et$_2$Zn (5.18 mL, 5.18 mmol, 1.0 M in hexane) in dry ethyl ether (10 mL) was added diiodomethane (0.42 mL, 5.18 mmol) dropwise during 20 min at room temperature under argon. After stirring overnight, the reaction mixture was poured slowly into ice cold dilute hydrochloride solution with stirring. The mixture was extracted with ethyl acetate (3×20 mL). The combined organic layers were washed with water (20 mL) and then with brine (20 mL), and then dried over sodium sulfate. The residue was concentrated and purified by column chromatography (eluent EA:PE=1:200) to obtain intermediate CV (0.6 g) as a colorless oil. $^1$H NMR (CDCl$_3$, 400 MHz): δ 7.33~7.24 (m, 5H), 7.18 (d, 2H), 4.55 (s, 2H), 4.07 (s, 2H), 3.40~3.37 (m, 1H), 0.69~0.49 (m, 4H).

Preparation of (3R,4S,5S,6R)-2-(4-chloro-3-(4-(cyclopropoxymethyl)benzyl)phenyl)-6-(hydroxymethyl)-2-methoxytetrahydro-2H-pyran-3,4,5-triol (Intermediate CW)

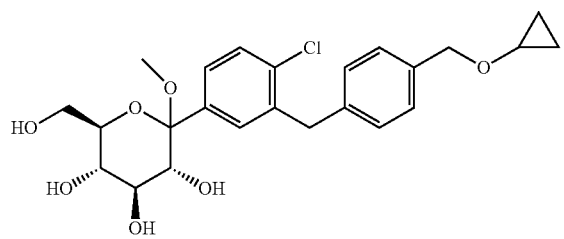

To a solution of 4-bromo-1-chloro-2-(4-(2-cyclopropoxymethyl)benzyl)benzene (0.6 g, 1.71 mmol) in anhydrous toluene/THF (6 mL, v/v=2:1) was added dropwise n-BuLi (2.5 M in hexane, 0.82 mL) at −65° C., and the mixture was stirred for 30 min at −65 ° C. Then a −65° C. solution of (3R,4S,5R,6R)-3,4,5-tris(trimethylsilyloxy)-6-((trimethylsilyloxy)methyl)tetrahydro-2H-pyran-2-one (0.87 g, 1.88 mmol) in toluene (6 mL) was added dropwise over 15 min. The mixture was stirred at −65° C. for 3.5 h until starting material was consumed. The reaction was quenched with methanesulfonic acid (0.23 mL, 3.58 mmol) in methanol (6 mL), and the mixture was allowed to warm to room temperature and stirred overnight. The reaction was quenched with saturated sodium bicarbonate, the organic phase was separated and the aqueous phase was extracted with ethyl acetate. The combined organic phases were washed with saturated bicarbonate, then with water, and then with brine, and dried over sodium sulfate. Removal of the volatiles afforded a residue (0.75 g), which was used in the next step without further purification.

Preparation of (2S,3R,4R,5S,6R)-2-(4-chloro-3-(4-(cyclopropoxymethyl)benzyl)phenyl)-6-(hydroxymethyl)tetrahydro-2H-pyran-3,4,5-triol (Compound CX)

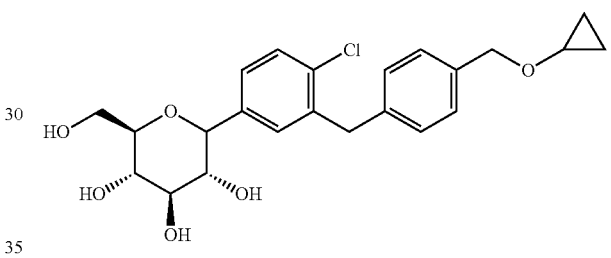

To a −15° C. solution of crude product from the previous step (0.75 g, 1.61 mmol) in anhydrous acetonitrile/dichloromethane (6 mL, 1:1) was added triethylsilane (1.01 mL, 6.42 mmol). Then BF$_3$.Et$_2$O (0.61 mL, 4.81 mmol) was added dropwise, and the mixture was stirred for 3 h at −15° C. The reaction was quenched with saturated aqueous bicarbonate and the volatiles were removed under reduced pressure. The residue was extracted with ethyl acetate, washed with water, then with brine, and dried over sodium sulfate. The sample was concentrated and purified by preparative HPLC-MS to give 0.35 g of white solid. $^1$H NMR (CD$_3$OD, 400 MHz): δ 7.38~7.30 (m, 3H), 7.25 (d, 2H), 7.19 (d, 2H), 4.52 (s, 2H), 4.13~4.07 (m, 3H), 3.91~3.88 (m, 1H), 3.73~3.68 (m, 1H), 3.49~3.35 (m, 4H), 3.32~3.28 (m, 1H), 0.61~0.47 (m, 4H); MS ESI (m/z): 435 [M+H]$^+$, calc. 434.

Example 31

The synthesis of compound DC within the invention is given below.

Preparation of 1-(4-(5-bromo-2-chlorobenzyl)phenoxy)propan-2-ol (Intermediate CY)

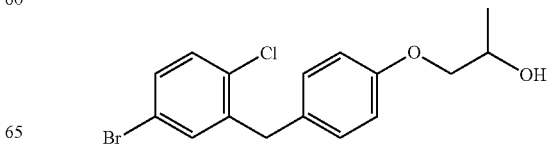

To a solution of 4-(5-bromo-2-chlorobenzyl)phenol (intermediate H) (3 g, 10.1 mmol) and cesium carbonate (6.6 g, 20.1 mmol) in N,N-dimethylacetamide (30 mL), 1-bromopropan-2-ol (2.8 g, 20.1 mmol) was added. The solution was heated to 80° C. and stirred overnight. Then the reaction mixture was cooled to room temperature, diluted with water, extracted with ethyl acetate, washed with sodium ammonium chloride and then with brine, and dried over sodium sulfate. The residue was concentrated and purified by column chromatography to intermediate CY (2.95 g, yield: 82%). ¹H NMR (CDCl₃, 400 MHz): δ 7.24-7.32 (m, 3H), 7.12-7.14 (m, 2H), 6.87-6.89 (m, 2H), 4.20-4.24 (m, 1H), 4.02 (s, 2H), 3.94-3.97 (m, 1H), 3.78-3.82 (m, 1H), 1.29-1.31 (m, 3H).

Preparation of 4-bromo-1-chloro-2-(4-(2-(1-ethoxyethoxy)propoxy)benzyl)benzene (Intermediate CZ)

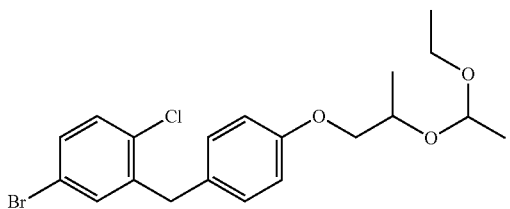

To a solution of 1-(4-(5-bromo-2-chlorobenzyl)phenoxy)propan-2-ol (857 mg, 2.4 mmol) in dichloromethane (20 mL) was added ethyl vinyl ether (1.2 mL, 12 mmol) and pyridinium p-toluenesulfonate (24 mg), and the mixture was stirred at room temperature for 2 h, whereupon starting material had been completely consumed as determined by TLC (eluent PE:EA=1:1). Solid sodium bicarbonate (5 g) was added, and the mixture was stirred for 10 min. Water (25 mL) was added, and the mixture was extracted with ethyl acetate, washed with sodium chloride, and dried over sodium sulfate. The residue was concentrated and purified by column chromatography to obtain intermediate CZ (900 mg, yield 87%) as a yellow oil. ¹H NMR (CDCl₃, 400 MHz): δ 7.23-7.30 (m, 3H), 7.09-7.11 (m, 2H), 6.85-6.87 (m, 2H), 4.86-4.94 (m, 1H), 4.10-4.13 (m, 1H), 4.00 (s, 2H), 3.84-3.99 (m, 1H), 3.69-3.72 (m, 1H), 3.50-3.59 (m, 1H), 1.19-1.37 (m, 9H).

Preparation of 4-bromo-1-chloro-2-(4-(2-(vinyloxy)propoxy)benzyl)benzene (Intermediate DA)

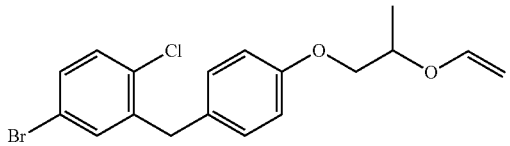

To a solution of 4-bromo-1-chloro-2-(4-(2-(1-ethoxyethoxy)propoxy)benzyl)-benzene (550 mg, 1.3 mmol) in dichloromethane (10 mL) at 0° C. under argon was added triethylamine (0.2 mL, 2.2 mmol), followed by trimethylsilyltrifluoromethane sulfonate (240 mg, 2.2 mmol). After 1 h, 1.0 M sodium hydroxide (4 mL) was added, followed by diethyl ether (20 mL). The organic phase was separated, dried over sodium sulfate and concentrated to an oil, which was purified by column chromatography (PE/EA=10:1) to obtain intermediate DA (290 mg, yield 59%).

Preparation of 4-bromo-1-chloro-2-(4-(2-cyclopropoxypropoxy)benzyl)benzene (Intermediate DB)

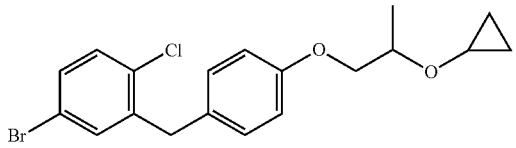

To a solution of diethyl zinc (1.9 mL, 1.0 M in hexane) in dichloromethane (10 mL) at 0° C. under argon was added slowly diiodomethane (0.15 mL) in dichloromethane (2 mL). After stirring for 30 min, 4-bromo-1-chloro-2-(4-(2-(vinyloxy)propoxy)benzyl)benzene (290 mg, 0.76 mmol) in dichloromethane (3 mL) was added dropwise. The reaction mixture was warmed to room temperature and stirred overnight, and then quenched with saturated aqueous ammonium chloride. The aqueous layer was extracted with ethyl acetate, and the combined organic layers were washed with saturated aqueous sodium bicarbonate and then with brine, and then dried over sodium sulfate. The residue was concentrated and purified by preparative TLC to obtain intermediate DB as an oil (200 mg, yield 66%). ¹H NMR (CDCl₃, 400 MHz): δ 7.24-7.31 (m, 3H), 7.10-7.12 (m, 2H), 6.87-6.89 (m, 2H), 3.90-4.01 (m, 5H), 3.47-3.48 (m, 1H), 1.31-1.33 (m, 3H), 0.64 (m, 2H), 0.50-0.53 (m, 2H).

Preparation of (2S,3R,4R,5S,6R)-2-(4-chloro-3-(4-(2-cyclopropoxypropoxy)benzyl)phenyl)-6-(hydroxymethyl)tetrahydro-2H-pyran-3,4,5-triol (Compound DC)

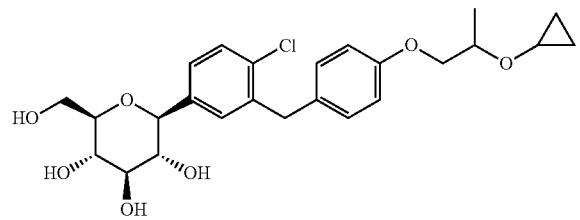

To a solution of 4-bromo-1-chloro-2-(4-(2-cyclopropoxypropoxy)benzyl)benzene (180 g, 0.45 mol) in anhydrous toluene/tetrahydrofuran (v/v=2:1, 1 mL), n-BuLi (0.22 mL, 2.5 M in hexane) was added dropwise at −78° C. The mixture was stirred for 30 min, and then transferred to a solution of (3R,4S,5R,6R)-3,4,5-tris(trimethylsilyloxy)-6-((trimethylsilyloxy)methyl)tetrahydro-2H-pyran-2-one (276 mg, 0.6 mmol) in anhydrous toluene (1 mL) at −78° C. The mixture was stirred at −78° C. for 2 h until starting material was consumed. The reaction was quenched with methanesulfonic acid (60 μL in 1.2 mL methanol), and the mixture was allowed to warm to room temperature and stirred overnight. Then water was added, the organic phase was separated, and the water phase was extracted with ethyl acetate. The organic phases were combined, washed with saturated sodium bicarbonate, then with water and then with brine, and then dried over anhydrous sodium sulfate. The residue was filtered and concentrated to get the crude product, which then was dissolved in acetonitrile/dichloromethane (2 mL, 1:1). Triethylsilane (0.3 mL, 1.9 mmol) was added, the mixture was cooled to −40° C., and boron trifluoride diethyl etherate (1.8 μL, 1.4 mmol) was added quickly. After addition, the mixture was stirred for 2 h at 0° C. The reaction was quenched with saturated aqueous sodium bicarbonate. The volatiles were removed under reduced pressure, and the residue was extracted with ethyl acetate and washed with water and then with brine, and then dried over anhydrous sodium sulfate. The residue was filtered, concentrated, and purified by prepared LC-MS to obtain compound DC (7.2 mg). $^1$H NMR (CD$_3$OD, 400 MHz): δ 7.28-7.37 (m, 3H), 7.11-7.13 (m, 2H), 6.83-6.85 (m, 2H), 3.88-4.12 (m, 7H), 3.69-3.73 (m, 1H), 3.40-3.53 (m, 4H), 3.28-3.33 (m, 1H), 1.27-1.29 (d, J=8 Hz, 3H), 0.48-0.60 (m, 4H); MS ES$^-$ (m/z): 523 (M+45)$^-$; MS ES$^+$ (m/z): 479 (M+1)$^+$, 496 (M+18)$^+$.

Example 32

Figure 29:
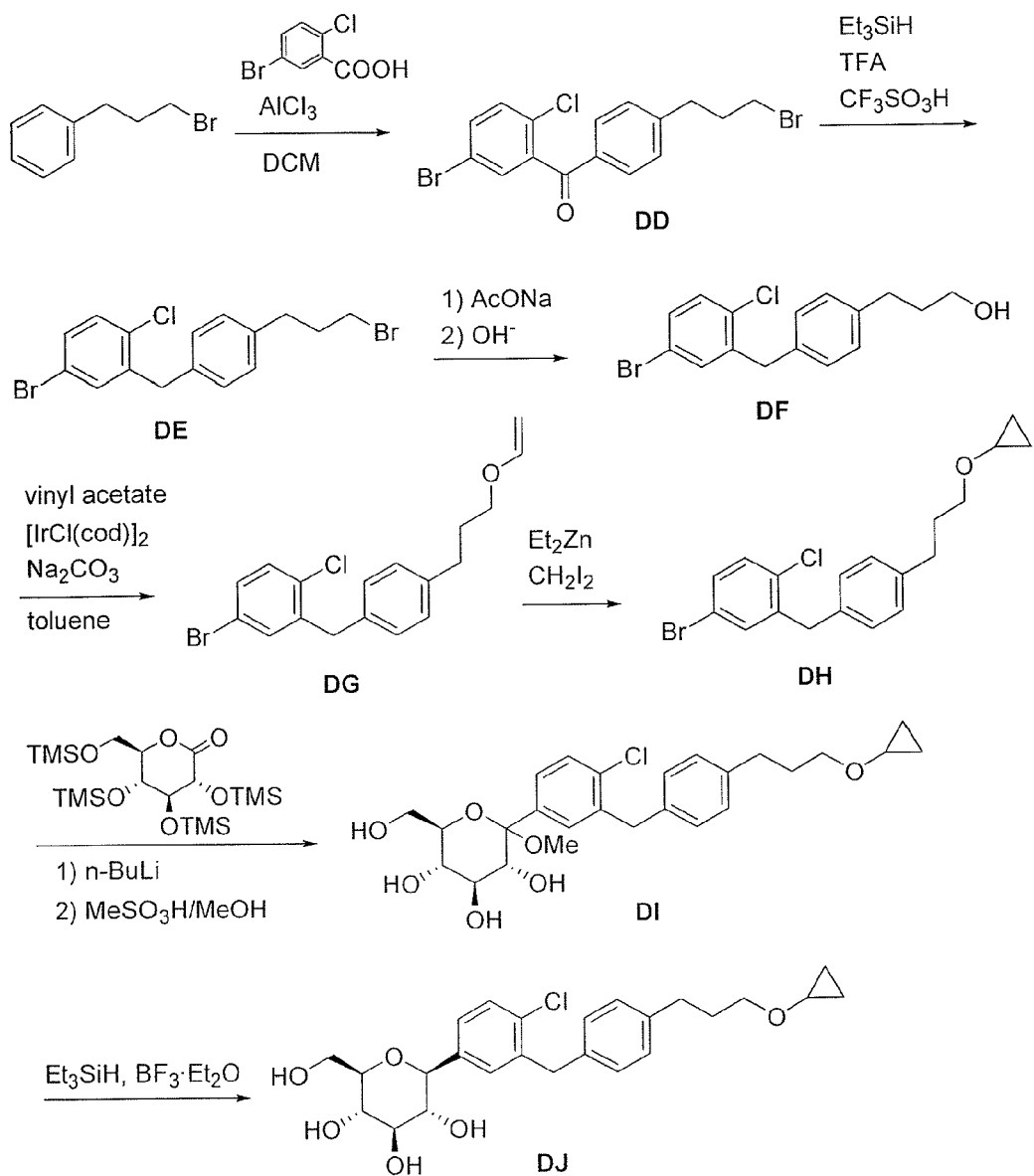
FIG. 29 is the outline for the synthesis of compound DJ of the invention.

The synthesis of compound DJ within the invention is outlined in FIG. 29, with the details given below.

Preparation of (5-bromo-2-chlorophenyl)(4-(3-bromopropyl)phenyl)methanone (Intermediate DD)

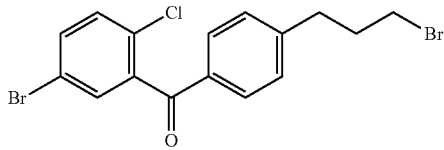

To a stirred suspension of 5-bromo-2-chlorobenzoic acid (2.31 g, 9.80 mmol) and oxalyl chloride (1.41 g, 11.11 mmol) in CH$_2$Cl$_2$ (30 mL) was added 0.05 mL of DMF. Once the vigorous evolution of gas ceased, the reaction was stirred overnight and then the volatiles were removed under reduced pressure. The resulting crude 5-bromo-2-chlorobenzoyl chloride was dissolved in dichloromethane (30 mL), and the solution was cooled to 0~5° C. Then AlCl$_3$ (1.31 g, 9.8 mmol) was added in portions, the mixture was stirred for 30 min, and (3-bromopropyl)benzene (1.50 g, 6.53 mmol) in dichloromethane (4 mL) was added. The reaction solution was warmed to room temperature and stirred for 4 h. The reaction was quenched by pouring into ice water. The suspension was diluted with water and extracted 3× with CH$_2$Cl$_2$. The combined organic extracts were washed 2× with 1N HCl, 1× with water, 2× with 1M NaOH, and 2× with brine, and then dried over Na$_2$SO$_4$. After removal of the volatiles, the crude product was purified by column chromatography (eluent EA:PE=1:20) to obtain intermediate DD (2.4 g) as a light yellow oil. $^1$H-NMR (CDCl$_3$, 400 MHz): δ 7.68~7.66 (d, 2H), 7.50~7.47 (dd, 1H), 7.42 (d, 1H), 7.28~7.19 (m, 3H), 3.33 (t, J=6.8 Hz, 2H), 2.80 (t, J=7.6 Hz, 2H), 2.17~2.10 (m, 2H).

Preparation of 4-bromo-2-(4-(3-bromopropyl)benzyl)-1-chlorobenzene (Intermediate DE)

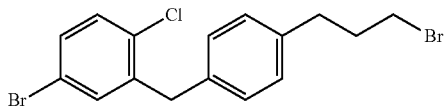

To a stirred solution of Et$_3$SiH (1.4 mL, 8.50 mmol) and (5-bromo-2-chlorophenyl)(4-(3-bromopropyl)phenyl)methanone (2.36 g, 5.67 mmol) in TFA (10 mL) at 30° C. was added CF$_3$SO$_3$H (0.05 mL). Within a few minutes the temperature of the solution increased causing it to reflux violently. After stirring for 2.5 h, additional Et$_3$SiH (0.45 mL, 2.85 mmol) was added and the mixture was heated to 50° C. After stirring for 4.5 h the reaction was complete, and the volatiles were removed under reduced pressure. The residue was poured into brine and extracted 3× with ethyl acetate. The combined organic layers were washed 3× with water, 2× with aqueous Na$_2$CO$_3$ and 2× with brine, and dried over Na$_2$SO$_4$. The solvent was evaporated under reduced pressure, and the residue (2.3 g) was used in the next step without further purification.

Preparation of 3-(4-(5-bromo-2-chlorobenzyl)phenyl)propan-1-ol (Intermediate DF)

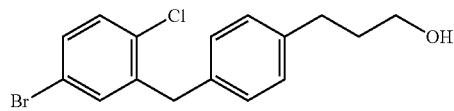

To a solution of 4-bromo-2-(4-(3-bromopropyl)benzyl)-1-chlorobenzene (2.3 g, 5.7 mmol) in DMF (12 mL) was added sodium acetate (0.7 g, 8.5 mmol). The solution was heated to 90° C. and stirred overnight. Water (50 mL) and ethyl acetate (100 mL) were added. The organic layer was separated, washed with saturated NH$_4$Cl, then with water and then with brine, and dried over Na$_2$SO$_4$. The solvent was evaporated under reduced pressure to obtain a yellow oil (2.3 g), which was dissolved in a mixture of THF:MeOH:H$_2$O (v/v/v=3:5:2, 10 mL). Sodium hydroxide (0.3 g, 7.23 mmol) was added, and the mixture was stirred for 1.5 h. The reaction was quenched with 20 mL of water, volatiles were removed under reduced pressure, and the residue was extracted with ethyl acetate (3×50 mL). The combined organic layers were washed with 2 N dilute hydrochloride (2×20 mL), then with water and then with brine, and then dried over sodium sulfate. After concentration, the residue was purified by column chromatography (eluent EA:PE=5:1) to obtain intermediate DF (1.6 g) as a yellow oil. $^1$H-NMR (CDCl$_3$, 400 MHz): δ 6 7.32~7.25 (m, 3H), 7.17 (d, 2H), 7.12 (d, 2H), 4.05 (s, 1H), 3.70 (t, J=6.8 Hz, 2H), 2.72 (t, J=7.6 Hz, 2H), 1.95~1.88 (m, 2H).

Preparation of 4-bromo-1-chloro-2-(4-(3-(vinyloxy)propyl)benzyl)benzene (Intermediate DG)

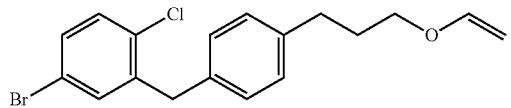

To a solution of 3-(4-(5-bromo-2-chlorobenzyl)phenyl) propan-1-ol (0.88 g, 2.59 mmol), [IrCl(cod)]$_2$ (17 mg, 0.026 mmol) and sodium carbonate (0.17 g, 1.56 mmol) in toluene (5 mL) was added vinyl acetate (0.48 mL, 5.18 mmol) under argon. The reaction mixture was heated to 100° C. and stirred for 5 h. The solution was allowed to cool to room temperature, and then diluted with 60 mL of ethyl acetate. The mixture was washed with water (20 mL) and then with brine (20 mL), and dried over sodium sulfate. The residue was concentrated and purified by column chromatography (eluent EA:PE:Et$_3$N=1:30:0.01) to provide 0.75 g of white solid. $^1$H NMR (CDCl$_3$, 400 MHz): δ 7.29~7.24 (m, 3H), 7.15 (d, 2H), 7.11 (d, 2H), 6.50 (dd, J=14.4 and 6.8 Hz, 1H), 4.18 (dd, J=14.4 and 2.0 Hz, 1H), 4.04 (s, 2H), 4.00 (dd, J=6.8 and 2.0 Hz, 1H), 3.71 (t, J=6.4 Hz, 2H), 2.70 (t, J=7.2 Hz, 2H), 2.06~1.96 (m, 2H).

Preparation of 4-bromo-1-chloro-2-(4-(3-cyclopropoxypropyl)benzyl)benzene (Intermediate DH)

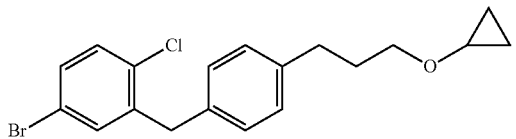

To a stirred mixture of 4-bromo-1-chloro-2-(4-(3-(vinyloxy)propyl)benzyl)benzene (0.75 g, 2.04 mmol) and Et$_2$Zn (5.11 mL, 5.11 mmol, 1.0 M in hexane) in dry ethyl ether (10 mL) was added diiodomethane (0.41 mL, 5.11 mmol) dropwise during 20 min at room temperature under argon. After stirring overnight, the reaction mixture was poured slowly into ice cold dilute hydrochloride solution with stirring. The mixture was extracted with ethyl acetate (3×20 mL). The combined organic layers were washed with water (20 mL) and then with brine (20 mL), and then dried over sodium sulfate. The residue was concentrated and purified by preparative TLC (eluent EA:PE=1:40) to obtain intermediate DH (0.64 g) as a light yellow oil. $^1$H NMR (CDCl$_3$, 400 MHz): δ 7.32~7.25 (m, 3H), 7.15 (d, 2H), 7.11 (d, 2H), 4.05 (s, 2H), 3.53 (t, J=6.4 Hz, 2H), 3.31~3.26 (m, 1H), 2.68 (t, J=7.2 Hz, 2H), 1.93~1.86 (m, 2H), 0.61~0.45 (m, 4H).

Preparation of (3R,4S,5S,6R)-2-(4-chloro-3-(4-(3-cyclopropoxypropyl)benzyl)phenyl)-6-(hydroxymethyl)-2-methoxytetrahydro-2H-pyran-3,4,5-triol (Intermediate DI)

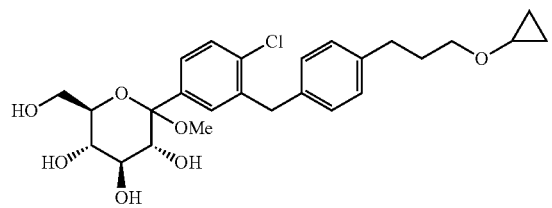

To a solution of 4-bromo-1-chloro-2-(4-(3-cyclopropoxypropyl)benzyl)benzene (0.64 g, 1.69 mmol) in anhydrous toluene/THF (6 mL, v/v=2:1) was added dropwise n-BuLi (2.5 M in hexane, 0.81 mL) at −65° C., and the mixture was stirred for 30 min at −65 ° C. Then a −65° C. solution of (3R,4S,5R,6R)-3,4,5-tris(trimethylsilyloxy)-6-((trimethylsilyloxy)methyl)tetrahydro-2H-pyran-2-one (0.86 g, 1.85 mmol) in toluene (6 mL) was added dropwise over 15 min. The mixture was stirred at −65° C. for 3.5 h until starting material was consumed. The reaction was quenched with methanesulfonic acid (0.23 mL, 3.58 mmol) in methanol (6 mL), and the mixture was allowed to warm to room temperature and stirred overnight. The reaction was quenched with saturated sodium bicarbonate, the organic phase was separated and the aqueous phase was extracted with ethyl acetate. The combined organic phases were washed with saturated bicarbonate, then with water, and then with brine, and dried over sodium sulfate. Removal of the volatiles afforded a residue (0.73 g), which was used in the next step without further purification.

Preparation of (2S,3R,4R,5S,6R)-2-(4-chloro-3-(4-(3-cyclopropoxypropyl)benzyl)phenyl)-6-(hydroxymethyl)tetrahydro-2H-pyran-3,4,5-triol (Compound DJ)

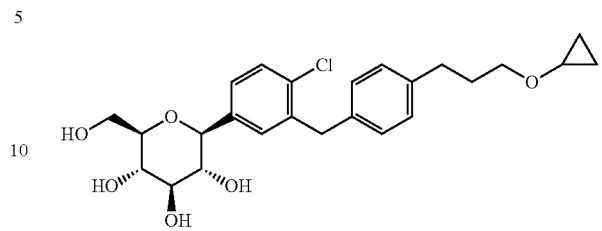

To a −15° C. solution of crude product from the previous step (0.60 g, 1.22 mmol) in anhydrous acetonitrile/dichloromethane (6 mL, 1:1) was added triethylsilane (0.78 mL, 4.87 mmol). Then BF$_3$.Et$_2$O (0.46 mL, 3.65 mmol) was added dropwise, and the mixture was stirred for 3 h at −15° C. The reaction was quenched with saturated aqueous bicarbonate and the volatiles were removed under reduced pressure. The residue was extracted with ethyl acetate, washed with water, then with brine, and dried over sodium sulfate. The sample was concentrated and purified by preparative HPLC-MS to give 0.29 g of white solid. $^1$H NMR (CD$_3$OD, 400 MHz): δ 7.38~7.29 (m, 3H), 7.12 (d, 2H), 7.09 (d, 2H), 4.11 (d, J=9.2 Hz, 1H), 4.13~4.03 (dd, J=24.4 and 14.8 Hz, 2H), 3.91~3.88 (m, 1H), 3.73~3.68 (m, 1H), 3.50 (t, J=6.4 Hz, 2H), 3.47~3.40 (m, 3H), 3.30~3.27 (m, 2H), 2.62 (t, J=7.2 Hz, 2H), 1.87~1.80 (m, 2H), 0.54~0.44 (m, 4H); MS ESI (m/z): 463 [M+H]$^+$, calc. 462.

Example 33

Figure 30:
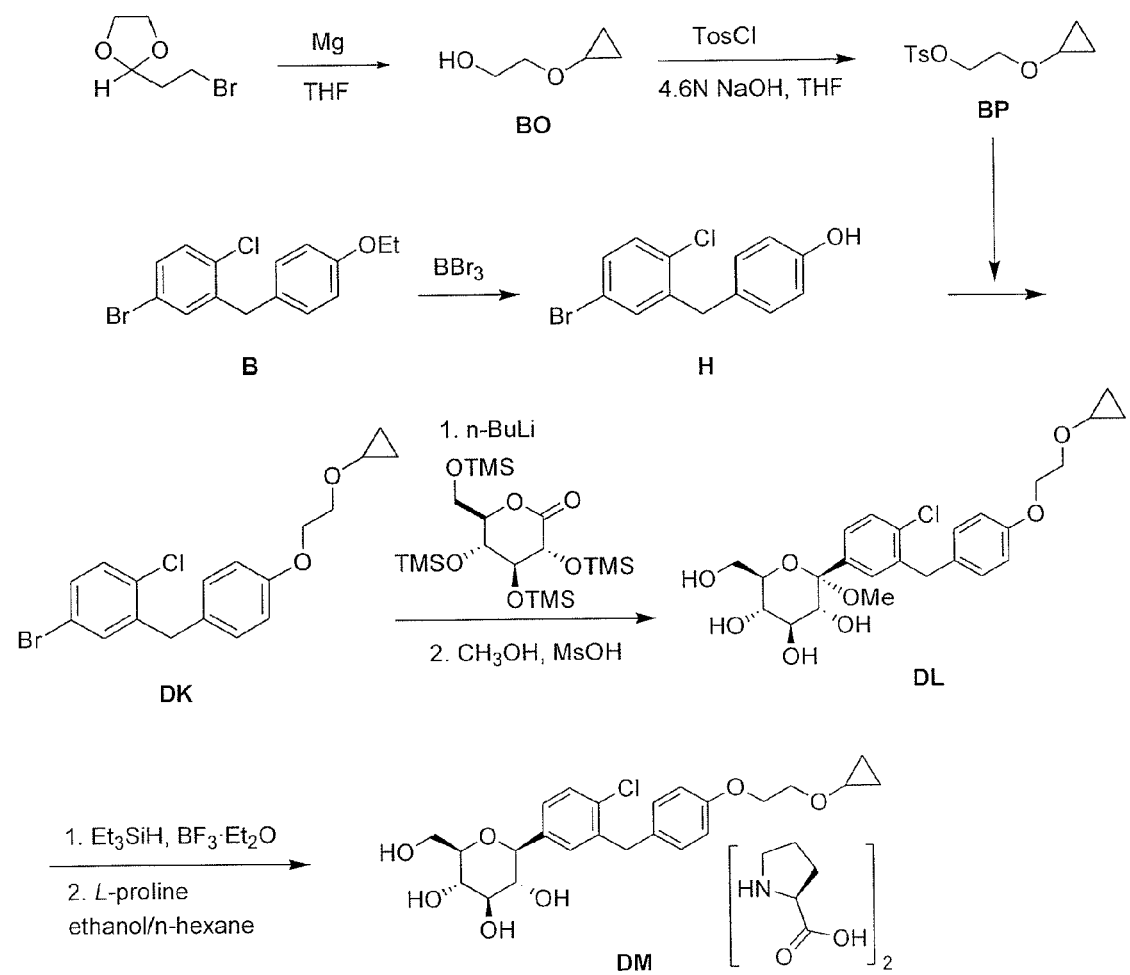
FIG. 30 is the outline for the synthesis of complex DM of the invention.

The synthesis of complex DM within the invention is outlined in FIG. 30, with the details given below.

Preparation of 2-cyclopropoxyethanol (Intermediate BO)

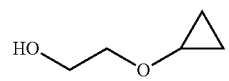

To a suspension of Mg powder (86.7 g, 3.6 mol) and I$_2$ (catalytic) in anhydrous THF (0.7 L) was added slowly 1,2-dibromoethane (460 g, 2.4 mol) in anhydrous THF (2 L) at a rate that maintained the reaction temperature between 40-55° C. A solution of 2-(2-bromoethyl)-1,3-dioxolane (100 g, 0.56 mol) in anhydrous THF (750 mL) was added dropwise, and the reaction mixture was kept at 40-55° C. for 16 h. The reaction was quenched by addition of an aqueous solution of ammonium chloride. The mixture was extracted with methylene chloride. The organic layer was dried over sodium sulfate, and concentrated to give intermediate BO (27 g) as yellow oil, which was used in the next step without further purification.

Preparation of 2-cyclopropoxyethyl 4-methylbenzenesulfonate (Intermediate BP)

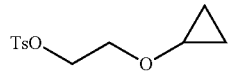

To a stirred solution of sodium hydroxide (32 g, 0.8 mol) in water (180 mL) and THF (180 mL) was added crude 2-cyclopropoxyethanol from the previous step (27 g, 0.26 mol) at −5 to 0° C. A solution of p-toluenesulfonyl chloride (52 g, 0.27 mol) in THF (360 mL) was added dropwise, and the reaction mixture was kept at −5 to 0° C. for 16 h. The reaction mixture was then incubated at room temperature for 30 min, the organic layer was separated and the aqueous layer was extracted with ethyl acetate (2×1.0 L). The combined organic layers were washed with brine, dried over $Na_2SO_4$ and concentrated to get the crude intermediate BP as a yellow oil (53.3 g), which was used for the preparation of intermediate DK below without further purification.

Preparation of 4-(5-bromo-2-chlorobenzyl)phenol (Intermediate H)

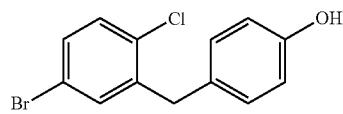

To a stirred solution of 4-bromo-1-chloro-2-(4-ethoxybenzyl)benzene (intermediate B) (747 g, 2.31 mol) in dichloromethane was added slowly boron tribromide (1.15 kg, 4.62 mol) at −78° C. The reaction mixture was allowed to warm to room temperature. When the reaction was complete as measured by TLC, the reaction was quenched with water. The mixture was extracted with dichloromethane. The organic layer was washed with an aqueous solution of saturated sodium bicarbonate, then with water, and then with brine, and dried over $Na_2SO_4$. The residue was concentrated and then recrystallized in petroleum ether to obtain intermediate H as a white solid (460 g, yield 68%). $^1$H NMR ($CDCl_3$, 400 MHz): δ 7.23~7.29 (m, 3H), 7.08 (d, J=8.8 Hz, 2H), 6.79 (d, J=8.8 Hz, 2H), 5.01 (s, 1H), 4.00 (s, 2H).

Preparation of 4-bromo-1-chloro-2-(4-(2-cyclopropoxyethoxy)benzyl)benzene (Intermediate DK)

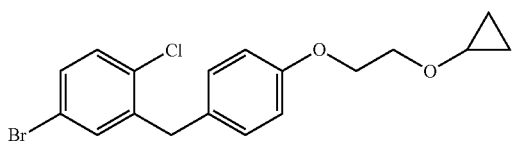

A mixture of 4-(5-bromo-2-chlorobenzyl)phenol (56.7 g, 210 mmol) and $Cs_2CO_3$ (135 g, 420 mmol) in DMF (350 mL) was stirred at room temperature for 30 min, and then 2-cyclopropoxyethyl 4-methylbenzenesulfonate (crude intermediate BP from the second preceeding step above) (53.3 g, 210 mmol) was added. The reaction mixture was stirred at room temperature overnight, and then diluted with water (3 L) and extracted with EtOAc. The organic layer was washed with water, then with brine, and dried over $Na_2SO_4$. The residue was concentrated and then purified by flash column chromatography on silica gel (eluent PE:EA=10:1) to give intermediate DK as a liquid (51 g, yield 64%). $^1$H NMR ($CDCl_3$, 400 MHz): δ 7.22~7.29 (m, 3H), 7.08 (d, J=8.8 Hz, 2H), 6.88 (d, J=8.8 Hz, 2H), 4.10 (t, J=4.8 Hz, 2H), 3.86 (t, J=4.8 Hz, 2H), 3.38-3.32 (m, 1H), 0.62-0.66 (m, 2H), 0.49-0.52(m, 2H).

Preparation of (2S,3R,4S,5S,6R)-2-(4-chloro-3-(4-(2-cyclopropoxyethoxy)benzyl)phenyl)-6-(hydroxymethyl)-2-methoxytetrahydro-2H-pyran-3,4,5-triol (Intermediate DL)

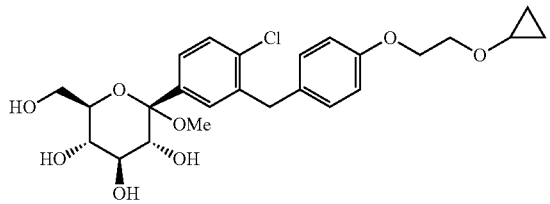

To a stirred solution of 4-bromo-1-chloro-2-(4-(2-cyclopropoxyethoxy)benzyl)benzene (213 g) in anhydrous THF/toluene (1:2 v/v, 1.7 L) under argon was added n-BuLi (2.5 M in hexane, 245.9 mL) dropwise at −60±5° C. The mixture was stirred for 30 min, and then transferred to a stirred solution of (3R,4S,5R,6R)-3,4,5-tris(trimethylsilyloxy)-6-((trimethylsilyloxy)methyl)tetrahydro-2H-pyran-2-one (310.5 g) in toluene (1.6 L) at −60±5° C. The reaction mixture was continuously stirred at −60±5° C. for 1 h before quenching with an aqueous solution of saturated ammonium chloride (1.5 L). The mixture was allowed to warm to room temperature and stirred for 1 h. The organic layer was separated and the water layer was extracted with ethyl acetate (3×500 mL). The combined organic layers were washed with brine (1 L), dried over $Na_2SO_4$, and concentrated. The residue was dissolved in methanol (450 mL), and methanesulfonic acid (9.2 mL) was added at 0° C. The solution was allowed to warm to room temperature and stirred for 20 h. The reaction was quenched with an aqueous solution of sodium bicarbonate (50 g) in water (500 mL) and then additional water (900 mL) was added. The mixture was extracted with ethyl acetate (3×1.0 L). The combined organic layers were washed with brine, dried over $Na_2SO_4$, and concentrated. The crude product was used in the next step without further purification.

Preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, bis(L-proline) Complex (Complex DM)

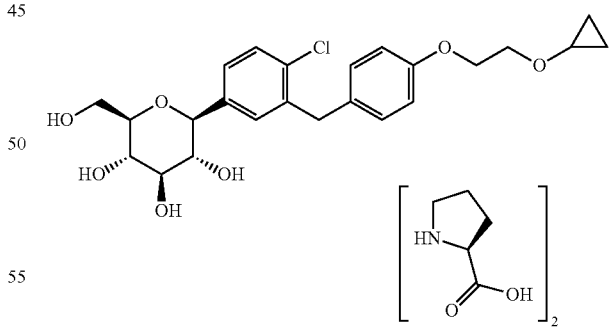

To a stirred solution of crude (2S,3R,4S,5S,6R)-2-(4-chloro-3-(4-(2-cyclopropoxyethoxy)benzyl)phenyl)-6-(hydroxymethyl)-2-methoxytetrahydro-2H-pyran-3,4,5-triol from the previous step in $CH_2Cl_2/CH_3CN$ (1:1, 1.3 L) at −5° C. was added triethylsilane (28.2 mL, 563 mmol), followed by $BF_3 \cdot Et_2O$ (52.3 mL, 418.9 mmol). The reaction was stirred for 16 h while the temperature was allowed to warm gradually to room temperature. The reaction was quenched by addition of an aqueous solution of saturated sodium bicarbonate to pH 8.0. The organic volatiles were removed under vacuum. The residue was partitioned between ethyl acetate (2.25 L) and water (2.25 L). The organic layer was separated, washed with brine, dried over $Na_2SO_4$ and concentrated to give the crude product (230 g, purity 82.3%). To the crude product was added L-proline (113.7 g) in $EtOH/H_2O$ (15:1 v/v, 2.09 L), and the mixture was stirred at 80° C. for 1 h until it became a clear solution. Hexane (3.0 L) was added dropwise over 50 min, while the temperature was maintained at about 60° C. The reaction mixture was stirred overnight at room temperature. The solid was filtered and washed with $EtOH/H_2O$ (15:1 v/v, 2×300 mL), hexane (2×900 mL), and dried at 45° C. under vacuum for 10 h to give pure complex DM as a white solid (209 g; HPLC purity 99.2% (UV)). $^1H$ NMR ($CD_3OD$, 400 MHz): δ 7.25~7.34 (m, 3H), 7.11 (d, J=8.8 Hz, 2H), 6.84 (d, J=8.8 Hz, 2H), 4.03-4.11 (m, 5H), 3.96-4.00 (m, 2H), 3.83-3.90 (m, 3H), 3.68-3.72 (m, 1H), 3.36-3.46 (m, 6H), 3.21-3.30 (m, 3H), 2.26-2.34 (m, 2H), 2.08-2.17 (m, 2H), 1.94-2.02 (m, 4H), 0.56-0.57 (m, 2H), 0.52-0.53 (m, 2H).

Figure 31:
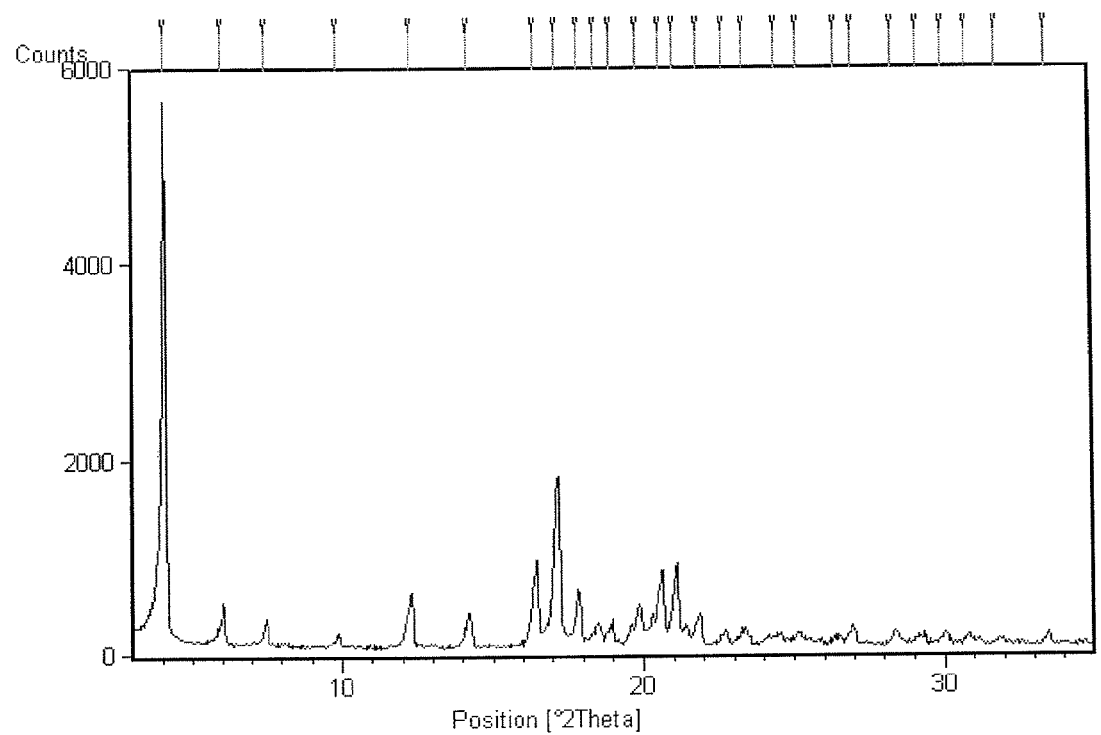
FIG. 31 is the X-ray powder diffraction pattern of complex DM of the invention.
Figure 32:
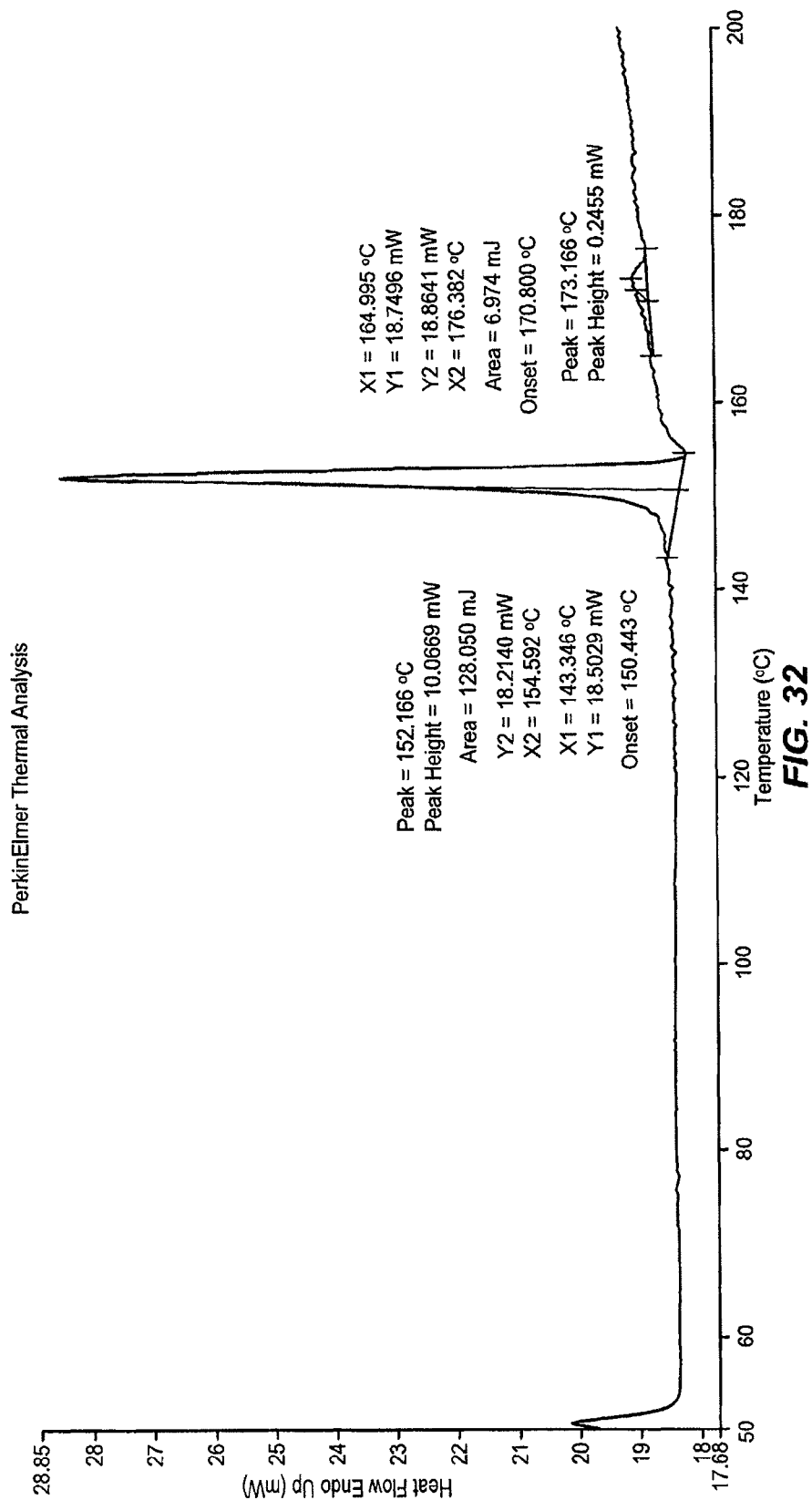
FIG. 32 is the differential scanning calorimetry spectrum of complex DM of the invention.

Crystalline complex DM was analyzed by X-ray powder diffraction using $CuK_{\alpha1}$ radiation. The diffraction pattern is shown in FIG. 31 and summarized in Table 1 (only peaks up to 30° in 2θ are listed). The melting point of complex DM was determined by differential scanning calorimetry (DSC) as 151±1° C. (evaluated as onset-temperature; heating from 50° C. to 200° C. at 10° C./min). The DSC spectrum is shown in FIG. 32.

TABLE 1

| Position [°2θ] | d-spacing [Å] | Relative Intensity[%] |
|---|---|---|
| 4.08 | 21.62 | 100.0 |
| 6.04 | 14.63 | 8.1 |
| 7.50 | 11.77 | 5.3 |
| 9.88 | 8.95 | 2.3 |
| 12.31 | 7.18 | 9.9 |
| 14.22 | 6.22 | 6.7 |
| 16.44 | 5.39 | 16.3 |
| 17.18 | 5.16 | 30.9 |
| 17.89 | 4.96 | 9.6 |
| 18.47 | 4.80 | 4.1 |
| 18.97 | 4.67 | 4.0 |
| 19.85 | 4.47 | 7.7 |
| 20.60 | 4.31 | 14.1 |
| 21.10 | 4.21 | 14.8 |
| 21.88 | 4.06 | 5.9 |
| 22.72 | 3.91 | 2.7 |
| 23.38 | 3.80 | 2.8 |
| 24.49 | 3.63 | 2.1 |
| 25.17 | 3.54 | 2.5 |
| 26.43 | 3.37 | 1.4 |
| 26.97 | 3.30 | 3.1 |
| 28.36 | 3.14 | 2.2 |
| 29.23 | 3.05 | 1.6 |

Example 34

The SGLT inhibitory effects of the compounds of the present invention were demonstrated by the following procedures.

Preparation of Human SGLT2 Expression Vector

A full-length cDNA clone expressing human SGLT2 (GenScript Corporation) was subcloned into Hind III and Not I sites of pEAK15 expression vector. Clones harboring the cDNA inserts were identified by restriction analysis.

Preparation of a Cell Line Stably Expressing Human SGLT2

Plasmid containing human SGLT2 was linearized with Nsi I and purified by agarose gel electrophoresis. Using Lipofectamine 2000 Transfection Reagent (Invitrogen Corporation), DNA was transfected into HEK293.ETN cells and cultured in Dulbecco's Modified Eagle Medium (DMEM) containing 10% fetal bovine serum (FBS) at 37° C. under 5% $CO_2$ for 24 h. Transfectants were selected in the same growth medium supplemented with puromycin (Invitrogen Corporation) for two weeks. Puromycin-resistant cells were recovered and seeded on a fresh 96-well plate (single cell per well) and cultured in the presence of puromycin until cells became confluent. Puromycin-resistant clones were evaluated for SGLT2 activity in the methyl-α-D[U-$^{14}$C]glucopyranoside uptake assay described below. The clone that exhibited the highest signal-to-background ratio was used for the methyl-α-D[U-$^{14}$C]glucopyranoside uptake assay.

Preparation of Human SGLT1 Expressing Cells

Full-length human SGLT1 cDNA on pDream2.1 expression vector was obtained from GenScript Corporation and propagated in *Escherichia coli* strain DH5α using Luria-Bertani (LB) medium containing ampicillin. Plasmid DNA was isolated using the QIAGEN Plasmid Midi Kit (QIAGEN Inc.). Human SGLT1 expression plasmid DNA was transfected into COS-7 cells (American Type Culture Collection) using Lipofectamine 2000 Transfection Reagent according to a manufacturer suggested protocol. Transfected cells were stored in DMEM containing 10% dimethyl sulfoxide (DMSO) at −80° C.

Methyl-α-D-[U$^{14}$C]glucopyranoside Uptake Assay

Cells expressing SGLT1 or SGLT2 were seeded on 96-well ScintiPlate scintillating plates (PerkinElmer, Inc.) in DMEM containing 10% FBS (1×10$^5$ cells per well in 100 μl medium) incubated at 37° C. under 5% $CO_2$ for 48 h prior to the assay. Cells were washed twice with 150 μl of either sodium buffer (137 mM NaCl, 5.4 mM KCl, 2.8 mM $CaCl_2$, 1.2 mM $MgCl_2$, 10 mM tris(hydroxymethyl)aminomethane/N-2-hydroxyethylpiperazine-N'-ethanesulfonic acid [Tris/Hepes], pH 7.2) or sodium-free buffer (137 mM N-methyl-glucamine, 5.4 mM KCl, 2.8 mM $CaCl_2$, 1.2 mM $MgCl_2$, 10 mM Tris/Hepes, pH 7.2). Test compound in 50 μl each of sodium or sodium-free buffer containing 40 μCi/ml methyl-α-D-[U-$^{14}$C]glucopyranoside (Amersham Biosciences/GE Healthcare), either with (symbols in parentheses) or without (symbols without parentheses) 25% human serum, was added per well of a 96-well plate and incubated at 37° C. with shaking for either 2 h (SGLT1 assay) or 1.5 h (SGLT2 assay). Cells were washed twice with 150 μl of wash buffer (137 mM N-methylglucamine, 10 mM Tris/Hepes, pH 7.2) and methyl-α-D-[U-$^{14}$C] glucopyranoside uptake was quantitated using a TopCount scintillation counter (PerkinElmer, Inc.). Sodium-dependent glucopyranoside uptake was measured by subtracting the values obtained with sodium-free buffer from those obtained using sodium buffer (average of triplicate determinations).

TABLE 2

| Compound | $IC_{50}$* SGLT2 | SGLT1 |
|---|---|---|
| M | + | ++ |
| P | (+) | (++) |
| R | (+) | (++) |
| T | (+) | (+++) |
| X | (+) | (++) |
| Z | (+) | (+++) |
| AD | (+) | (++) |
| AV | (+) | (+++) |
| BN | (+) | (+++) |
| BQ | (+) | (++) |
| BT | (+) | (++) |

TABLE 2-continued

| Compound | IC$_{50}$* | |
| --- | --- | --- |
| | SGLT2 | SGLT1 |
| BW | (+) | (+++) |
| BZ | (+) | (+++) |
| CC | + | ++ |
| CF | + | ++ |
| CH | (+) | (++) |
| CK | (+) | (++) |
| CM | (+) | (+++) |
| CP | (+) | (+++) |
| CT | (+) | (+++) |
| CX | (+) | (+++) |
| DC | (+) | (++) |
| DJ | (+) | (++) |

*Key:
+ <1 μM
++ 1 μM to 10 μM
+++ >10 μM
( ) indicates incubation with 25% human serum

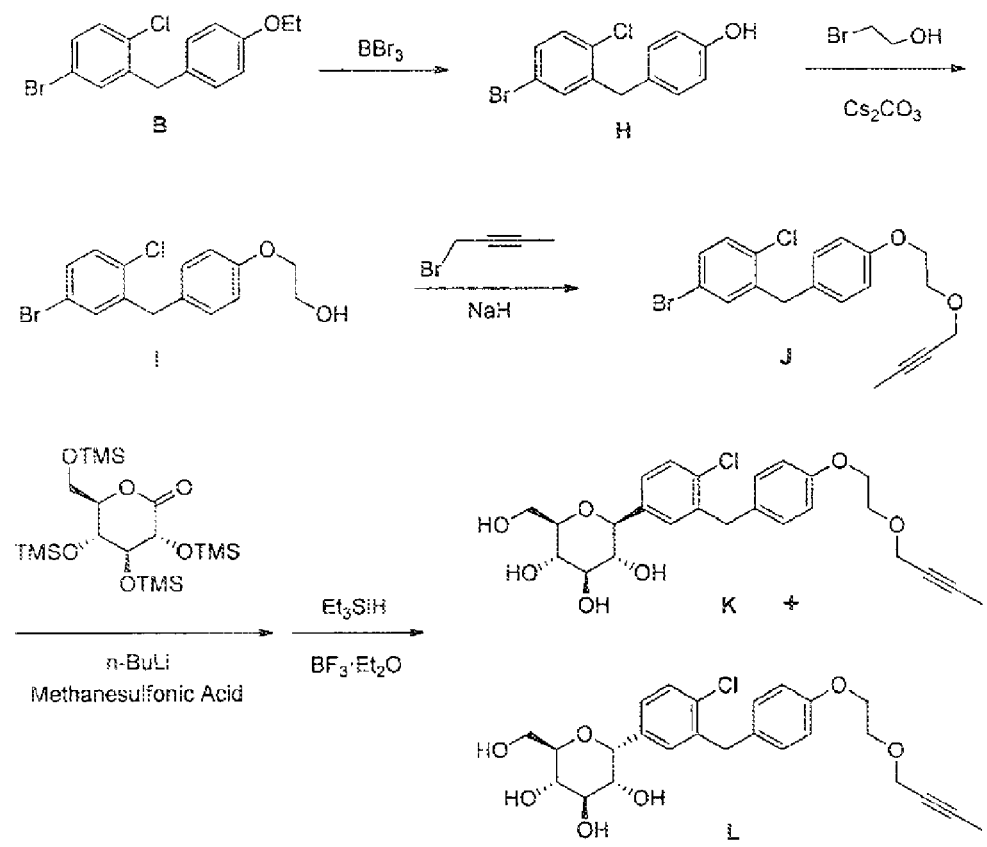

What is claimed is:

1. A method of treating a disease or condition selected from the group consisting of type 1 diabetes mellitus, type 2 diabetes mellitus and obesity, said method comprising administering to a subject in need thereof a therapeutically effective amount of a compound of the formula:

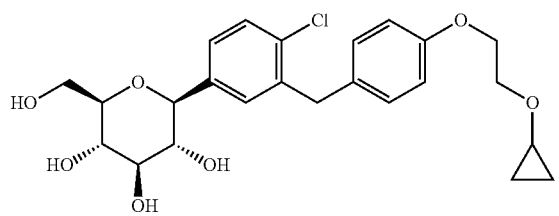

or a pharmaceutically acceptable salt thereof.

2. The method of claim 1, wherein said disease or condition is type 1 diabetes mellitus.

3. The method of claim 1, wherein said disease or condition is type 2 diabetes mellitus.

4. The method of claim 1, wherein said disease or condition is obesity.

5. The method of claim 1, wherein said compound is administered in combination with a second therapeutic agent.

6. The method of claim 5, wherein said second therapeutic agent is selected from the group consisting of antidiabetic agents, lipid-lowering/lipid-modulating agents, agents for treating diabetic complications, anti-obesity agents, antihypertensive agents, antihyperuricemic agents, and agents for treating chronic heart failure or atherosclerosis.

7. The method of claim 6, wherein said antidiabetic agent is selected from the group consisting of insulin and insulin mimetics, sulfonylureas, insulin secretion enhancers, biguanides, sulfonylurea/ biguanide combinations, meglitinides, thiazolidinediones, thiazolidinedione/ biguanide combinations, oxadiazolidinediones, PPAR-gamma agonists, PPAR-alpha/gamma dual agonists, PPAR-alpha/gamma/delta pan agonists, retinoid X receptor agonists, alpha-glucosidase inhibitors, stimulants of insulin receptor tyrosine kinase, tripeptidyl peptidase II inhibitors, dipeptidyl peptidase IV inhibitors, protein tyrosine phosphatase-1B inhibitors, glycogen phosphorylase inhibitors, glucose-6-phosphatase inhibitors, fructose 1,6-bisphosphatase inhibitors, pyruvate dehydrogenase inhibitors, imidazoline derivatives, hepatic gluconeogenesis inhibitors, D-chiroinositol, glycogen synthase kinase-3 inhibitors, incretin mimetics, GLP-1, GLP-1 analogs, GLP-1 receptor agonists, amylin, amylin analogs and agonists, aP2 inhibitors, beta-3 adrenergic receptor agonists, and other insulin sensitivity enhancers.

8. The method of claim 7, wherein said sulfonylurea is selected from the group consisting of glibornuride, gliclazide, glimepiride, glipizide, gliquidone, glisoxepide, glyburide, and glyclopyramide.

9. The method of claim 7, wherein said biguanide is metformin.

10. The method of claim 7, wherein said meglitinide is selected from the group consisting of repaglinide, nateglinide, and mitiglinide.

11. The method of claim 7, wherein said thiazolidinedione is selected from the group consisting of rosiglitazone, pioglitazone, and CLX-0921.

12. The method of claim 7, wherein said alpha-glucosidase inhibitor is selected from the group consisting of acarbose and miglitol.

13. The method of claim 7, wherein said dipeptidyl peptidase IV inhibitor is selected from the group consisting of sitagliptin, saxagliptin and vildagliptin.

14. The method of claim 7, wherein said incretin mimetic is exenatide.

15. The method of claim 7, wherein said GLP-1 analog is liraglutide.

16. The method of claim 7, wherein said amylin analog is pramlintide.

17. The method of claim 6, wherein said anti-obesity agent is selected from the group consisting of serotonin-norepinephrine reuptake inhibitors, norepinephrine-dopamine reuptake inhibitors, selective serotonin reuptake inhibitors, selective norepinephrine reuptake inhibitors, norepinephrine releasing stimulants, anorexiants, dopamine agonists, H$_3$-histamine antagonists, 5-HT2c receptor agonists, beta-3 adrenergic receptor agonists, cholecystokinin agonists, antidepressant/acetylcholinesterase inhibitor combinations, lipase inhibitors, anti-epileptic agents, leptin, leptin analogs and leptin receptor agonists, NPY receptor antagonists and modulators, ciliary neurotrophic factor, thyroid hormone receptor-beta agonists, cannabinoid CB1 receptor antagonists, melanin-concentrating hormone receptor antagonists, melanocortin-4 receptor agonists, selective muscarinic receptor M$_1$ antagonists, opioid receptor antagonists, and combinations thereof.

18. The method of claim 17, wherein said norepinephrine-dopamine reuptake inhibitor is bupropion.

19. The method of claim 17, wherein said selective serotonin reuptake inhibitor is selected from the group consisting of citalopram, escitalopram, fluoxetine, fluvoxamine, paroxetine, and sertraline.

20. The method of claim 17, wherein said anorexiant is phentermine.

21. The method of claim 17, wherein said anti-epileptic agent is topiramate.

22. The method of claim 17, wherein said selective muscarinic receptor M$_1$ antagonist is telenzepine.

23. The method of claim 17, wherein said opioid receptor antagonist is naltrexone.

* * * * *

UNITED STATES PATENT AND TRADEMARK OFFICE
CERTIFICATE OF CORRECTION

| | | |
|---|---|---|
| PATENT NO. | : 8,106,021 B2 | Page 1 of 5 |
| APPLICATION NO. | : 12/917367 | |
| DATED | : January 31, 2012 | |
| INVENTOR(S) | : Chen et al. | |

It is certified that error appears in the above-identified patent and that said Letters Patent is hereby corrected as shown below:

In the Drawing Sheets Section:

On Drawing Sheet 1, FIG. 1: please delete the entire structure in FIG. 1 and insert:

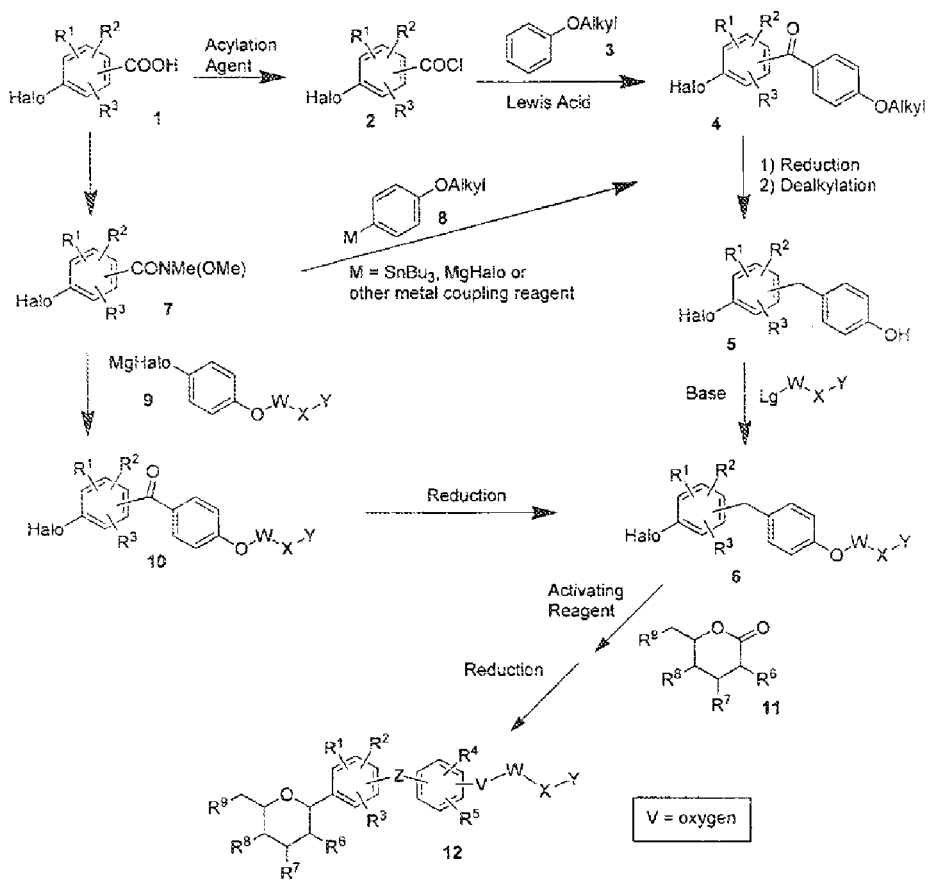

Scheme I

Signed and Sealed this
Eighteenth Day of June, 2013

Teresa Stanek Rea
*Acting Director of the United States Patent and Trademark Office*

CERTIFICATE OF CORRECTION (continued)
U.S. Pat. No. 8,106,021 B2

On Drawing Sheet 1, FIG. 2: please delete the entire structure in FIG. 2 and insert:

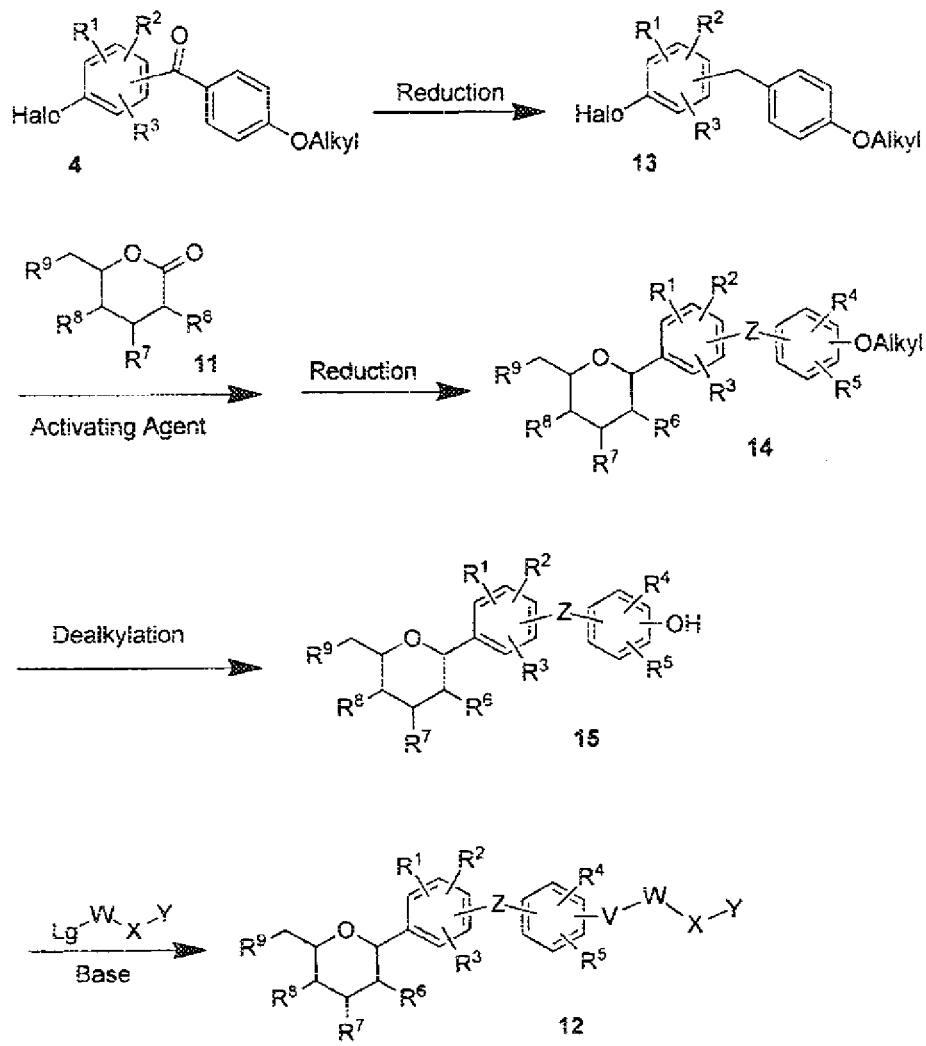

Scheme II

On Drawing Sheet 1, FIG. 3: please delete the entire structure in FIG. 3 and insert:

CERTIFICATE OF CORRECTION (continued)
U.S. Pat. No. 8,106,021 B2

Page 3 of 5

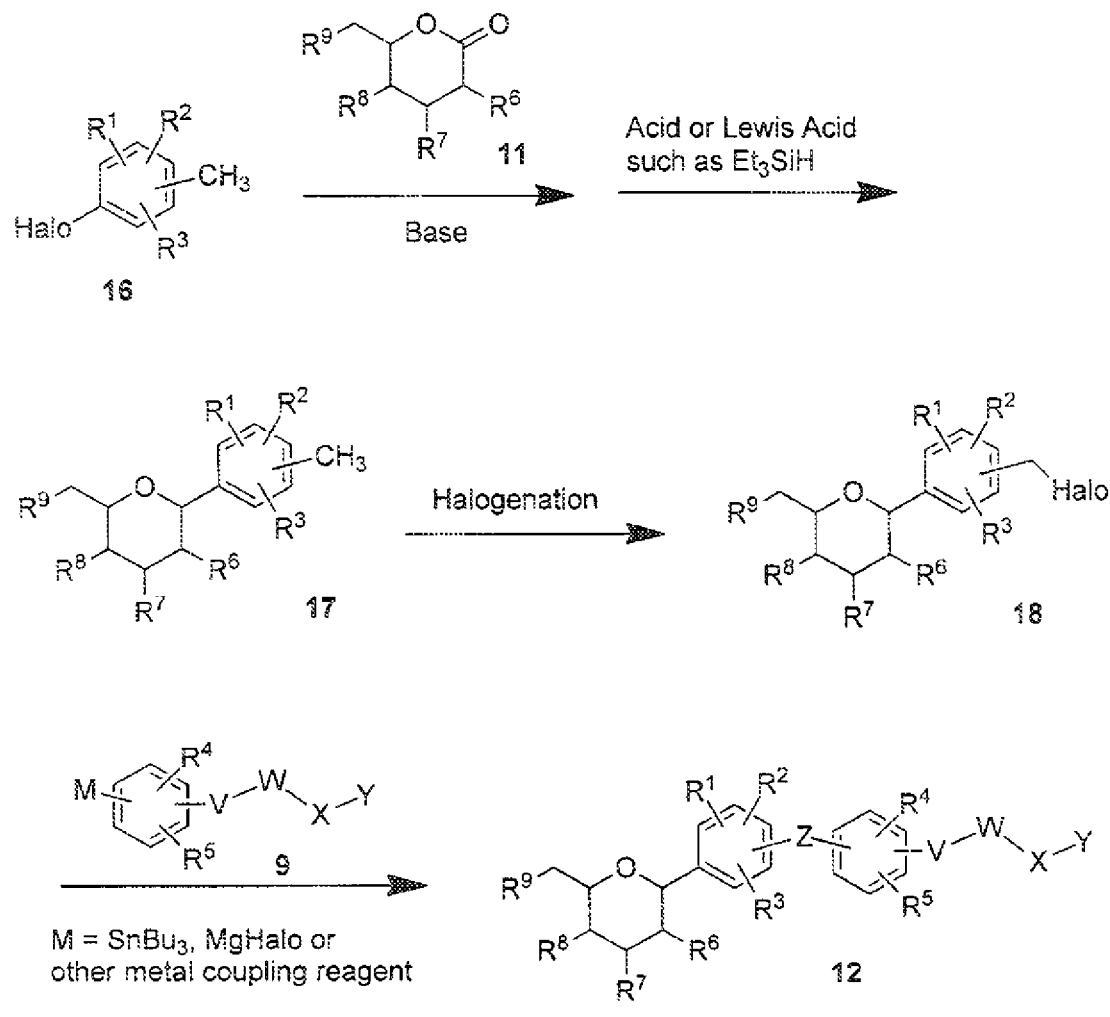

Scheme III

On Drawing Sheet 1, FIG. 4: please delete the entire structure in FIG. 4 and insert:

CERTIFICATE OF CORRECTION (continued)

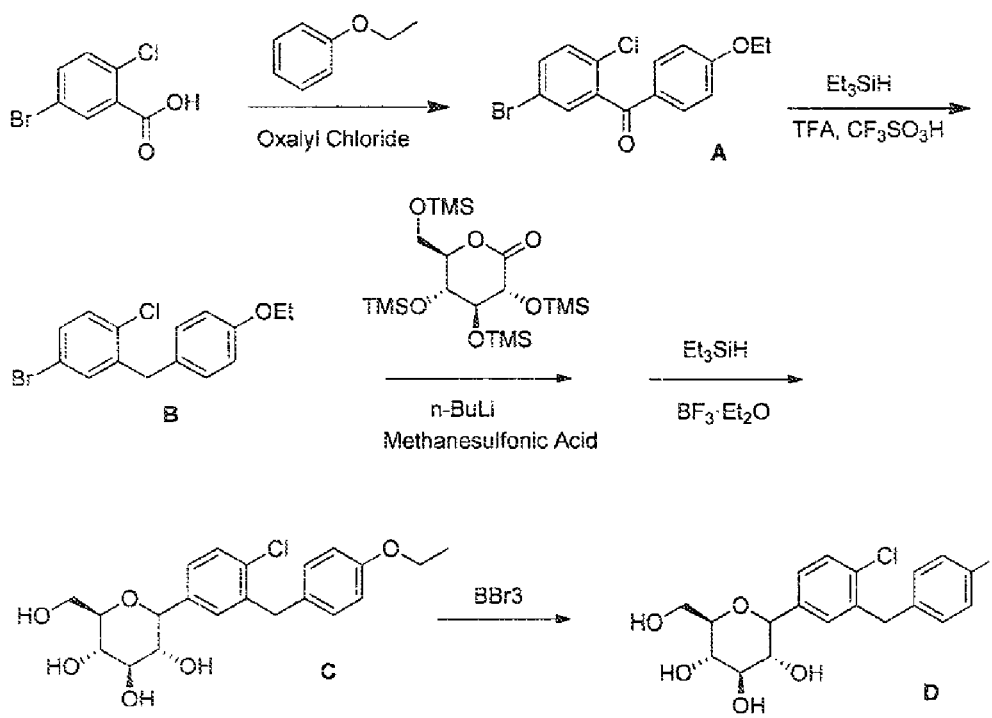

On Drawing Sheet 2, FIG. 5: please delete the entire structure in FIG. 5 and insert:

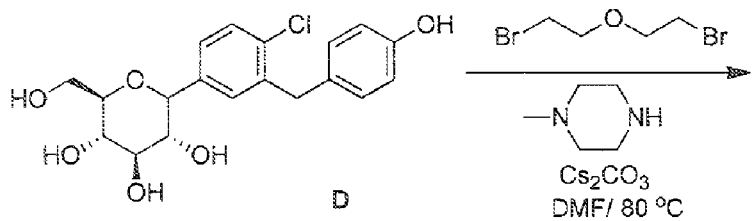

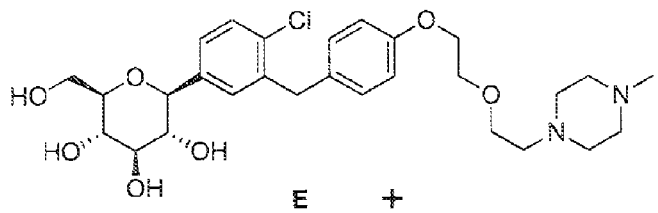

On Drawing Sheet 2, FIG. 6: please delete the entire structure in FIG. 6 and insert:

CERTIFICATE OF CORRECTION (continued)
U.S. Pat. No. 8,106,021 B2

Page 5 of 5

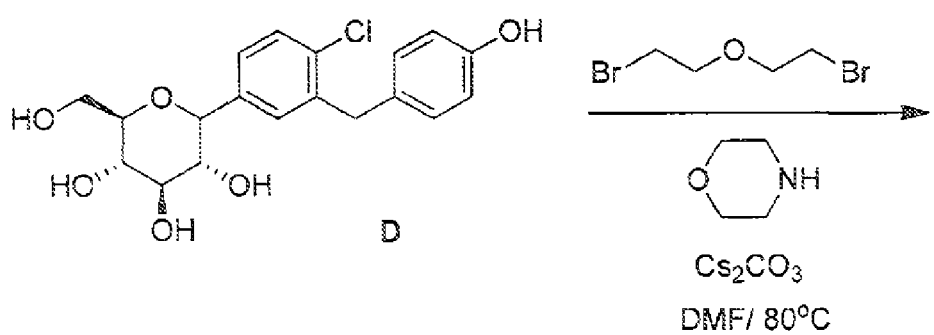

On Drawing Sheet 2, FIG. 7: please delete the entire structure in FIG. 7 and insert: